United States Patent
Covey et al.

(10) Patent No.: US 9,512,170 B2
(45) Date of Patent: Dec. 6, 2016

(54) NEUROACTIVE 13, 17-SUBSTITUTED STEROIDS AS MODULATORS FOR GABA TYPE-A RECEPTORS

(71) Applicant: Washington University, St. Louis, MO (US)

(72) Inventors: Douglas Covey, St. Louis, MO (US); Xin Jiang, Coppell, TX (US)

(73) Assignee: Washington University, St. Louis, MO (US)

( * ) Notice: Subject to any disclaimer, the term of this patent is extended or adjusted under 35 U.S.C. 154(b) by 31 days.

(21) Appl. No.: 14/191,740

(22) Filed: Feb. 27, 2014

(65) Prior Publication Data

US 2014/0249120 A1    Sep. 4, 2014

Related U.S. Application Data

(60) Provisional application No. 61/771,350, filed on Mar. 1, 2013.

(51) Int. Cl.
| | | |
|---|---|---|
| *A61K 31/57* | (2006.01) | |
| *C07J 71/00* | (2006.01) | |
| *C07J 3/00* | (2006.01) | |
| *C07J 7/00* | (2006.01) | |
| *C07J 1/00* | (2006.01) | |
| *C07J 13/00* | (2006.01) | |
| *C07J 21/00* | (2006.01) | |

(52) U.S. Cl.
CPC .............. *C07J 71/0005* (2013.01); *C07J 3/00* (2013.01); *C07J 7/002* (2013.01); *C07J 7/0005* (2013.01); *C07J 7/007* (2013.01); *C07J 1/0011* (2013.01); *C07J 13/007* (2013.01); *C07J 21/008* (2013.01)

(58) Field of Classification Search
CPC ................................ C07J 7/002; A61K 31/57
USPC ............................ 552/609; 514/18, 816, 817
See application file for complete search history.

(56) References Cited

U.S. PATENT DOCUMENTS

| | | |
|---|---|---|
| 3,206,459 A | 9/1965 | Cross |
| 4,071,625 A | 1/1978 | Grunwell et al. |
| 4,389,345 A | 6/1983 | Lenz |
| 5,925,630 A | 7/1999 | Upasani et al. |
| 7,781,421 B2 | 8/2010 | Covey et al. |
| 2002/0091112 A1 | 7/2002 | Menzenbach et al. |
| 2005/0176976 A1 | 8/2005 | Calogeropoulou et al. |
| 2006/0094696 A1 | 5/2006 | Leese et al. |
| 2010/0234335 A1 | 9/2010 | Gravanis et al. |

FOREIGN PATENT DOCUMENTS

| | | |
|---|---|---|
| DE | 2632677 A1 | 1/1978 |
| EP | 0104489 A1 | 4/1984 |
| WO | 2008151745 A1 | 12/2008 |
| WO | 2012013816 A1 | 2/2012 |
| WO | 2012083090 A2 | 6/2012 |
| WO | 2012116290 A2 | 8/2012 |

OTHER PUBLICATIONS

Ruzicka, et al., "Steroids and sex hormones. CXXXIX. The relation between constitution and odor of steroids. Methylandrostane and allopregnane derivatives," Helvetica Chimica Acta, vol. 30(3), pp. 867-878 (1947).

Heard, et al., "Steroids. VII. Preparation of androstan-3(β)-ol-7-one from dehydroisoandrosterone," Journal of Biological Chemistry, vol. 165, pp. 677-685 (1946).

Fajkos, et al., "Steroids. XXIII. Synthesis and configuration of the two stereoisomeric 3β-hydroxy-16-acetylandrostanes," Chemicke Listy pro Vedu a Prumysl, vol. 50, pp. 791-799 (1956).

International Search Report and Written Opinion issued for International Application No. PCT/US2014/016405 (Jul. 16, 2014).

Anderson, et al. "Anesthetic Activity of Novel Water-Soluble 2β-Morpholinyl Steroids and Their Modulatory Effects at GABA-A Receptors," J. Med. Chem., vol. 40, pp. 1668-1681 (1997).

Bandyopadhyaya, et al., "Neurosteroid analogues. 15. A comparative study of the anesthetic and GABAergic actions of alphaxalone, Δ 16-alphaxalone and their corresponding 17-carbonitrile analogues," Bioorg Med Chem Lett., vol. 20, Issue 22, pp. 6680-6684 (Nov. 15, 2010).

Berge et al., J. Pharmaceutical Sciences, 1977, 66, 1-19.

E. Stastna, et al., Neurosteroid Analogues. 16. A New Explanation for the Lack of Anesthetic Effects in Δ16-Alphaxalone and Identification of a Δ17(20) Analogue with Potent Anesthetic Activity, J. Med. Chem., 54(11), pp. 3926-3934 (2011).

Green, P. S.; Yang, S. H.; Nilsson, K. R.; Kumar, A. S.; Covey, D. F.; Simpkins, J. W. The nonfeminizing enantiomer of 17β-estradiol exerts protective effects in neuronal cultures and a rat model of cerebral ischemia. Endocrinology 2001, 142, 400-406.

Han, et al., "Neurosteroid Analogs. 3. The Synthesis and Electrophysiological Evaluation of Benz[e]indene Congeners of Neuroactive Steroids Having the 5â-Configuration," J. of Med. Chem., vol. 38(22), pp. 4548-4556 (1995).

Hu, Y. F.; Wittmer, L. L.; Kalkbrenner, M.; Evers, A. S.; Zorumski, C. F.; Covey, D. F. Neurosteroid analogues. Part 5. Enantiomers of neuroactive steroids and benz[e]indenes: total synthesis, electrophysiological effects on GABAA receptor function and anesthetic actions in tadpoles. J. Chem. Soc. Perkin Trans. 1 1997, 3665-3671.

International Search Report and Written Opinion for PCT/US2012/026542, dated Dec. 12, 2012, 14 pages.

(Continued)

*Primary Examiner* — Barbara P Badio
(74) *Attorney, Agent, or Firm* — Armstrong Teasdale LLP

(57) ABSTRACT

The present disclosure is generally directed to neuroactive 13,17-substituted steroids as referenced herein, and pharmaceutically acceptable salts thereof, for use as, for example, an anesthetic, and/or in the treatment of disorders relating to GABA function and activity. The present disclosure is further directed to pharmaceutical compositions comprising such compounds.

16 Claims, No Drawings

(56) References Cited

OTHER PUBLICATIONS

Kaji, et al., "Synthesis of 3-epi-6, 7- dideoxyxestobergsterol A," Chem. & Pharm. Bulletin, vol. 48(10), pp. 1480-1483 (2000).
Katona, B. W.; Krishnan, K.; Cai, Z. Y.; Manion, B. D.; Benz, A.; Taylor, A.; Evers, A. S.; Zorumski, C. F.; Mennerick, S.; Covey, D. F. Neurosteroid analogues. 12. Potent enhancement of GABA-mediated chloride currents at GABAA receptors by ent-androgens. Eur. J. Med. Chem. 2008, 43, 107-113.
Nilsson, K. R.; Zorumski, C. F.; Covey, D. F. Neurosteroid analogues. 6. The synthesis and GABAA receptor pharmacology of enantiomers of dehydroepiandrosterone sulfate, pregnenolone sulfate, and (3α,5β)-3-hydroxypregnan-20-one sulfate. J. Med. Chem. 1998, 41, 2604-2613.
Qian & Covey, "The efficient and enantiospecific total synthesis of cyclopenta[b]phenanthrenes structurally related to neurosteroids," Adv. Syn. & Cata., vol. 352 (11-12), pp. 2057-2061 (2010).
Rychnovsky & Mickus, "Synthesis of ent-cholesterol, the unnatural enantiomer," J. of Org. Chem., vol. 57(9), pp. 2732-2736 (1992).
Santaniello & Caspi, "Reduction of certain steroidal 19-sulfonic esters with metal hydrides," J. of Ster. Biochem., vol. 7 (3), pp. 223-227 (1976).
Sarett, L.H., A new method for the preparation of 17(alpha)-hydroxy-20-ketopregnanes. J. Am. Chem. Soc., 70: 1454-8 (1948).
Scaglione, et al., "Neurosteroid Analogues. 14. Alternative Ring System Scaffolds: GABA Modulatory and Anesthetic Actions of Cyclopenta[b]phenanthrenes and Cyclopenta[b]anthracenes," J. Med. Chem., vol. 51, pp. 1309-1318 (2008).
Shu Hong-Jin et al. Characteristics of concatemeric GABAA receptors containing α4/σ subunits expressed in Xenopus oocytes. British Journal of Pharmacology, 2012, 165, pp. 2228-2243.
Stastna, E.; Rath, N. P.; Covey, D. F. The use of symmetry in enantioselective synthesis: Four pairs of chrysene enantiomers prepared from 19-nortestosterone. Org. Biomol. Chem. 2011, 9, 4685-4694.
Upasani, et al., "3α-Hydroxy-3β-(phenylethynyl-5β-pregnan-20-ones: Synthesis and Pharmacological Activity of Neuroactive Steroids with High Affinity for GABA-A Receptors," J. Med. Chem., vol. 40, pp. 73-84 (1997).
Wu, Pharmaceuticals (2009) 2:77-81.
Jiang, X., et al., Neurosteroid analogues. 9. Conformationally constrained pregnanes: structure-activity studies of 13,24-cyclo-18,21-dinorcholane analogues of the GABA modulatory and anesthetic steroids (3α,5α)- and (3α,5α)-3-hydroxypregnan-20-one. J. Med. Chem., 46: 5334-48 (2003).
Cerny, et al., "Syntheses of 19-[O-(carboxymethyl)oxime] haptens of epipregnanolone and pregnanolone," Steroids, vol. 71(2), pp. 120-128 (2006).
Cerny, et al., "Synthetic approach to 5alpha-pregnanolone 19-[O-(carboxymethyl) oxime] derivatives," Collection of Czechoslovak Chemical Communications, vol. 69(9), pp. 1805-1817 (2004).
Wicha, et al., "Transformations of steroidal neopentyl systems. II. Migration of acetate from the 3beta- to the 19-hydroxyl in delta 5 and A/B-trans steroids," Canadian Journal of Chemistry, vol. 45(7), pp. 707-711 (1967).
Hill, et al., "Photochemische Reaktionen. 32 Mitteilung. UV-Bestrahlung von gesattigten und beta,gamma-ungesattigten, homoallylisch konjugierten steroidaldehyden," Helvetica Chimica Acta, vol. 49(1), pp. 292-311 (1946).
Wicha, et al., "Transformations of steroidal neopentyl systems. VII. Mechanism of the transformation of (19R)-(19)-hydroxy-19-methyl-3-oxo-5alpha-to 3alpha-hydroxy-19-methyl-19-oxo-5alpha-analogs," Journal of Organic Chemistry, vol. 38(7), pp. 1280-1283 (1973).
Wicha, et al., "Transformations of steroidal neopentyl systems. V. Synthesis and proof of the configuration of 19a-methyl-19S-alcohols," Journal of the Chemical Society [Section] C: Organic, vol. 6, pp. 947-951 (1969).
Wicha, et al., "Transformations of steroidal neopentyl systems. IV. Stereochemistry of products of reaction of methyllithium with steroidal delta5-19-aldehydes," Journal of the Chemical Society [Section] C: Organic, vol. 14, pp. 1740-1746 (1968).
Caspi, et al., "Stereochemistry of 19-hydroxy-19alpha-methyl steroids," Chemical Communications, vol. 7, pp. 209-210 (1966).
Knox, et al., "Steroids. CCLXXVIII. Reductions of 19-substituted androst-4-en-3-ones and related compounds," Journal of Organic Chemistry, vol. 30(7), pp. 2198-2205 (1965).
International Search Report and Written Opinion issued for International Application No. PCT/US2013/076214 (Jun. 5, 2014).
Uusi-Oukari, Mikko, Korpi, Esa R.; "Regulation of GABAA Receptor Subunit Expression by Pharmacological Agents"; Pharmacological Reviews, 62, 97-135 (2010).
Hauser, et al., "Steroids. CCV. Fragmentations and intramolecular abstractions of tertiary hydrogen atoms by primary oxy radicals with fixed reaction centers," Helv. Chim. Acta, vol. 47, pp. 1961-1979 (1964).
Qian, et al., "Neurosteroid Analogues, 18. Structure-Activity Studies of ent-Steroid Potentiators of γ-Aminobutyric Acid Type A Receptors and Comparison of Their Activities with Those of Alphaxalone and Allopregnanolone," J. of Med. Chem., vol. 57(1), pp. 171-190 (2014).
Ruzicka, et al., "Steroids and sex hormones. CXXXIX. The relation between constitution and odor of steroids. Methylandrostane and allopregnane derivatives," Helvetica Chimica Acta, vol. 30, pp. 867-878 (1947).
Spiegel et al., "Use of Nonaqueous Solvents in Parenteral Products," J. of Pharm. Sciences, vol. 52, No. 10, pp. 917-927 (1963).
Stastna, et al., "Stereoselectivity of sodium borohydride reduction of saturated steroidal ketones utilizing conditions of Luche reduction," Steroids, vol. 75(10), pp. 721-725 (2010).

NEUROACTIVE 13, 17-SUBSTITUTED STEROIDS AS MODULATORS FOR GABA TYPE-A RECEPTORS

CROSS-REFERENCE TO RELATED APPLICATION

This application claims priority benefit of U.S. Provisional Patent Application Ser. No. 61/771,350, filed on Mar. 1, 2013, the entire content of which is incorporated herein by reference.

GOVERNMENT SUPPORT

This invention was made with Government support under NIH Grant #GM047969, awarded by the National Institute of Health. The Government has certain rights in the invention.

BACKGROUND OF THE DISCLOSURE

The present disclosure is generally directed to novel compounds having utility as an anesthetic and/or in the treatment of disorders relating to GABA function and activity. More specifically, the present disclosure is directed to steroids having a 13,17-substituted tetracyclic structure that are neuroactive and suitable for use as an anesthetic, as well as pharmaceutically acceptable salts thereof, and pharmaceutical compositions containing them.

Gamma-aminobutyric acid (GABA) is the major inhibitory neurotransmitter of the central nervous system. GABA activates two types of receptors, the inotropic $GABA_A$ and the metabotropic $GABA_B$ receptor. Activation of the $GABA_B$ receptor by GABA causes hyperpolarization and a resultant inhibition of neurotransmitter release. The $GABA_A$ receptor subtype regulates neuronal excitability and rapid mood changes, such as anxiety, panic, and stress response. $GABA_A$ receptors are chloride ion channels; as a result, activation of the receptor induces increased inward chloride ion flux, resulting in membrane hyperpolarization and neuronal inhibition. Drugs that stimulate $GABA_A$ receptors, such as benzodiazepines and barbiturates, have anticonvulsive effects (by reducing neuronal excitability and raising the seizure threshold), as well as anxiolytic and anesthetic effects.

The effect of certain steroids on $GABA_A$ receptors has been well-established. As a result, researchers continue to pursue the discovery and synthesis of neuroactive steroids that may act as anesthetics and/or that may serve to provide treatment for disorders related to GABA function. For example, it is now widely accepted that the intravenous anesthetic alphaxalone (Compound A, below) causes general anesthesia in humans because it allosterically increases chloride currents mediated by GABA acting at $GABA_A$ receptors in the brain. However, the various structural features that enable this compound to function in the way it does have, to-date, not been fully understood. For example, in contrast to alphaxalone, $\Delta^{16}$-alphaxalone (Compound B, below), has been observed to have greatly diminished allosteric activity at $GABA_A$ receptors and is not used as an intravenous general anesthetic in humans.

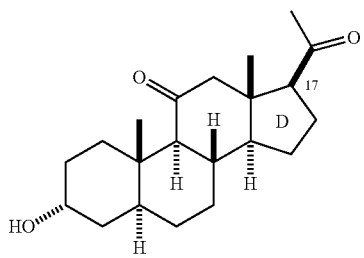

Compound A

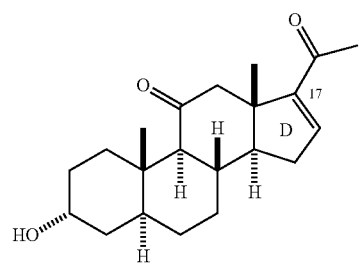

Compound B

The difference in performance of these two compounds, which some have attributed to the presence of the carbon-carbon double bond in the D-ring, has attracted the attention of many researchers. In fact, recently, it was determined that the effect this double bond has on anesthetic activity may depend on the group attached at C-17 on the D-ring. (See Bandyopadhyaya, A. K., et al., "Neurosteroid analogues. 15. A comparative study of the anesthetic and GABAergic actions of alphaxalone, $\Delta^{16}$-alphaxalone and their corresponding 17-carbonitrile analogues. Bioorg. Med. Chem. Lett., 20: 6680-4 (2010).)

In addition to anesthetic properties, neuroactive steroids may be used to treat disorders related to GABA function. For example, neuroactive steroids, such as progesterone, may be used as sedative-hypnotics, exhibiting benzodiazepine-like actions, inducing reduced sleep latency and increased non-REM sleep with only small changes in slow wave and REM sleep. Further, drugs that enhance GABA responses are often used to treat anxiety in humans. Thus, it might be expected that GABA-potentiating steroids would exhibit anxiolytic effects. Neuroactive steroids may also be used to treat depression, given that accumulating evidence suggests that patients with major depression have decreased levels of GABAergic neurosteroids and that certain treatments for depression alter levels of these steroids. Although GABA is not typically thought to play a critical role in the biology of depression, there is evidence that low GABAergic activity may predispose one to mood disorders. Finally, inhibition of NMDA receptors and enhancement of $GABA_A$ receptors appear to play important roles in mediating the acute effects of ethanol in the nervous system, while related studies suggest that GABAergic neurosteroids may be involved in some of the pharmacological effects of ethanol and that neuroactive steroids may be useful in treating ethanol withdrawal.

In view of the foregoing, it is clear that there are a number of potentially advantageous uses for neurosteroids. As a result, there is a continuing need for the further synthesis and understanding of new neuroactive steroids, particularly those having utility as an anesthetic and/or in the treatment of a disorder relating to GABA function and activity.

SUMMARY OF THE DISCLOSURE

In one aspect, the present disclosure is directed to a compound having a structure of Formula (I):

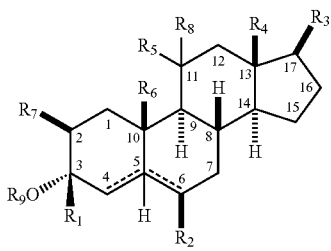

(I)

or a pharmaceutically acceptable salt thereof;
wherein:

$R_1$ is H, optionally substituted $C_1$-$C_4$ alkyl, optionally substituted $C_2$-$C_4$ alkenyl, or optionally substituted $C_2$-$C_4$ alkynyl;

$R_2$ is H, optionally substituted $C_1$-$C_4$ alkoxy, aryloxy, optionally substituted $C_2$-$C_4$ alkenoxy, optionally substituted $C_2$-$C_4$ alkynoxy, or —O—C(O)—$R_x$, where $R_x$ is optionally substituted $C_1$-$C_{20}$ alkyl;

$R_3$ is H, optionally substituted $C_1$-$C_4$ alkyl, optionally substituted $C_2$-$C_4$ alkenyl, optionally substituted alkynyl, cyclopropyl, or C(O)$R_y$, where $R_y$ is $C_1$-$C_4$ alkyl, $C_2$-$C_4$ alkenyl or $C_2$-$C_4$ alkynyl;

$R_4$ is optionally substituted $C_2$-$C_4$ alkenyl, optionally substituted $C_2$-$C_4$ alkynyl, optionally substituted cyclopropyl, or C(O)$R_z$, where $R_z$ is $C_1$-$C_4$ alkyl, $C_2$-$C_4$ alkenyl or $C_2$-$C_4$ alkynyl;

$R_5$ is H, =O, or O$R_v$, where $R_v$ is H, optionally substituted $C_1$-$C_4$ alkyl, optionally substituted $C_2$-$C_4$ alkenyl, optionally substituted $C_2$-$C_4$ alkynyl, or optionally substituted aryl;

$R_6$ is H, optionally substituted $C_1$-$C_4$ alkyl, optionally substituted $C_2$-$C_4$ alkenyl, or optionally substituted $C_2$-$C_4$ alkynyl;

$R_7$ is H, optionally substituted $C_1$-$C_4$ alkoxy, aryloxy, morpholinyl, optionally substituted $C_2$-$C_4$ alkenoxy, optionally substituted $C_2$-$C_4$ alkynoxy, or —O—C(O)—$R_w$, where $R_w$ is optionally substituted $C_1$-$C_{20}$ alkyl;

$R_8$ is, when present, H, $C_1$-$C_4$ alkyl, $C_2$-$C_4$ alkenyl, or $C_2$-$C_4$ alkynyl;

$R_9$ is H or C(O)$R_u$, where $R_u$ is optionally substituted $C_1$-$C_{20}$ alkyl, optionally substituted $C_2$-$C_{20}$ alkenyl, or optionally substituted $C_2$-$C_{20}$ alkynyl; and,

- - - denotes an optional, additional C—C bond, resulting in either a C=C bond between $C_4$-$C_5$ or $C_5$-$C_6$, with the proviso that when present, the $C_5$—H substituent is not present.

The present disclosure is still further directed to a pharmaceutical composition comprising a therapeutically effective amount of one or more of the above-noted steroids or pharmaceutically acceptable salts thereof, and optionally a pharmaceutically acceptable carrier. The present disclosure also provides kits comprising steroids, salts thereof, and/or pharmaceutical compositions thereof.

The present disclosure further provides methods of inducing anesthesia in a subject in need thereof, the method comprising administering to the subject a therapeutically effective amount of one or more of the above-noted steroids, or pharmaceutically acceptable salts thereof, or a pharmaceutical composition thereof.

The present disclosure further provides methods of treating disorders related to GABA function in a subject in need thereof, the method comprising administering to the subject a therapeutically effective amount of one or more of the above-noted steroids, or pharmaceutically acceptable salts thereof, or a pharmaceutical composition thereof. In certain embodiments, the disorder is selected from the group consisting of insomnia, mood disorders, convulsive disorders, Fragile X syndrome, anxiety, or symptoms of ethanol withdrawal.

DETAILED DESCRIPTION OF CERTAIN EMBODIMENTS

In accordance with the present disclosure, it has been discovered that compounds having certain 13,17-substituted steroid structures are neuroactive and are also suitable for use as anesthetics and in the treatment of disorders associated with GABA function, as well as pharmaceutically acceptable salts thereof. The compounds may be used, for example, as an effective continuous infusion sedative for non-surgical procedures (e.g., colonoscopy). The compounds also offer advantages over anesthetics known in the art, such as a lower likelihood for bacterial contamination, as well as an improved relationship with solubilizing agents.

1. Steroid Structure

Generally speaking, the steroid of the present disclosure has a tetracyclic, fused ring structure, such as a cyclopenta[a]phenanthrene ring system (an embodiment of which is illustrated and discussed in greater detail below), wherein the $C_3$-position of the A ring has a hydroxyl or an ester substituent in the alpha configuration, the $C_{13}$ position has a substituent attached thereto in the beta configuration selected from the group consisting of optionally substituted $C_2$-$C_4$ alkenyl, optionally substituted $C_2$-$C_4$ alkynyl, optionally substituted cyclopropyl, and C(O)$R_z$, where $R_z$ is $C_1$-$C_4$ alkyl, $C_2$-$C_4$ alkenyl or $C_2$-$C_4$ alkynyl; and the $C_{17}$-position of the D ring has a substituent attached thereto in the beta configuration selected from the group consisting of H, optionally substituted $C_1$-$C_4$ alkyl, optionally substituted $C_2$-$C_4$ alkenyl, optionally substituted alkynyl, cyclopropyl, and C(O)$R_y$, where $R_y$ is $C_1$-$C_4$ alkyl, $C_2$-$C_4$ alkenyl or $C_2$-$C_4$ alkynyl.

More particularly, however, the present disclosure is directed, in certain embodiments, to a steroid having the structure of Formula (I):

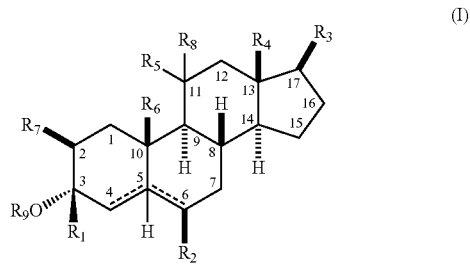

(I)

or a pharmaceutically acceptable salt thereof;
wherein:

$R_1$ is H, optionally substituted $C_1$-$C_4$ alkyl, optionally substituted $C_2$-$C_4$ alkenyl, or optionally substituted $C_2$-$C_4$ alkynyl;

$R_2$ is H, optionally substituted $C_1$-$C_4$ alkoxy, aryloxy, optionally substituted $C_2$-$C_4$ alkenoxy, optionally substituted $C_2$-$C_4$ alkynoxy, or —O—C(O)—$R_x$, where $R_x$ is optionally substituted $C_1$-$C_{20}$ alkyl;

R$_3$ is H, optionally substituted C$_1$-C$_4$ alkyl, optionally substituted C$_2$-C$_4$ alkenyl, optionally substituted alkynyl, cyclopropyl, or C(O)R$_y$, where R$_y$ is C$_1$-C$_4$ alkyl, C$_2$-C$_4$ alkenyl or C$_2$-C$_4$ alkynyl;

R$_4$ is optionally substituted C$_2$-C$_4$ alkenyl, optionally substituted C$_2$-C$_4$ alkynyl, optionally substituted cyclopropyl, or C(O)R$_z$, where R$_z$ is C$_1$-C$_4$ alkyl, C$_2$-C$_4$ alkenyl or C$_2$-C$_4$ alkynyl;

R$_5$ is H, =O, or OR$_v$, where R$_v$ is H, optionally substituted C$_1$-C$_4$ alkyl, optionally substituted C$_2$-C$_4$ alkenyl, optionally substituted C$_2$-C$_4$ alkynyl, or optionally substituted aryl;

R$_6$ is H, optionally substituted C$_1$-C$_4$ alkyl, optionally substituted C$_2$-C$_4$ alkenyl, or optionally substituted C$_2$-C$_4$ alkynyl;

R$_7$ is H, optionally substituted C$_1$-C$_4$ alkoxy, aryloxy, morpholinyl, optionally substituted C$_2$-C$_4$ alkenoxy, optionally substituted C$_2$-C$_4$ alkynoxy, or —O—C(O)—R$_w$, where R$_w$ is optionally substituted C$_1$-C$_{20}$ alkyl;

R$_8$ is, when present, H, C$_1$-C$_4$ alkyl, C$_2$-C$_4$ alkenyl, or C$_2$-C$_4$ alkynyl;

R$_9$ is H or C(O)R$_u$, where R$_u$ is optionally substituted C$_1$-C$_{20}$ alkyl, optionally substituted C$_2$-C$_{20}$ alkenyl, or optionally substituted C$_2$-C$_{20}$ alkynyl; and,

- - - denotes an optional, additional C—C bond, resulting in either a C=C bond between C$_4$-C$_5$ or C$_5$-C$_6$, with the proviso that when present, the C$_5$—H substituent is not present.

As generally defined above, R$_1$ is H, optionally substituted C$_1$-C$_4$ alkyl, optionally substituted C$_2$-C$_4$ alkenyl, or optionally substituted C$_2$-C$_4$ alkynyl. In a preferred embodiment, R$_1$ is H. R$_1$ is in the beta configuration.

As generally defined above, R$_2$ is H, optionally substituted C$_1$-C$_4$ alkoxy, aryloxy, optionally substituted C$_2$-C$_4$ alkenoxy, optionally substituted C$_2$-C$_4$ alkynoxy, or —O—C(O)—R$_x$, where R$_x$ is optionally substituted C$_1$-C$_{20}$ alkyl. In certain embodiments, R$_x$ is optionally substituted C$_1$-C$_{15}$ alkyl, C$_1$-C$_{10}$ alkyl, or C$_1$-C$_4$ alkyl. In a preferred embodiment, R$_2$ is H. In another preferred embodiment, R$_2$ is alkoxy (e.g., —OCH$_3$). R$_2$ is in the beta configuration.

As generally defined above, R$_3$ is H, optionally substituted C$_1$-C$_4$ alkyl, optionally substituted C$_2$-C$_4$ alkenyl, optionally substituted alkynyl, cyclopropyl, or C(O)R$_y$, where R$_y$ is C$_1$-C$_4$ alkyl, C$_2$-C$_4$ alkenyl or C$_2$-C$_4$ alkynyl. In certain embodiments, R$_3$ is —CH=CH$_2$. In other certain embodiments, R$_3$ is ethyl. In yet other certain embodiments, R$_3$ is C(O)CH$_3$. In certain embodiments, R$_3$ is hydroxyl alkyl. In a preferred embodiment, R$_3$ is C(OH)CH$_3$. In yet another preferred embodiment, R$_3$ is CH$_2$(OH). In other certain embodiments, R$_3$ is haloalkyl. In a preferred embodiment, R$_3$ is CH$_2$Cl. R$_3$ is in the beta configuration.

As generally defined above, R$_4$ is optionally substituted C$_2$-C$_4$ alkenyl, optionally substituted C$_2$-C$_4$ alkynyl, optionally substituted cyclopropyl, or C(O)R$_z$, where R$_z$ is C$_1$-C$_4$ alkyl, C$_2$-C$_4$ alkenyl or C$_2$-C$_4$ alkynyl. In certain embodiments, R$_4$ is —CH=CH$_2$. In other certain embodiments, R$_4$ is C(O)CH$_3$. R$_4$ is in the beta configuration.

As generally defined above, R$_5$ is H, =O, or OR$_v$, where R$_v$ is H, optionally substituted C$_1$-C$_4$ alkyl, optionally substituted C$_2$-C$_4$ alkenyl, optionally substituted C$_2$-C$_4$ alkynyl, or optionally substituted aryl. In a preferred embodiment, R$_5$ is H. In another preferred embodiment, R$_5$ is alkoxy (e.g., —OCH$_3$). R$_5$ can be in either the beta configuration or the alpha configuration.

As generally defined above, R$_6$ is H, optionally substituted C$_1$-C$_4$ alkyl, optionally substituted C$_2$-C$_4$ alkenyl, or optionally substituted C$_2$-C$_4$ alkynyl. In a preferred embodiment, R$_6$ is methyl. In another preferred embodiment, R$_6$ is substituted alkyl, and more particularly is alkoxy-substituted alkyl (e.g., —CH$_2$OCH$_3$). R$_6$ is in the beta configuration.

As generally defined above, R$_7$ is H, optionally substituted C$_1$-C$_4$ alkoxy, aryloxy, morpholinyl, optionally substituted C$_2$-C$_4$ alkenoxy, optionally substituted C$_2$-C$_4$ alkynoxy, or —O—C(O)—R$_w$, where R$_w$ is optionally substituted C$_1$-C$_{20}$ alkyl. In certain embodiments, R$_w$ is optionally substituted C$_1$-C$_{15}$ alkyl, C$_1$-C$_{10}$ alkyl, or C$_1$-C$_4$ alkyl. In a preferred embodiment, R$_7$ is H. In another preferred embodiment, R$_7$ is alkoxy (e.g., —OCH$_3$). R$_7$ is in the beta configuration.

As generally defined above, R$_8$, when present (e.g., when R$_5$ is not =O), is H, C$_1$-C$_4$ alkyl, C$_2$-C$_4$ alkenyl, or C$_2$-C$_4$ alkynyl. In a preferred embodiment, R$_8$ is H.

As generally defined above, R$_9$ is H or C(O)R$_u$, where R$_u$ is optionally substituted C$_1$-C$_{20}$ alkyl, optionally substituted C$_2$-C$_{20}$ alkenyl, or optionally substituted C$_2$-C$_{20}$ alkynyl. In certain embodiments, R$_u$ is optionally substituted C$_1$-C$_{15}$ alkyl, C$_1$-C$_{10}$ alkyl, or C$_1$-C$_4$ alkyl. In other certain embodiments, R$_u$ is optionally substituted C$_1$-C$_{15}$ alkenyl, C$_1$-C$_{10}$ alkenyl, or C$_1$-C$_4$ alkenyl. In yet other certain embodiments, R$_u$ is optionally substituted C$_1$-C$_{15}$ alkynyl, C$_1$-C$_{10}$ alkynyl, or C$_1$-C$_4$ alkynyl. In a preferred embodiment, R$_9$ is H. The OR$_9$ substituent is in the alpha configuration.

As generally defined above, - - - denotes an optional, additional C—C bond, resulting in either a C=C bond between C$_4$-C$_5$ or C$_5$-C$_6$, with the proviso that when present, the C$_5$—H substituent is not present. In certain embodiments, the additional C—C bond is absent, and the hydrogen at C$_5$ is in the alpha or beta configuration. In a preferred embodiment, the additional C—C bond is absent, and the hydrogen at C$_5$ is in the alpha configuration. In certain embodiments, - - - denotes an additional C—C bond, resulting in a C=C bond between C$_4$-C$_5$. In certain embodiments, - - - denotes an additional C—C bond, resulting in a C=C bond between C$_5$-C$_6$.

It is to be noted that the present disclosure contemplates and is intended to encompass all of the various combinations and permutations (i.e., combinations of substituent options, locations and stereochemical configurations) possible here.

For example, in various embodiments, compounds of the present disclosure have the formula of (I-a):

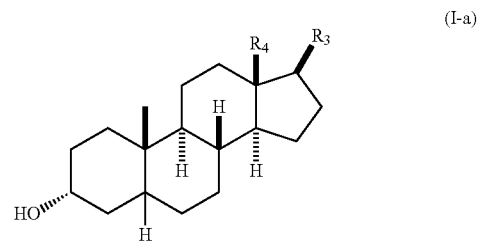

(I-a)

wherein:

R$_3$ is H, optionally substituted C$_1$-C$_4$ alkyl, optionally substituted C$_2$-C$_4$ alkenyl, optionally substituted alkynyl, cyclopropyl, or C(O)R$_y$, where R$_y$ is C$_1$-C$_4$ alkyl, C$_2$-C$_4$ alkenyl or C$_2$-C$_4$ alkynyl; and, R$_4$ is optionally substituted C$_2$-C$_4$ alkenyl, optionally substituted C$_2$-C$_4$ alkynyl, optionally substituted cyclopropyl, or C(O)R$_z$, where R$_z$ is C$_1$-C$_4$ alkyl, C$_2$-C$_4$ alkenyl or C$_2$-C$_4$ alkynyl.

As generally defined above in Formula (I-a), R$_3$ is H, optionally substituted C$_1$-C$_4$ alkyl, optionally substituted $C_2$-$C_4$ alkenyl, optionally substituted alkynyl, cyclopropyl, or $C(O)R_y$, where $R_y$ is $C_1$-$C_4$ alkyl, $C_2$-$C_4$ alkenyl or $C_2$-$C_4$ alkynyl. In certain embodiments, $R_3$ is —CH=CH$_2$. In other certain embodiments, $R_3$ is ethyl. In yet other certain embodiments, $R_3$ is $C(O)CH_3$. In certain embodiments, $R_3$ is hydroxyl alkyl. In a preferred embodiment, $R_3$ is $C(OH)CH_3$. In yet another preferred embodiment, $R_3$ is $CH_2(OH)$. In other certain embodiments, $R_3$ is haloalkyl. In a preferred embodiment, $R_3$ is $CH_2Cl$. $R_3$ is in the beta configuration.

As generally defined above in Formula (I-a), $R_4$ is optionally substituted $C_2$-$C_4$ alkenyl, optionally substituted $C_2$-$C_4$ alkynyl, optionally substituted cyclopropyl, or $C(O)R_z$, where $R_z$ is $C_1$-$C_4$ alkyl, $C_2$-$C_4$ alkenyl or $C_2$-$C_4$ alkynyl. In certain embodiments, $R_4$ is —CH=CH$_2$. In other certain embodiments, $R_4$ is $C(O)CH_3$. $R_4$ is in the beta configuration.

Accordingly, as noted, the steroid of Formulas (I) and (I-a) may encompass a number of various structures in accordance with the present disclosure, including all of the various combinations and permutations (i.e., combinations of substituent options, locations and stereochemical configurations) possible here Exemplary compounds of Formula (I) include, but are not limited to:

(XJ-99)

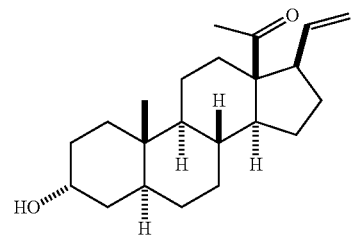

(XJ-100)

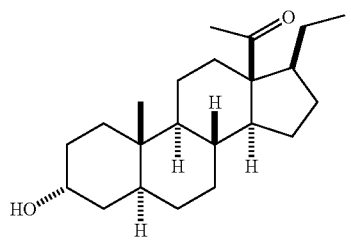

(ZYC-71)

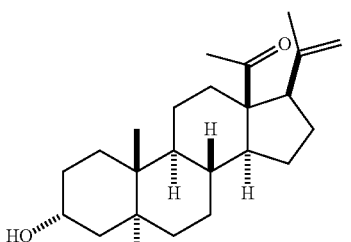

(ZYC-72)

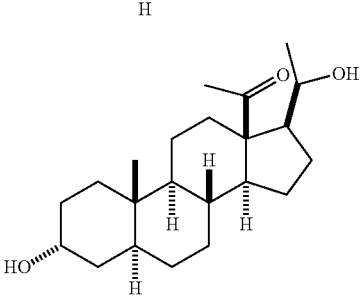

(ZYC-73)

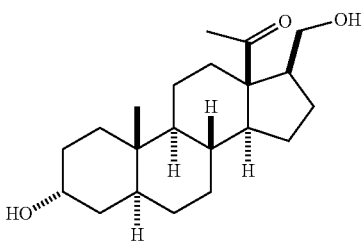

(ZYC-74)

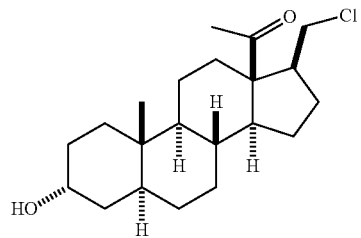

(ZYC-75)

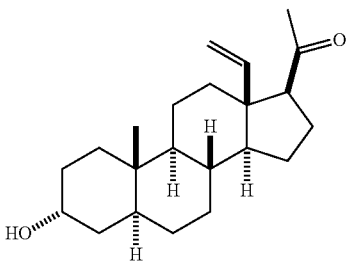

(ZYC-76)

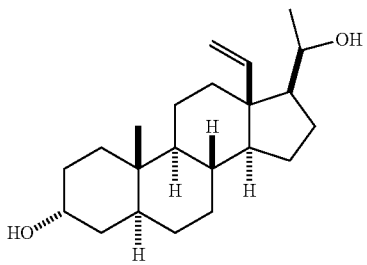

(KK-140)

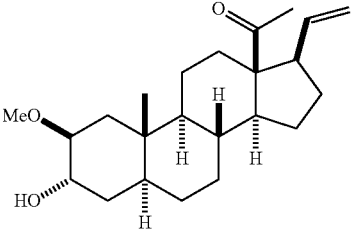

(KK-143)

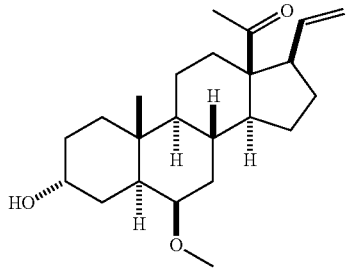

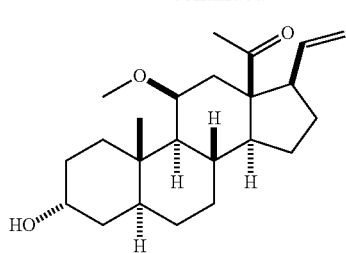

(KK-144)

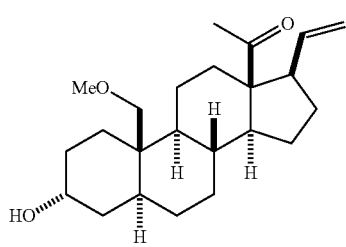

(KK-145)

and pharmaceutically acceptable salts thereof.

In this regard it is to be noted that the structures provided above are of various exemplary embodiments. As such, they should not be viewed in a limiting sense.

3. Methods of Preparation and Pharmaceutical Compositions

It is to be noted that the compounds or steroids of the present disclosure, may in various embodiments be prepared or used in accordance with means generally known in the art. For example, in certain embodiments, the steroids of the present disclosure may be prepared or used in a pharmaceutically acceptable salt form. Suitable salt forms include, for example, citrate or chloride salt forms.

In various embodiments of the present disclosure, a pharmaceutical composition is disclosed that may comprise a steroid or a combination of two or more thereof in accordance with the formulas of the present disclosure. The compounds or steroids of the present disclosure, as well as the various salt forms and other pharmaceutically acceptable forms, e.g., solvates and/or hydrates of compounds described herein, and pharmaceutical compositions containing them, may in general be prepared using methods and techniques known in the art, and/or as described in the Examples provided herein.

Without wishing to be bound by any particular theory, the compounds or steroids of the present disclosure are useful for potentiating GABA at $GABA_A$ receptors thereby inducing anesthesia or treating disorders related to GABA function (e.g., insomnia, mood disorders, Fragile X syndrome, convulsive disorders, anxiety disorders, or symptoms of ethanol withdrawal) in a subject, e.g., a human subject, and are preferably administered in the form of a pharmaceutical composition comprising an effective amount of a compound of the instant disclosure and optionally a pharmaceutically or pharmacologically acceptable carrier.

In one aspect, provided is a method of inducing anesthesia in a subject in need thereof, the method comprising administering to the subject a therapeutically effective amount of one or more of the above-noted steroids or pharmaceutically acceptable salts thereof, or a pharmaceutical composition thereof.

In another aspect, provided is a method of treating disorders related to GABA function in a subject in need thereof, the method comprising administering to the subject a therapeutically effective amount of one or more of the above-noted steroids or pharmaceutically acceptable salts thereof, or a pharmaceutical composition thereof. In certain embodiments, the disorder is selected from the group consisting of insomnia, mood disorders, convulsive disorders, Fragile X syndrome, anxiety, or symptoms of ethanol withdrawal.

In one embodiment of the present disclosure, a therapeutically effective amount of compound is from about 5 mg/kg to about 20 mg/kg, about 5 mg/kg to about 18 mg/kg, about 5 mg/kg to about 16 mg/kg, about 5 mg/kg to about 14 mg/kg, about 5 mg/kg to about 12 mg/kg, about 5 mg/kg to about 10 mg/kg, about 6 mg/kg to about 10 mg/kg, about 6 mg/kg to about 9 mg/kg, about 7 mg/kg to about 9 mg/kg, or about 8 mg/kg to about 16 mg/kg. In certain embodiments, a therapeutically effective amount of the compound is about 8 mg/kg. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The exact amount of a compound required to achieve an effective amount will vary from subject to subject, depending, for example, on species, age, and general condition of a subject, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations). In other certain embodiments, the compound may be administered via continuous intravenous (IV) infusion, such as used by those commonly skilled in the art of general anesthesia.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body.

The compound or composition can be administered concurrently with, prior to, or subsequent to, one or more additional therapeutically active agents. In general, each agent will be administered at a dose and/or on a time schedule determined for that agent. It will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually. Exemplary therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

The pharmaceutical composition may also be in combination with at least one pharmacologically acceptable carrier. The carrier, also known in the art as an excipient, vehicle, auxiliary, adjuvant, or diluent, is any substance that is pharmaceutically inert, confers a suitable consistency or form to the composition, and does not diminish the therapeutic efficacy of the compounds. The carrier is "pharmaceutically or pharmacologically acceptable" if it does not produce an adverse, allergic, or other untoward reaction when administered to a mammal or human, as appropriate.

The pharmaceutical compositions containing the compounds or steroids of the present disclosure may be formulated in any conventional manner. Proper formulation is dependent upon the route of administration chosen. The compositions of the disclosure can be formulated for any route of administration, so long as the target tissue is available via that route. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual, and intestinal administration. In certain embodiments, the route of administration is oral. In certain embodiments, the route of administration is parenteral. In certain embodiments, the route of administration is intravenous.

Pharmaceutically acceptable carriers for use in the compositions of the present disclosure are well known to those of ordinary skill in the art and are selected based upon a number of factors, including for example: the particular compound used, and its concentration, stability and intended bioavailability; the disease, disorder or condition being treated with the composition; the subject, its age, size and general condition; and/or the route of administration. Suitable carriers may be readily determined by one of ordinary skill in the art. (See, for example, J. G. Nairn, in: Remington's Pharmaceutical Science (A. Gennaro, ed.), Mack Publishing Co., Easton, Pa., (1985), pp. 1492-1517.)

The compositions may be formulated as tablets, dispersible powders, pills, capsules, gelcaps, caplets, gels, liposomes, granules, solutions, suspensions, emulsions, syrups, elixirs, troches, dragees, lozenges, or any other dosage form that can be administered orally. Techniques and compositions for making oral dosage forms useful in the present disclosure are described in the following exemplary references: 7 Modern Pharmaceutics, Chapters 9 and 10 (Banker & Rhodes, Editors, 1979); Lieberman et al., Pharmaceutical Dosage Forms: Tablets (1981); and, Ansel, Introduction to Pharmaceutical Dosage Forms 2nd Edition (1976).

The compositions of the present disclosure designed for oral administration comprise an effective amount of a compound of the disclosure in a pharmaceutically acceptable carrier. Suitable carriers for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, tragacanth, microcrystalline cellulose, colloidal silicon dioxide, croscarmellose sodium, talc, magnesium stearate, and stearic acid. Further, such solid dosage forms may be uncoated or may be coated by known techniques (e.g., to delay disintegration and absorption).

The compounds and steroids of the present disclosure may also be formulated for parenteral administration (e.g., formulated for injection via intravenous, intraarterial, subcutaneous, rectal, subcutaneous, intramuscular, intraorbital, intracapsular, intraspinal, intraperitoneal, or intrasternal routes). The compositions of the present disclosure for parenteral administration comprise an effective amount of the compound in a pharmaceutically acceptable carrier. Dosage forms suitable for parenteral administration include solutions, suspensions, dispersions, emulsions or any other dosage form that can be administered parenterally. Techniques and compositions for making parenteral dosage forms are known in the art. Typically formulations for parenteral administration are sterile or are sterilized before administration.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristrate, fatty acid derived PEG esters such as PEG-hydroxyoleate and PEG-hydroxystearate, N-methylpyrrolidinone, pluronic 60, polyoxyethylene sorbitol oleic polyesters such as poly(ethoxylated)$_{30\text{-}60}$ sorbitol poly(oleate)$_{2\text{-}4}$, poly(oxyethylene)$_{15\text{-}20}$ monooleate, poly(oxyethylene)$_{15\text{-}20}$ mono 12-hydroxystearate, and poly(oxyethylene)$_{15\text{-}20}$ mono-ricinoleate, polyoxyethylene sorbitan esters (such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del.), polyvinylpyrrolidone, alkyleneoxy modified fatty acid esters (such as polyoxyl 40 hydrogenated castor oil, cyclodextrins or modified cyclodextrins (e.g., beta-hydroxypropyl-cyclodextrin)), saccharide fatty acid esters (i.e., the condensation product of a monosaccharide (e.g., pentoses, such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$-$C_{22}$ fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfone, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzine; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the disclosure are well known to those of ordinary skill in the art, and are identified in The Handbook of Pharmaceutical Excipients, (American Pharmaceutical Association, Washington, D.C., and The Pharmaceutical Society of Great Britain, London, England, 1968), Modern Pharmaceutics, (G. Banker et al., eds., 3d ed.)(Marcel Dekker, Inc., New York, N.Y., 1995), The Pharmacological Basis of Therapeutics, (Goodman & Gilman, McGraw Hill Publishing), Pharmaceutical Dosage Forms, (H. Lieberman et al., eds.) (Marcel Dekker, Inc., New York, N.Y., 1980), Remington's Pharmaceutical Sciences (A. Gennaro, ed., 19th ed.)(Mack Publishing, Easton, Pa., 1995), The United States Pharmacopeia 24, The National Formulary 19, (National Publishing, Philadelphia, Pa., 2000), A. J. Spiegel et al., and Use of Nonaqueous Solvents in Parenteral Products, J. of Pharm. Sciences, Vol. 52, No. 10, pp. 917-927 (1963).

Preferred solvents include cyclodextrins or modified cyclodextrins (e.g., beta-hydroxypropyl-cyclodextrin) as well as oils rich in triglycerides, for example, safflower oil, soybean oil or mixtures thereof, and alkyleneoxy modified fatty acid esters such as polyoxyl 40 hydrogenated castor oil. Commercially available triglycerides include Intralipid® emulsified soybean oil (Kabi-Pharmacia Inc., Stockholm, Sweden), Nutralipid® emulsion (McGaw, Irvine, Calif.), Liposyn® II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), Liposyn® III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels between 25% and 100% by weight based on the total fatty acid content (Dhasco® (from Martek Biosciences Corp., Columbia, Md.), DHA Maguro® (from Daito Enterprises, Los Angeles, Calif.), Soyacal®, and Travemulsion®.

Additional minor components can be included in the compositions of the disclosure for a variety of purposes well known in the pharmaceutical industry. These components will for the most part impart properties which enhance retention of the compound at the site of administration, protect the stability of the composition, control the pH, facilitate processing of the compound into pharmaceutical formulations, and the like. Preferably, each of these components is individually present in less than about 15 wt % of the total composition, more preferably less than about 5 wt %, and most preferably less than about 0.5 wt % of the total composition. Some components, such as fillers or diluents, can constitute up to 90 wt % of the total composition, as is well known in the formulation art. Such additives include cryoprotective agents for preventing reprecipitation, surface active, wetting or emulsifying agents (e.g., lecithin, polysorbate-80, Tween® 80, Pluronic 60, polyoxyethylene stearate), preservatives (e.g., ethyl-p-hydroxybenzoate), microbial preservatives (e.g., benzyl alcohol, phenol, m-cresol, chlorobutanol, sorbic acid, thimerosal and paraben), agents for adjusting pH or buffering agents (e.g., acids, bases, sodium acetate, sorbitan monolaurate), agents for adjusting osmolarity (e.g., glycerin), thickeners (e.g., aluminum monostearate, stearic acid, cetyl alcohol, stearyl alcohol, guar gum, methyl cellulose, hydroxypropylcellulose, tristearin, cetyl wax esters, polyethylene glycol), colorants, dyes, flow aids, non-volatile silicones (e.g., cyclomethicone), clays (e.g., bentonites), adhesives, bulking agents, flavorings, sweeteners, adsorbents, fillers (e.g., sugars such as lactose, sucrose, mannitol, or sorbitol, cellulose, or calcium phosphate), diluents (e.g., water, saline, electrolyte solutions), binders (e.g., starches such as maize starch, wheat starch, rice starch, or potato starch, gelatin, gum tragacanth, methyl cellulose, hydroxypropyl methylcellulose, sodium carboxymethyl cellulose, polyvinylpyrrolidone, sugars, polymers, acacia), disintegrating agents (e.g., starches such as maize starch, wheat starch, rice starch, potato starch, or carboxymethyl starch, cross-linked polyvinyl pyrrolidone, agar, alginic acid or a salt thereof such as sodium alginate, croscarmellose sodium or crospovidone), lubricants (e.g., silica, talc, stearic acid or salts thereof such as magnesium stearate, or polyethylene glycol), coating agents (e.g., concentrated sugar solutions including gum arabic, talc, polyvinyl pyrrolidone, carbopol gel, polyethylene glycol, or titanium dioxide), and antioxidants (e.g., sodium metabisulfite, sodium bisulfite, sodium sulfite, dextrose, phenols, and thiophenols).

Dosage from administration by these routes may be continuous or intermittent, depending, for example, upon the patient's physiological condition, whether the purpose of the administration is therapeutic or prophylactic, and other factors known to and assessable by a skilled practitioner.

Those with ordinary skill in administering anesthetics can readily determine dosage and regimens for the administration of the pharmaceutical compositions of the disclosure or titrating to an effective dosage for use in treating insomnia, mood disorders, convulsive disorders, anxiety or symptoms of ethanol withdrawal. It is understood that the dosage of the compounds will be dependent upon the age, sex, health, and weight of the recipient, kind of concurrent treatment, if any, frequency of treatment, and the nature of the effect desired. For any mode of administration, the actual amount of compound delivered, as well as the dosing schedule necessary to achieve the advantageous effects described herein, will also depend, in part, on such factors as the bioavailability of the compound, the disorder being treated, the desired therapeutic dose, and other factors that will be apparent to those of skill in the art. The dose administered to an animal, particularly a human, in the context of the present disclosure should be sufficient to affect the desired therapeutic response in the animal over a reasonable period of time. Preferably, an effective amount of the compound, whether administered orally or by another route, is any amount that would result in a desired therapeutic response when administered by that route. The dosage may vary depending on the dosing schedule, which can be adjusted as necessary to achieve the desired therapeutic effect. The most preferred dosage will be tailored to the individual subject, as is understood and determinable by one of ordinary skill in the art without undue experimentation.

In one embodiment, solutions for oral administration are prepared by dissolving the compound in any pharmaceutically acceptable solvent capable of dissolving a compound (e.g., ethanol or methylene chloride) to form a solution. An appropriate volume of a carrier which is a solution, such as beta-hydroxypropyl-cyclodextrin, is added to the solution while stirring to form a pharmaceutically acceptable solution for oral administration to a patient. If desired, such solutions can be formulated to contain a minimal amount of, or to be free of, ethanol, which is known in the art to cause adverse physiological effects when administered at certain concentrations in oral formulations.

In another embodiment, powders or tablets for oral administration are prepared by dissolving a compound in any pharmaceutically acceptable solvent capable of dissolving the compound (e.g., ethanol or methylene chloride) to form a solution. The solvent can optionally be capable of evaporating when the solution is dried under vacuum. An additional carrier can be added to the solution prior to drying, such as beta-hydroxypropyl-cyclodextrin. The resulting solution is dried under vacuum to form a glass. The glass is then mixed with a binder to form a powder. The powder can be mixed with fillers or other conventional tabletting agents and processed to form a tablet for oral administration to a patient. The powder can also be added to any liquid carrier as described above to form a solution, emulsion, suspension or the like for oral administration.

Emulsions for parenteral administration can be prepared by dissolving a compound in any pharmaceutically acceptable solvent capable of dissolving the compound (e.g., ethanol or methylene chloride) to form a solution. An appropriate volume of a carrier which is an emulsion, such as Liposyn® II or Liposyn® III emulsions, is added to the solution while stirring to form a pharmaceutically acceptable emulsion for parenteral administration to a patient.

Solutions for parenteral administration can be prepared by dissolving a compound in any pharmaceutically acceptable solvent capable of dissolving the compound (e.g., ethanol or methylene chloride) to form a solution. An appropriate volume of a carrier which is a solution, such as beta-hydroxypropyl-cyclodextrin, is added to the solution while stirring to form a pharmaceutically acceptable solution for parenteral administration to a patient.

If desired, the emulsions or solutions described above for oral or parenteral administration can be packaged in IV bags, vials or other conventional containers in concentrated form and diluted with any pharmaceutically acceptable liquid, such as saline, to form an acceptable concentration prior to use as is known in the art.

Still further encompassed by the disclosure are kits (e.g., pharmaceutical packs). The kits provided may comprise a compound as described herein and a container (e.g., a vial, ampule, bottle, syringe, and/or dispenser package, or other suitable container). In some embodiments, provided kits may optionally further include a second container comprising a pharmaceutical carrier for dilution or suspension of the pharmaceutical composition or compound. In some embodiments, the pharmaceutical composition or compound provided in the container and the second container are combined to form one unit dosage form.

Optionally, instructions for use are additionally provided in such kits of the disclosure. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with an additional therapeutic agent.

4. Definitions

The term "steroid" as used herein describes an organic compound containing in its chemical nucleus the cyclopenta[a]phenanthrene ring system.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, a "subject" to which administration is contemplated includes, but is not limited to, mammals, e.g., humans (i.e., a male or female of any age group, e.g., a pediatric subject (e.g., child, adolescent) or adult subject (e.g., young adult, middle-aged adult or senior adult)), other primates (e.g., cynomolgus monkeys, rhesus monkeys) and commercially relevant mammals such as cattle, pigs, horses, sheep, goats, cats, and/or dogs. In any aspect and/or embodiment of the disclosure, the subject is a human.

As used herein, a "therapeutically effective amount" "an amount sufficient" or "sufficient amount" of a compound means the level, amount or concentration of the compound required for a desired biological response, e.g., analgesia.

The term "saturated" as used herein describes the state in which all available valence bonds of an atom (especially carbon) are attached to other atoms.

The term "unsaturated" as used herein describes the state in which not all available valence bonds along the alkyl chain are satisfied; in such compounds the extra bonds usually form double or triple bonds (chiefly with carbon).

When a range of values is listed, it is intended to encompass each value and sub-range within the range. For example "$C_{1-4}$ alkyl" is intended to encompass, $C_1$, $C_2$, $C_3$, $C_4$, $C_{1-3}$, $C_{1-2}$, $C_{2-4}$, $C_{2-3}$ and $C_{3-4}$ alkyl, while "$C_{1-22}$ alkyl" is intended to encompass, for example, $C_1$, $C_2$, $C_3$, $C_4$, etc., as well as $C_{1-21}$, $C_{1-20}$, $C_{1-15}$, $C_{1-10}$, $C_{2-20}$, $C_{2-15}$, $C_{2-10}$, $C_{3-15}$, $C_{3-10}$, etc. alkyl.

As used herein, "alkyl" refers to a radical of a straight-chain or branched saturated hydrocarbon group having from, in some embodiments, 1 to 4 carbon atoms ("$C_{1-4}$ alkyl"), and in other embodiments 1 to 22 carbon atoms ("$C_{1-22}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 4 carbon atom ("$C_{2-4}$ alkyl"). In yet other embodiments, an alkyl group has 1 to 21 carbon atoms ("$C_{1-21}$ alkyl"), 1 to 20 carbon atoms ("$C_{1-20}$ alkyl"), 1 to 15 carbon atoms ("$C_{1-15}$ alkyl"), 1 to 10 carbon atoms ("$C_{1-10}$ alkyl"), etc. Examples of such alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), pentyl ($C_5$), and the like.

As used herein, "alkenyl" or "alkene" refers to a radical of a straight-chain or branched hydrocarbon group having from, in some embodiments, 2 to 4 carbon atoms ("$C_{2-4}$ alkenyl"), and in other embodiments 2 to 22 carbon atoms ("$C_{2-22}$ alkenyl"), and one or more carbon-carbon double bonds. In some embodiments, an alkenyl group has 2 to 3 carbon atoms ("$C_{2-3}$ alkenyl"). In some embodiments, an alkenyl group has 2 carbon atoms ("$C_2$ alkenyl"). In yet other embodiments, an alkenyl group has 2 to 21 carbon atoms ("$C_{2-21}$ alkenyl"), 2 to 20 carbon atoms ("$C_{2-20}$ alkenyl"), 2 to 15 carbon atoms ("$C_{2-15}$ alkenyl"), 2 to 10 carbon atoms ("$C_{2-10}$ alkyl"), etc. The one or more carbon-carbon double bonds can be internal (such as in 2-butenyl) or terminal (such as in 1-butenyl). Examples of such alkenyl groups include ethenyl ($C_2$), 1-propenyl (C3), 2-propenyl ($C_3$), 1-butenyl ($C_4$), 2-butenyl ($C_4$), butadienyl ($C_4$), 1-pentenyl ($C_5$), 2-pentenyl ($C_5$), and the like.

As used herein, "alkynyl" or "alkyne" refers to a radical of a straight-chain or branched hydrocarbon group having from 2 to 4 carbon atoms and one or more carbon-carbon triple bonds ("$C_{2-10}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like.

As used herein, "aryl" refers to a radical of a monocyclic or polycyclic (e.g., bicyclic or tricyclic) 4n+2 aromatic ring system (e.g., having 6, 10, or 14 electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{1-4}$ aryl"; e.g., anthracyl).

As used herein, "alkoxy" refers to an alkyl, alkenyl, or alkynyl group, as defined herein, attached to an oxygen radical.

Alkyl, alkenyl, alkynyl, and aryl groups, as defined herein, are substituted or unsubstituted, also referred to herein as "optionally substituted". In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that result in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary substituents include groups that contain a heteroatom (such as nitrogen, oxygen, silicon, phosphorous, boron, sulfur, or a halogen atom), halogen (e.g., chlorine, bromine, fluorine, or iodine), a heterocycle, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

EXAMPLES

The following Examples describe or illustrate various embodiments of the present disclosure. Other embodiments within the scope of the appended claims will be apparent to a skilled artisan considering the specification or practice of the disclosure as described herein. It is intended that the specification, together with the Examples, be considered exemplary only, with the scope and spirit of the disclosure being indicated by the claims, which follow the Example.

Compound Chemistry

In accordance with the following methods and Examples, the following compounds were prepared using methods known in the industry.

Scheme 1

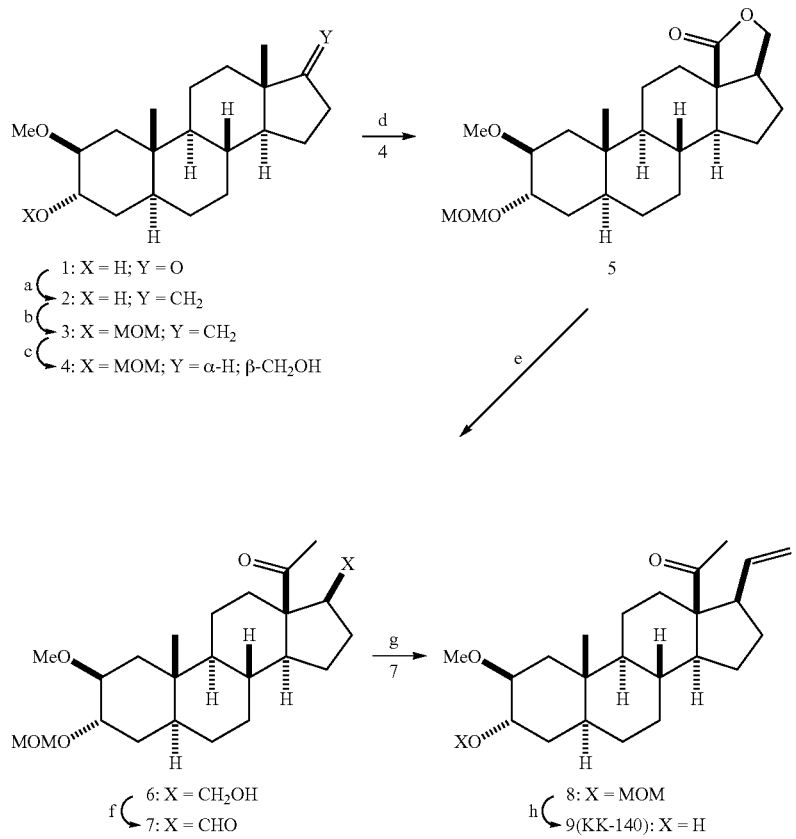

In accordance with Scheme 1, the following compounds were prepared, using methods generally known in the art and as outlined below.

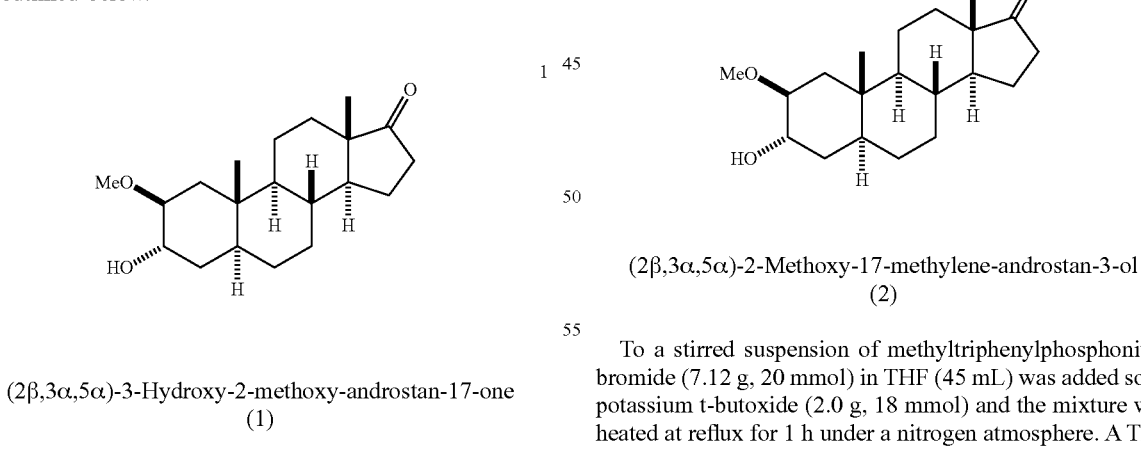

(2β,3α,5α)-3-Hydroxy-2-methoxy-androstan-17-one (1)

Compound 1 was prepared as described previously (see, e.g., Qian, et al., "Neurosteroid Analogues, 18. Structure-Activity Studies of ent-Steroid Potentiators of γ-Aminobutyric Acid Type A Receptors and Comparison of Their Activities with Those of Alphaxalone and Allopregnanolone," J. of Med. Chem., Vol. 57(1), pages 171-190 (2014)).

(2β,3α,5α)-2-Methoxy-17-methylene-androstan-3-ol (2)

To a stirred suspension of methyltriphenylphosphonium bromide (7.12 g, 20 mmol) in THF (45 mL) was added solid potassium t-butoxide (2.0 g, 18 mmol) and the mixture was heated at reflux for 1 h under a nitrogen atmosphere. A THF solution (10 mL) of compound 1 (650 mg, 2.1 mmol) was added to the resulting refluxing yellow, methylene triphenylphosphorane solution using a syringe. Reflux was continued for 3 h. The reaction mixture was cooled to room temperature, water was added and the product was extracted into EtOAc. The combined extracts were dried and concentrated to give an oil. The crude product was purified by flash column chromatography (silica gel eluted 20-40% EtOAc in hexanes) to give compound 2 as a white solid (580 mg, 90%): mp 131-133° C.; IR $v_{max}$ 3369, 2930, 2851, 1654, 1451, 1371, 1256, 1214 cm$^{-1}$; $^1$H NMR (CDCl$_3$) δ 4.60 (m, 2H), 3.93 (s, 1H), 3.34 (s, 1H), 3.33 (s, 3H), 2.45 (m, 1H), 2.17 (m, 1H), 0.94 (s, 3H), 0.76 (s, 3H); $^{13}$C NMR (CDCl$_3$) δ 161.9, 100.5, 80.7, 68.2, 56.6, 55.2, 54.4, 44.1, 39.0, 36.0, 35.7, 35.5, 34.8, 32.1, 31.8, 29.3, 28.0, 24.0, 20.7, 18.5, 13.1.

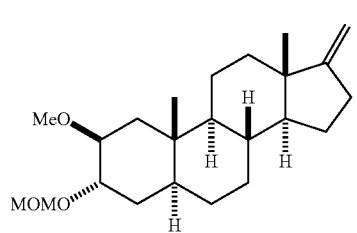

(2β,3α,5α)-2-Methoxy-3-(methoxymethoxy)-17-methylene-androstane (3)

A mixture of compound 2 (620 mg, 1.94 mmol), Hunig's base (1.75 mL, 10 mmol), chloromethyl methyl ether (0.45 mL, 6 mmol) dissolved in CH$_2$Cl$_2$ (7 mL) was stirred at room temperature for 12 h. Aqueous NaHCO$_3$ (5%, 8 mL) was added and the product extracted into CH$_2$Cl$_2$. The CH$_2$Cl$_2$ extract was dried and concentrated to give an oil. The crude product was purified by flash column chromatography (silica gel eluted with 15% EtOAc in hexanes) to give compound 3 as a colorless oil (650 mg, 92%): IR $v_{max}$ 2930, 1655, 1451, 1371, 1218 cm$^{-1}$; $^1$H NMR (CDCl$_3$) δ 4.64 (apparent q, 2H, J=7 Hz), 4.57 (m, 2H), 3.75 (s, 1H), 3.38 (s, 1H), 3.35 (s, 3H), 3.30 (s, 3H), 2.46 (m, 1H), 2.20 (m, 1H), 0.93 (s, 3H), 0.75 (s, 3H); $^{13}$C NMR (CDCl$_3$) δ 161.9, 100.5, 95.2, 79.0, 73.4, 56.5, 55.2, 55.1, 54.4, 44.1, 39.6, 36.1, 35.8, 35.7, 34.8, 31.8, 29.7, 28.1, 24.0, 20.7, 18.5, 13.0.

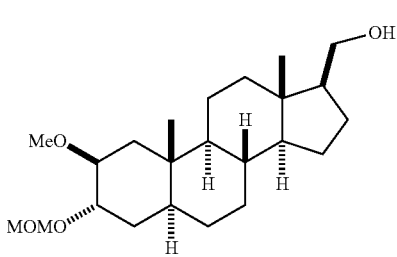

(2β,3α,5α,17β)-2-Methoxy-3-(methoxymethoxy)-androstane-17-methanol (4)

To a solution of compound 3 (363 mg, 1 mmol) in THF (5 mL) was added 9-BBN (6 mL, 0.5 M solution) in THF and the mixture was stirred at room temperature for 15 h. The reaction mixture was cooled to ° C. A mixture of 30% hydrogen peroxide (15 mL) and 3 M aqueous NaOH (15 mL) was added to the cold solution and stirred at room temperature for 2 h. Water (100 mL) was added and the product was extracted into Et$_2$O. The Et$_2$O extract was washed with brine, dried and concentrated to give a viscous liquid. The crude product was purified by flash column chromatography (silica gel eluted with 20-35% EtOAc in hexanes) to give compound 4 as an oil (323 mg, 85%): IR $v_{max}$ 3401, 2929, 1448, 1381, 1219 cm$^{-1}$; $^1$H NMR (CDCl$_3$) δ 4.60 (apparent q, 2H, J=7.0 Hz), 3.76 (m, 1H), 3.70 (s, 1H), 3.61 (m, 1H), 3.43 (m, 1H), 3.30 (s, 3H), 3.25 (s, 3H), 0.87 (s, 3H), 0.56 (s, 3H); $^{13}$C NMR (CDCl$_3$) δ 95.1, 78.8, 73.3, 64.1, 56.3, 55.8, 55.1, 52.7, 41.7, 39.4, 38.6, 36.0, 35.6, 34.4, 31.9, 29.6, 28.0, 27.2, 25.5, 24.3, 22.5, 20.4, 12.9, 12.4.

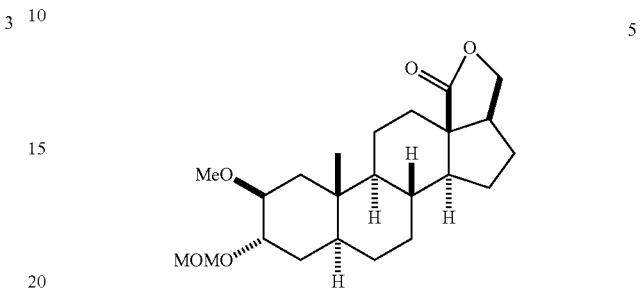

(2β,3α,5α,17β)-17-Hydroxymethyl-2-methoxy-3-(methoxymethoxy)-androstan-18-oic acid, γ-lactone (5)

To a solution of compound 4 (300 mg, 0.79 mmol) in cyclohexane (50 mL) maintained at reflux by irradiation with a high intensity tungsten lamp were added iodine (345 mg, 2.7 mmol) and lead tetraacetate (1.35 g, 3 mmol)) and the mixture was allowed to reflux for 80 min. One more portion of lead tetraacetate (0.75 g, 1.7 mmol) was added and reflux was continued for another 50 minutes. The hot cyclohexane solution was filtered through a pad of celite and the filtrate was collected. The filter cake was washed with EtOAc and the washings were collected. The combined filtrate and washings were concentrated to give a brown solution containing some particulate material. Solvents were removed and the crude product was dissolved in acetone and stirred at room temperature. Jones reagent was added dropwise until an orange color persisted. The excess Jones reagent was consumed by adding few drops of 2-propanol and the solution was diluted with water and the product extracted into EtOAc. The extract was washed with brine, dried and concentrated to give a colorless oil which was purified by flash column chromatography (silica gel eluted with 15-25% EtOAc in hexanes) to give to give compound 5 an oil (150 mg, 48%). IR $v_{max}$ 2931, 1760, 1447, 1370, 1236 cm$^{-1}$; $^1$H NMR (CDCl$_3$) δ 4.66 (apparent q, 2H, J=6.7 Hz), 4.30 (dd, 1H, J=9.0 Hz, J=5.1 Hz) 4.06 (d, 1H, J=9.0 Hz), 3.76 (s, 1H), 3.39 (s, 1H), 3.36 (s, 3H), 3.30 (s, 3H), 0.99 (s, 3H), 0.93 (m, 1H) 0.75 (m, 1H); $^{13}$C NMR (CDCl$_3$) δ 179.5, 95.3, 78.9, 73.5, 72.2, 56.5, 55.33, 55.28, 54.2, 53.4, 45.2, 39.6, 36.2, 35.8, 32.9, 32.3, 31.7, 31.4, 29.7, 27.9, 27.3, 20.2, 13.1.

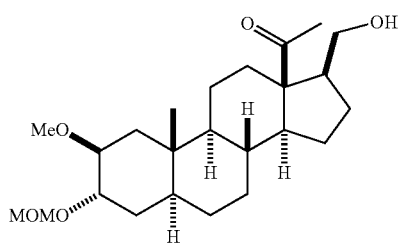

1-[(2β,3α,5α,17β)-17-Hydroxymethyl-2-methoxy-3-(methoxymethoxy)-18-norandrostan-13-yl]ethanone (6)

To a refluxing solution of compound 5 (115 mg, 0.29 mmol) in Et$_2$O was added CH$_3$Li (2 M in Et$_2$O, 2 mL, 4 mmol) and the mixture was heated at reflux for 40 minutes. The reaction mixture was cooled to 0° C. and water (20 mL) was added. The biphasic solution was separated the aqueous layer extracted with Et$_2$O. The combined original Et$_2$O layer and Et$_2$O extracts were washed with brine dried and concentrated to give a colorless oil which was purified by flash column chromatography on silica gel to give compound 6 as an oil (90 mg, 78%): IR v$_{max}$ 3468, 2928, 1694, 1448, 1356 cm$^{-1}$; $^1$H NMR (CDCl$_3$) δ 4.65 (apparent q, 2H, J=6.6 Hz), 3.75 (s, 1H), 3.50 (m, 2H), 3.36 (s, 3H), 3.35 (s, 1H), 3.30 (s, 3H), 2.68 (m, 1H), 2.20 (s, 3H), 0.82 (s, 3H), 0.77 (m, 1H); $^{13}$C NMR (CDCl$_3$) δ 213.9, 95.3, 78.9, 73.5, 63.9, 61.1, 57.6, 56.5, 55.3, 53.0, 39.6, 36.3, 36.1, 35.7, 35.7, 31.9, 30.3, 29.7, 27.9, 25.7, 24.8, 23.1, 13.2.

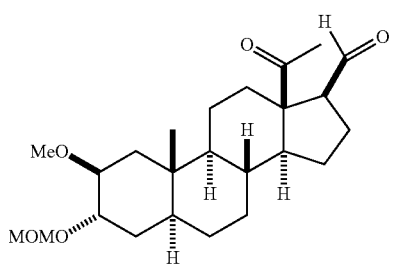

7

(2β,3α,5α,17β)-13-Acetyl-2-methoxy-3-(methoxymethoxy)-18-norandrostan-17-carboxaldehyde (7)

Compound 6 (65 mg, 0.16 mmol) was stirred in a DMSO (4 mL) solution of iodoxybenzoic acid (622 mg, 45% by weight, 1 mmol) at room temperature for 3 h. Water was added and the product extracted into EtOAc. The extract was washed with brine, dried and concentrated to give an oil which was purified by filtering through a short silica gel column eluted with 30% ethyl acetate hexanes to yield compound 7 which was dissolved in THF and kept at 0° C. and immediately converted without characterization ($^1$H NMR confirmed the presence of the aldehyde group) to compound 8.

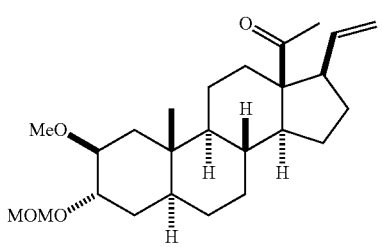

8

1-[(2α,3α,5α)-2-Methoxy-3-(methoxymethoxy)-18-norpregn-20-en-13-yl]ethanone (8)

To a stirred suspension of methyltriphenylphosphonium bromide (7.12 g, 20 mmol) in THF (45 mL) was added solid potassium t-butoxide (2.0 g, 18 mmol) and the mixture was heated at reflux for 1 h under a nitrogen atmosphere. The reaction was cooled to room temperature and compound 7 in THF was added in portions until monitoring by TLC analysis showed compound 7 was converted into a product. Water was added and the product extracted into EtOAc. The extract was dried and concentrated to give an oil which was purified by flash column chromatography (silica gel eluted with 15-35% EtOAc in hexanes) to give product 8 as a viscous oil (40 mg, 62%): IR v$_{max}$ 2928, 1698, 1448 cm$^{-1}$; $^1$H NMR (CDCl$_3$) δ 5.60 (m, 1H), 5.05 (m, 2H), 4.66 (apparent q, 2H, J=7.1 Hz), 3.77 (s, 1H), 3.38 (s, 3H), 3.35 (s, 1H), 3.30 (s, 3H), 2.45 (m, 1H), 2.25 (m, 1H), 2.05 (s, 3H), 0.83 (s, 3H), 0.77 (m, 1H); $^{13}$C NMR (CDCl$_3$) δ 212.7, 138.7, 115.6, 95.3, 79.0, 73.5, 63.0, 57.2, 56.6, 55.5, 55.4, 55.1, 39.7, 36.3, 35.7, 35.6, 34.8, 32.0, 30.4, 29.7, 28.2, 28.0, 25.1, 23.0, 13.2.

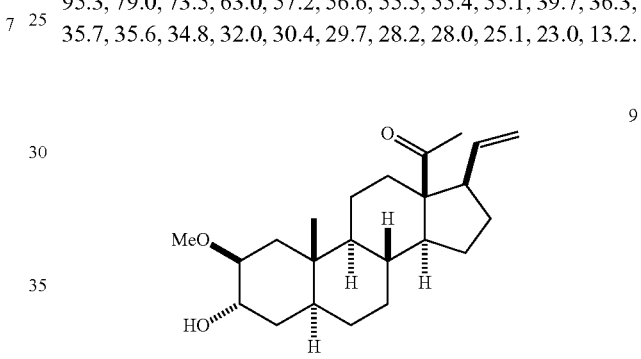

(KK-140)

1-[(2β,3α,5α)-3-Hydroxy-2-Methoxy-18-norpregn-20-en-13-yl]ethanone (9, KK-140)

Compound 8 (55 mg, 0.14 mmol) in THF (5 mL) and 6 N HCl (2 mL) was stirred at room temperature for 8 h. The solution was made basic with aqueous NaHCO$_3$ and the product extracted into CH$_2$Cl$_2$. The extract was washed with brine, dried and concentrated to give an oil. The oil was heated at 150° C. under vacuum for 1 h to remove traces of 4-chlorobutanol and the crude product was purified by flash column chromatography (silica gel eluted with 20-40% EtOAc in hexanes) to give compound 9 as a white solid (38 mg, 78%): mp 155-157° C.; [α]$_D^{23}$ −6.0 (c 0.05, CHCl$_3$); IR v$_{max}$ 3369, 2930, 2859, 1694, 1445, 1356, 1242 cm$^{-1}$; $^1$H NMR (CDCl$_3$) δ 5.62 (m, 1H), 5.05 (m, 2H), 3.94 (b s, 1H), 3.32 (b s, 1H), 3.31 (s, 3H), 2.46 (m, 1H), 2.26 (m, 1H), 2.05 (s, 3H), 0.82 (s, 3H); $^{13}$C NMR (CDCl$_3$) δ 212.7, 138.6, 115.6, 80.6, 68.2, 63.0, 57.2, 56.7, 55.5, 55.0, 39.1, 36.0, 35.6, 35.6, 34.7, 32.1, 32.0, 30.3, 28.2, 27.9, 25.1, 23.0, 13.2. Anal. (C$_{23}$H$_{36}$O$_3$): C, 76.62%; H, 10.06%. Found: C, 76.66%; H, 10.02%.

Scheme 2
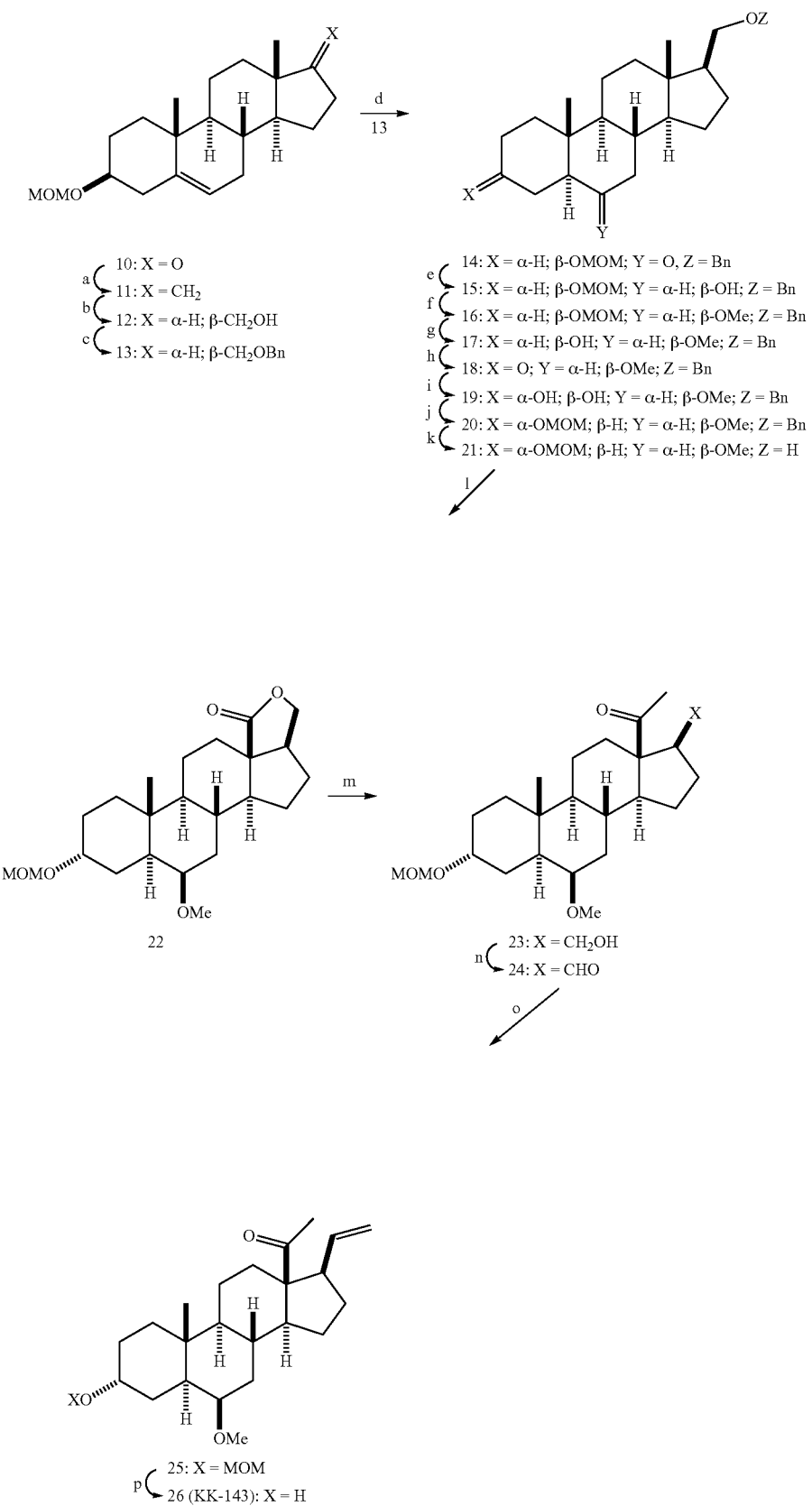

In accordance with Scheme 2, the following compounds were prepared, using methods generally known in the art and as outlined below.

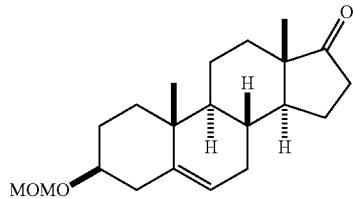

(3β)-3-(Methoxymethoxy)-androst-5-en-17-one (10)

Previously reported compound 10 (6.64 g) was prepared by the procedure described for the preparation of compound 3 from compound 2 (see Kaji, et al., "Synthesis of 3-epi-6,7-dideoxyxestobergsterol A," Chem. & Pharm. Bulletin, Vol. 48(10), pages 1480-1483 (2000)).

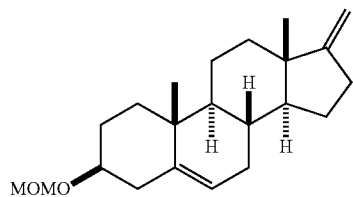

(3β)-3-(Methoxymethoxy)-17-methylene-androstane (11)

To a stirred suspension of methyltriphenylphosphonium bromide (21.40 g, 60 mmol) in THF (160 mL) was added solid potassium t-butoxide (6.5 g, 58 mmol) and the mixture was heated at reflux for an hour under nitrogen atmosphere. A THF solution (60 mL) of compound 10 (6.64 g, 20 mmol) was added using a syringe and refluxing was continued for 3 h. After cooling to room temperature, water was added and the product extracted into EtOAc. The extract was dried and concentrated to give an oil which was purified by flash column chromatography (silica gel eluted with 2-20% EtOAc in hexanes) to give compound 11 as a white solid (6.08 g, 91%): mp 76-78° C.; IR $v_{max}$ 3067, 2939, 2851, 1655, 1465, 1437, 1372, 1213 cm$^{-1}$; $^1$H NMR (CDCl$_3$) δ 5.37 (b s, 1H), 4.69 (s, 2H), 4.64 (b s, 2H), 3.43 (m, 1H), 3.37 (s, 3H), 1.03 (s, 3H), 0.80 (s, 3H); $^{13}$C NMR (CDCl$_3$) δ 161.7, 140.8, 121.5, 100.9, 94.6, 76.8, 55.1, 54.7, 50.3, 43.8, 39.5, 37.2, 36.8, 35.5, 31.74, 31.69, 29.4, 28.9, 24.2, 20.9, 19.4, 18.2.

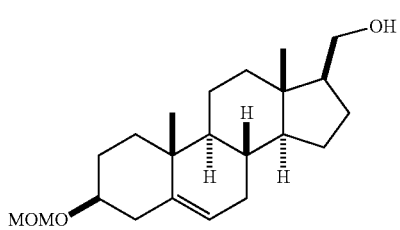

(3β,17β)-3-(Methoxymethoxy)-androst-5-ene-17-methanol (12)

To a solution of compound 11 (6 g, 18 mmol) in THF (40 mL) was added 9-BBN (64 mL, 0.5 M solution in THF) in THF and reaction was stirred at room temperature for 15 h. After cooling to 0° C., 30% hydrogen peroxide (50 mL) and 3 M aqueous NaOH (50 mL) were added and stirring was continued at room temperature for 2 h. Water (250 mL) was added and the product was extracted into Et$_2$O. The extract was washed with brine, dried and concentrated to give a viscous liquid which was purified by column chromatography (silica gel eluted with 20-35% EtOAc in hexanes to give compound 12 as a white solid (5.26 g, 84%): mp 102-105° C.; IR $v_{max}$ 3325, 1448, 1379 cm$^{-1}$; $^1$H NMR (CDCl$_3$) δ 5.35 (b s, 1H), 4.68 (s, 2H), 3.71 (dd, 1H, J=10.5 Hz, J=7.0 Hz), 3.53 (dd, 1H, J=10.5 Hz, J=7.5 Hz), 3.42 (m, 1H), 3.36 (s, 3H), 1.01 (s, 3H), 0.65 (s, 3H); $^{13}$C NMR (CDCl$_3$) δ 140.7, 121.6, 94.6, 76.9, 64.5, 56.2, 55.1, 52.9, 50.3, 41.6, 39.5, 38.5, 37.2, 36.7, 31.9, 31.5, 28.8, 25.5, 24.6, 20.7, 19.3, 12.6.

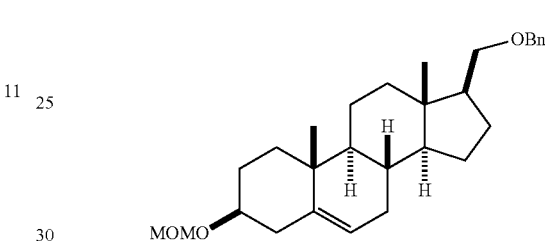

(3β,17β)-17-(Benzyloxymethyl)-3-methoxymethoxy-androst-5-ene (13)

NaH (5.7 g, 143 mmol, 60% suspension in mineral oil), compound 12 (5 g, 14.3 mmol) and benzyl bromide (5 mL, 43 mmol) in THF (150 mL) was heated at reflux for 12 h. After cooling to 0° C., excess sodium hydride was quenched by careful addition of MeOH. Water (200 mL) was added and the product extracted into EtOAc. The extract was dried and concentrated to give an oil. The excess benzyl bromide was removed at 150° C. under high vacuum and the product was purified by flash column chromatography (silica gel eluted with hexanes followed by 10-20% EtOAc in hexanes) to give compound 13 as a white solid (5.7 g, 91%): mp 75-76° C.; IR $v_{max}$ 2937, 1453, 1366, 1212 cm$^{-1}$; $^1$H NMR (CDCl$_3$) δ 7.28-2.20 (m, 5H), 5.21 (b s, 1H), 4.63 (s, 2H), 4.43 (apparent q, 2H, J=11.1 Hz), 4.47 (dd, 1H, J=10.5 Hz, J=7.0 Hz), 3.37 (m, 3H), 3.31 (s, 3H), 3.30 (m, 1H), 0.96 (s, 3H), 0.56 (s, 3H); $^{13}$C NMR (CDCl$_3$) δ 140.7, 138.8, 128.3 (2×C), 127.4 (2×C), 127.3, 121.6, 94.7, 76.9, 73.0, 72.1, 56.1, 55.2, 50.4, 49.9, 41.7, 39.5, 38.4, 37.2, 36.8, 32.0, 31.6, 28.9, 25.9, 24.7, 20.8, 19.4, 12.3.

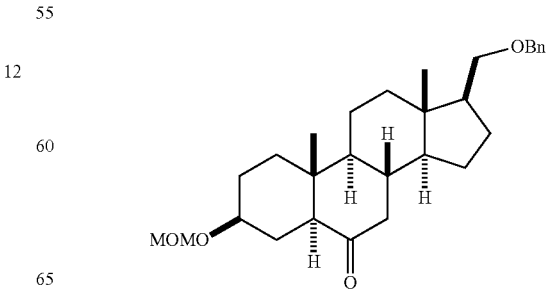

(3β,5α,17β)-17-(Benzyloxymethyl)-3-(methoxymethoxy)-androstan-6-one (14)

To a solution of compound 13 (5.6 g, 12.8 mmol) in THF (45 mL) was added BH$_3$.THF (26 mL, 1 M solution in THF) the reaction was stirred at 0° C. for 3 h. Then 30% hydrogen peroxide (35 mL) and 5 M aqueous NaOH (35 mL) was carefully added at 0° C. and stirring was continued at room temperature for 3 h. Water (200 mL) was added and the extracted into EtOAc. The extract was washed with brine, dried and concentrated to give a viscous liquid. The crude product was purified by flash column chromatography (silica gel eluted with 20-35% EtOAc in hexanes) to give a mixture of the 5α-reduced 6α-alcohol and the 5β-reduced 6β-alcohol (4.7 g, 80%) which was oxidized immediately without any further characterization.

To a solution of the hydroboration products (4.7 g, 10.3 mmol) in CH$_2$Cl$_2$ (100 mL) was added pyridinium chlorochromate (4.44 g, 20.6 mmol) and the reaction was stirred at room temperature for 4 h. Hexane (30 mL) was added and the supernatant liquid was transferred to a silica gel column and eluted with 20% EtOAc in hexanes to give mixture of the 6α/6β-ketones as a white solid. The ketone mixture and potassium carbonate (2 g) in MeOH (20 mL) was heated at reflux for 3 h, then cooled to room temperature and diluted with water (100 mL). The product was extracted first with Et$_2$O and then with EtOAc. The combined organic layers were washed with brine, dried and concentrated to give a colorless viscous liquid which was purified by column chromatography (silica gel eluted with 25% EtOAc in hexanes) to give compound 14 as a colorless liquid (4.2 g, 90%): IR v$_{max}$ 2944, 1711, 1469, 1453, 1366, 1254, 1209 cm$^{-1}$; $^1$H NMR (CDCl$_3$) δ 7.36-7.20 (m, 5H), 4.70 (apparent q, 2H, J=9.8 Hz), 4.53 (apparent q, 2H, J=12.1 Hz), 3.53 (m, 2H), 3.79 (s, 3H), 3.78 (m, 1H), 2.32 (dd, 1H, J=12.9 Hz, J=4.3 Hz), 2.20 (dd, 1H, J=12.2 Hz, J=2.4 Hz), 0.78 (s, 3H), 0.63 (s, 3H); $^{13}$C NMR (CDCl$_3$) δ 210.7, 138.6, 128.2, 127.4, 127.3, 94.3, 75.1, 73.0, 71.9, 56.7, 56.1, 55.1, 54.1, 49.8, 46.7, 42.3, 41.1, 38.1, 37.6, 36.7, 28.1, 26.9, 25.5, 24.3, 21.2, 13.1, 12.4.

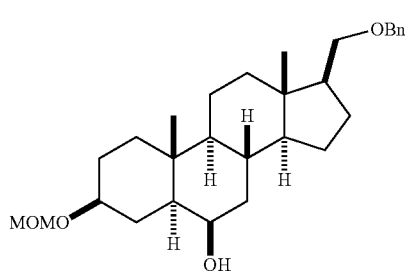

(3β,5α,6β,17β)-17-(Benzyloxymethyl)-3-(methoxymethoxy)-androstan-6-ol (15)

To a cold solution (0° C.) of compound 14 (3.2 g, 7 mmol) in THF (15 mL) was added LiAlH$_4$ (2 M in THF, 7 mL) and the reaction was stirred at room temperature for 2 h. Then Et$_2$O (100 mL) was added and water (1.5 mL added dropwise) and stirring was continued for 15 min. Aqueous 5 M NaOH (1.5 mL) was then added and after stirring for another 15 min, aqueous 5 M NaOH (2 mL) was again added and stirring continued for another 30 min. The supernatant was removed and dried and concentrated to give an oil which was purified by flash column chromatography (silica gel eluted with 20-40% EtOAc in hexanes) to give compound 15 (2.9 g, 90%) as an oil: IR v$_{max}$ 3479, 2934, 1453, 1365, 1209 cm$^{-1}$; $^1$H NMR (CDCl$_3$) δ 7.36-7.20 (m, 5H), 4.68 (apparent q, 2H, J=7.1 Hz), 4.68 (apparent q, 2H, J=12.1 Hz), 3.78 (b s, 1H), 3.51 (m, 2H), 3.36 (s, 3H), 3.35 (m, 1H), 1.02 (s, 3H), 0.62 (s, 3H); $^{13}$C NMR (CDCl$_3$) δ 138.8, 128.2, 127.4, 127.3, 94.5, 76.6, 73.0, 72.2, 71.9, 55.6, 55.1, 54.5, 50.1, 47.4, 42.0, 39.6, 38.5, 35.6, 32.4, 30.1, 28.7, 25.9, 24.6, 20.7, 15.7, 12.6.

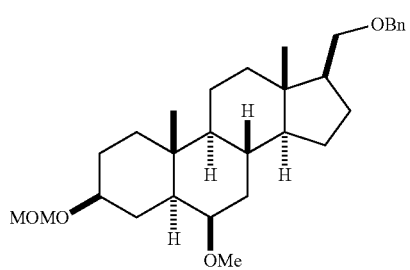

(3β,5α,6β,17β)-17-(Benzyloxymethyl)-6-methoxy-3-(methoxymethoxy)-androstane (16)

NaH (5.7 g, 143 mmol, 60% suspension in mineral oil) and compound 15 (2.51 g, 5.5 mmol) and methyl iodide (10 mL) in THF (100 mL) was heated at 60° C. for 14 h. The reaction was cooled to 0° C. and the excess NaH was quenched by careful addition of MeOH. Water (150 mL) was added and the product extracted into EtOAc. The extract was dried and concentrated to give an oil which was purified by flash column chromatography (silica gel eluted with hexanes followed by 10-15% EtOAc in hexanes) to give compound 16 as an oil (2.38 g, 92%): IR v$_{max}$ 2932, 1454, 1366 cm$^{-1}$; $^1$H NMR (CDCl$_3$) δ 7.30-7.20 (m, 5H), 4.63 (apparent q, 2H, J=7.0 Hz), 4.43 (s, 2H), 3.47 (m, 2H), 3.32 (s, 3H), 3.31 (m, 1H), 3.19 (s, 3H), 3.12 (s, 1H), 0.90 (s, 3H), 0.57 (s, 3H); $^{13}$C NMR (CDCl$_3$) δ 138.9, 128.2 (2×C), 127.4 (2×C), 127.3, 94.4, 81.3, 73.0, 72.2, 57.5, 55.6, 55.1, 54.7, 50.1, 47.8, 42.1, 38.6, 38.4, 36.0, 34.7, 32.7, 30.5, 28.7, 26.0, 24.7, 20.7, 15.4 (2×C), 12.6.

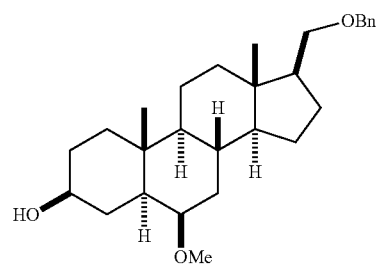

(3β,5α,6β,17β)-17-(Benzyloxymethyl)-6-methoxy-androstan-3-ol (17)

Compound 16 (2.3 g, 4.9 mmol) in MeOH (15 mL) and aqueous 6 N HCl (6 mL) was stirred at room temperature for 8 h. The reaction was made basic with aqueous NaHCO$_3$ and the product extracted into CH$_2$Cl$_2$. The extract was washed with brine, dried and concentrated to give an oil which was purified by flash column chromatography (silica gel eluted with 30-40% EtOAc in hexanes) to give compound 17 as an oil (2.0 g, 100%). IR $v_{max}$ 3369, 2931, 1454, 1366 cm$^{-1}$; $^1$H NMR (CDCl$_3$) δ 7.30-7.20 (m, 5H), 4.51 (apparent q, 2H, J=12.0 Hz), 3.55 (m, 2H), 3.36 (m, 1H), 3.27 (s, 3H), 3.20 (s, 1H), 0.98 (s, 3H), 0.66 (s, 3H); $^{13}$C NMR (CDCl$_3$) δ 138.6, 128.1 (2×C), 127.3 (2×C), 127.2, 81.2, 72.8, 72.0, 71.5, 57.3, 55.5, 54.5, 49.9, 47.6, 41.9, 38.4, 38.3, 35.6, 35.5, 34.5, 32.3, 30.3, 25.8, 24.5, 20.6, 15.3, 12.5.

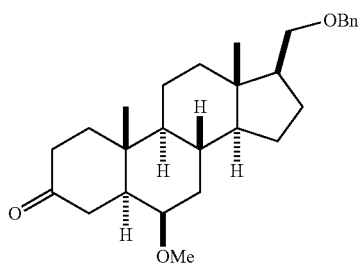

(5α,6β,17β)-17-(Benzyloxymethyl)-6-methoxy-androstan-3-one (18)

Compound 17 (1.92 g, 4.5 mmol) was dissolved in acetone (20 mL) at 0° C. and Jones reagent was added until an orange color persisted. The excess Jones reagent was consumed by adding few drops of 2-propanol. Water (100 mL) was added and the product extracted into EtOAc. The extract was washed with brine, dried and concentrated to give an oil which was purified by flash column chromatography (silica gel eluted with 15-25% EtOAc in hexanes) to give compound 18 as a viscous liquid (1.82 g, 95%): IR $v_{max}$ 2935, 1711, 1453 cm$^{-1}$; $^1$H NMR δ (CDCl$_3$) 7.30-7.20 (m, 5H), 4.51 (apparent q, 2H, J=12.1 Hz), 3.56 (dd, 1H, J=9.4 Hz, J=7.0 Hz), 3.39 (dd, 1H, J=9.4 Hz, J=7.0 Hz), 3.26 (s, 3H), 3.15 (s, 1H), 2.87 (t, 1H, J=14.4 Hz), 2.47-2.28 (m, 2H), 1.15 (s, 3H), 0.68 (s, 3H); $^{13}$C NMR δ 213.3, 138.7, 128.2 (2×C), 127.39 (2×C), 127.3, 79.9, 73.0, 72.1, 57.3, 55.4, 54.0, 50.0, 49.1, 42.1, 42.0, 39.6, 38.4, 38.1, 35.9, 34.0, 30.3, 25.9, 24.6, 20.9, 14.6, 12.6.

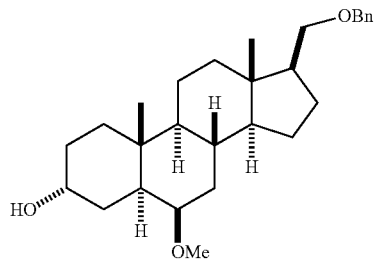

(3α,5α,6β,17β)-17-(Benzyloxymethyl)-6-methoxy-androstan-3-ol (19)

To a cold solution (−78° C.) of compound 19 (1.7 g, 4 mmol) in THF was added 1M K-Selectride in THF (4.5 mmol) and the reaction was stirred at −78° C. for 2 h. A few drops acetone was added to consume the excess K-Selec-tride and the reaction was brought to 0° C. Then 30% hydrogen peroxide (15 mL) and 3 M aqueous NaOH (15 mL) were added to the cold solution and stirring was continued at room temperature for 2 h. Water (100 mL) was added and the product was extracted into EtOAc. The extract was washed with brine, dried and concentrated to give a viscous liquid which was purified by flash column chromatography (silica gel eluted with 20-35% EtOAc in hexanes to give the desired alcohol as an oil (1.28 g, 76%): IR $v_{max}$ 3369, 2931, 1454, 1367, 1265 cm$^{-1}$; $^1$H NMR (CDCl$_3$) δ 7.35-7.25 (m, 5H), 4.50 (apparent q, 2H, J=12.0 Hz), 4.16 (s, 1H), 3.54 (dd, 1H, J=9.0 Hz, J=6.7 Hz), 3.39 (dd, 1H, J=9.0 Hz, J=7.0 Hz), 3.24 (s, 3H), 3.13 (s, 1H), 0.93 (s, 3H), 0.63 (s, 3H); $^{13}$C NMR (CDCl$_3$) δ 138.7, 128.2 (2×C), 127.4 (2×C), 127.3, 81.4, 73.0, 72.2, 67.0, 57.2, 55.6, 54.6, 50.0, 42.1, 42.0, 38.5, 36.4, 34.3, 33.7, 33.1, 30.4, 29.0, 25.9, 24.6, 20.6, 20.3, 14.4, 12.6.

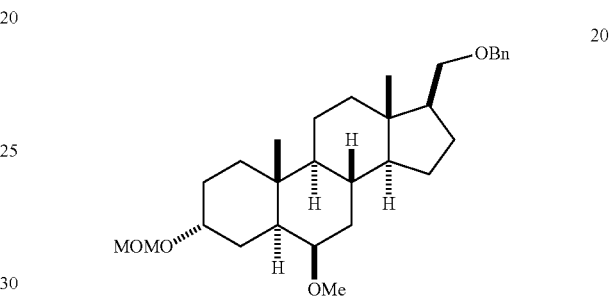

(3α,5α,6β,17β)-17-(Benzyloxymethyl)-6-methoxy-3-(methoxymethoxy)-androstane (20)

Compound 19 (1.2 g, 2.83 mmol), Hunig's base (1.75 mL, 10 mmol), chloromethyl methyl ether (0.45 mL, 6 mmol) in CH$_2$Cl$_2$ (8 mL) was stirred at room temperature for 12 h. Aqueous NaHCO$_3$ (5%, 10 mL) was added and the product extracted into CH$_2$Cl$_2$. The extract was dried and concentrated to give an oil which was purified by flash column chromatography (silica gel eluted with 15% EtOAc in hexanes) to give compound 20 as a colorless oil (1.29 g, 97%): IR $v_{max}$ 2930, 1588, 1454, 1366, 1200 cm$^{-1}$; $^1$H NMR (CDCl$_3$) δ 7.35-7.25 (m, 5H), 4.70 (apparent q, 2H, J=6.7 Hz), 4.53 (apparent q, 2H, J=12.0 Hz), 3.96 (s, 1H), 3.56 (dd, 1H, J=9.0 Hz, J=7.1 Hz), 3.41 (s, 3H), 3.40 (m, 1H), 3.28 (s, 3H), 3.18 (s, 1H), 0.99 (s, 3H), 0.68 (s, 3H); $^{13}$C NMR (CDCl$_3$) δ 138.8, 128.2 (2×C), 127.3 (2×C), 127.2, 94.4, 81.4, 72.9, 72.2, 72.0, 57.2, 55.6, 55.1, 54.6, 50.0, 42.8, 42.0, 38.5, 36.2, 34.4, 34.3, 31.1, 30.4, 26.3, 25.9, 24.6, 20.2, 14.6, 12.6.

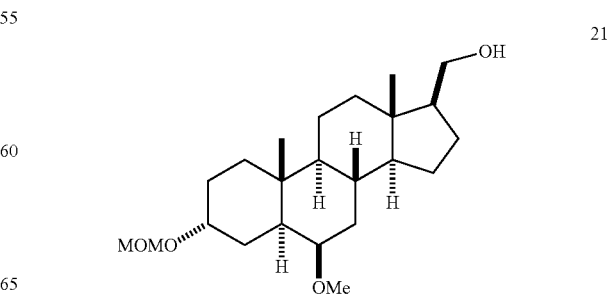

(3α,5α,6β,17β)-6-Methoxy-3-(methoxymethoxy)-androstane-17-methanol (21)

Compound 20 (941 mg, 2 mmol), 5% Pd—C in EtOAc was treated with $H_2$ (60 psi) in a Parr hydrogenator for 14 h. The Pd—C was removed and the product purified by flash column chromatography (silica gel eluted with 50% EtOAc in hexanes) to give compound 21 as a colorless liquid (730 mg, 96%): IR $v_{max}$ 3369, 2930, 1591, 1455 cm$^{-1}$; $^1$H NMR (CDCl$_3$) δ 4.67 (apparent q, 2H, J=7.0 Hz), 3.92 (t, 1H, J=2.7 Hz), 3.73 (m, 1H), 3.55 (m, 1H), 3.37 (s, 3H), 3.24 (s, 3H), 3.14 (s, 1H), 0.95 (s, 3H), 0.67 (s, 3H); $^{13}$C NMR (CDCl$_3$) δ 94.5, 81.5, 72.1, 64.7, 57.3, 55.8, 55.2, 54.6, 53.1, 42.8, 42.0, 38.8, 36.3, 34.5, 34.3, 31.2, 30.3, 26.3, 25.5, 24.6, 20.3, 14.7, 12.7.

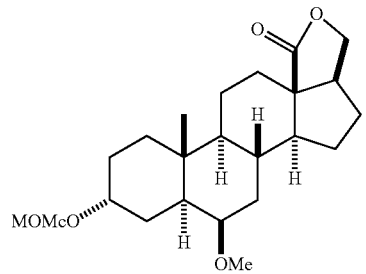

22

(3α,5α,6β,17β)-17-Hydroxymethyl-6-methoxy-3-(methoxymethoxy)-androstan-18-oic acid, γ-lactone (22)

Compound 22 (210 mg, 48%) was prepared as an oil from compound 21 using the procedure described for the preparation of compound 5 from compound 4. Compound 22 had: IR $v_{max}$ 2933, 1757, 1591, 1455, 1369 cm$^{-1}$; $^1$H NMR (CDCl$_3$) δ 4.65 (apparent q, 2H, J=6.7 Hz), 4.32 (dd, 1H, J=9.0 Hz, J=5.5 Hz), 4.07 (d, 1H, J=9.4 Hz), 3.91 (t, 1H, J=2.8 Hz), 3.36 (s, 3H), 3.21 (s, 3H), 3.13 (apparent q, 1H, J=2.8 Hz), 2.54 (m, 1H), 2.30 (m, 1H), 1.00 (s, 3H); $^{13}$C NMR (CDCl$_3$) δ 179.3, 94.5, 80.9, 72.2, 72.1, 57.0, 55.2, 55.1, 53.7, 53.4, 45.3, 42.8, 36.3, 34.6, 34.4, 31.7, 31.3, 31.1, 29.1, 27.3, 26.3, 19.9, 14.6.

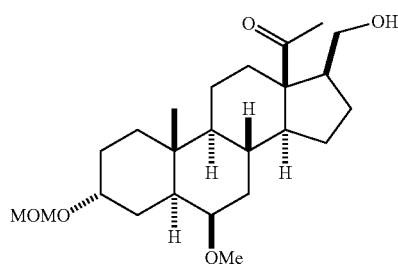

23

1-[(3α,5α,6β,17β)-17-Hydroxymethyl-6-methoxy-3-(methoxymethoxy)-18-norandrostan-13-yl]ethanone (23)

Compound 23 (110 mg, 50%) was prepared as an oil from compound 22 using the procedure described for the preparation of compound 6 from compound 5. Compound 23 had: IR $v_{max}$ 3446, 2931, 2874, 1696, 1593, 1462, 1368 cm$^{-1}$; $^1$H NMR (CDCl$_3$) δ 4.65 (apparent q, J=6.6 Hz), 3.91 (t, 1H, J=2.7 Hz), 3.60 (m, 2H), 3.37 (s, 3H), 3.23 (s, 3H), 3.13 (br s, 1H), 2.70 (t d, 1H, J=12.7 Hz, J=3.2 Hz), 2.22 (s, 3H), 0.83 (s, 3H); $^{13}$C NMR (CDCl$_3$) δ 213.7, 94.5, 81.0, 64.0, 61.0, 57.4, 57.0, 55.1, 54.9, 53.1, 42.8, 36.3, 36.2, 34.4, 33.9, 31.5, 31.1, 30.4, 26.2, 26.0, 25.0, 22.9, 14.7.

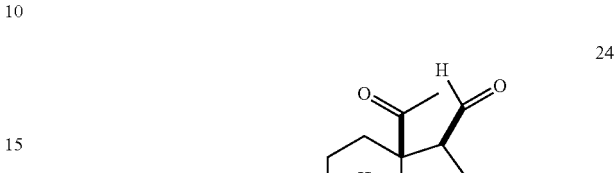

24

(3α,5α,6β,17β)-13-Acetyl-6-methoxy-3-(methoxymethoxy)-8-norandrostan-17-carboxaldehyde (24)

Compound 24 was prepared from compound 23 using the procedure described for the preparation of compound 7 from compound 6. Compound 24 was immediately converted without characterization ($^1$H NMR confirmed the presence of the aldehyde group) to compound 25.

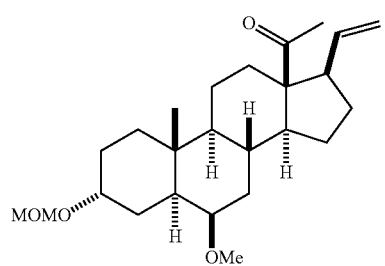

25

1-[(3α,5α,6δ)-6-Methoxy-3-(methoxymethoxy)-18-norpregn-20-en-13-yl]ethanone (25)

Compound 25 (80 mg, 78%) was obtained as an oil from compound 24 using the procedure described for the preparation of compound 8 from compound 7. Compound 25 had: IR $v_{max}$ 2931, 1699, 1462, 1358, 1195, 1450 cm$^{-1}$; $^1$H NMR (CDCl$_3$) δ 5.63 (m, 1H), 5.07 (m, 2H), 4.66 (apparent q, J=6.7 Hz), 3.91 (b s, 1H), 3.23 (s, 3H), 3.23 (s, 3H), 3.13 (b s, 1H), 2.45 (m, 1H), 2.28 (m, 1H), 2.10 (m, 1H), 2.06 (s, 3H), 0.84 (s, 3H); $^{13}$C NMR (CDCl$_3$) δ 212.4, 138.6, 115.7, 94.5, 81.0, 72.0, 62.9, 57.0, 56.9, 55.14, 55.07, 55.0, 42.8, 36.2, 34.7, 34.5, 33.9, 31.5, 31.1, 30.4, 28.2, 26.3, 25.2, 22.7, 14.7.

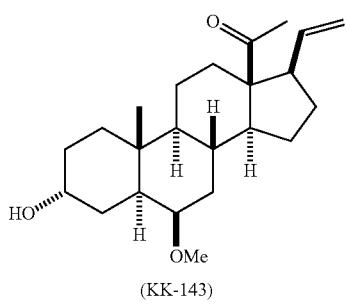

(KK-143)

1-[(3α,5α,6β)-3-Hydroxy-6-methoxy-18-norpregn-20-en-13-yl]ethanone (26, KK-143)

Compound 26 (33 mg, 77%) was prepared from compound 25 as a white solid using the procedure described for the preparation of compound 9 from compound 8. Compound 26 had: mp 158-160° C.; $[\alpha]_D^{23}$ −49 (c 0.065, CHCl$_3$); IR v$_{max}$ 3308, 2936, 2867, 1698, 1430 cm$^{-1}$; $^1$H NMR (CDCl$_3$) δ 5.62 (m, 1H), 5.06 (m, 2H), 4.13 (t, 1H, J=2.8 Hz), 3.22 (s, 3H), 3.12 (b s, 1H), 2.44 (m, 1H), 2.29 (m, 1H), 2.10 (m, 1H), 2.05 (s, 3H), 0.81 (s, 3H); $^{13}$C NMR (CDCl$_3$) δ 212.4, 138.6, 115.7, 80.9, 66.8, 62.9, 57.0, 56.9, 55.1, 42.1, 36.4, 34.7, 33.9, 33.8, 33.2, 31.4, 30.3, 29.0, 28.1, 25.2, 22.7, 14.5. HRMS (FAB) Calcd for C$_{23}$H$_{36}$O$_3$Na: 283.2562. Found: 283.2565.

Scheme 3

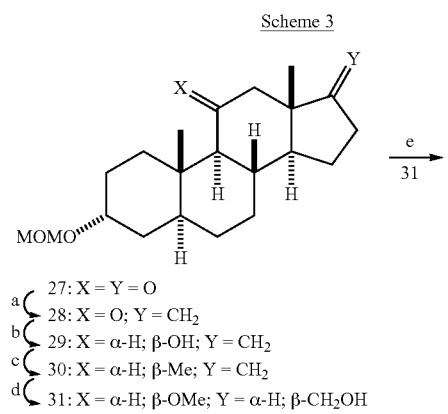

a { 27: X = Y = O
b { 28: X = O; Y = CH$_2$
c { 29: X = α-H; β-OH; Y = CH$_2$
d { 30: X = α-H; β-Me; Y = CH$_2$
  { 31: X = α-H; β-OMe; Y = α-H; β-CH$_2$OH

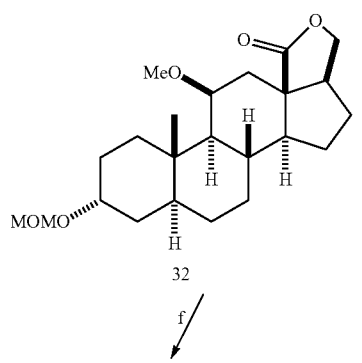

32

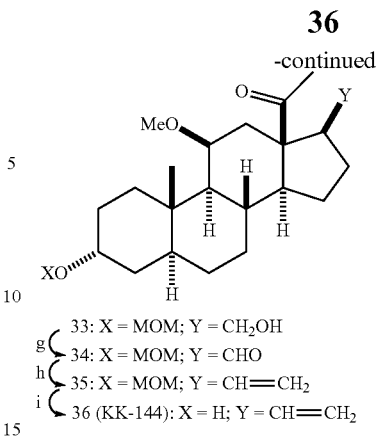

g { 33: X = MOM; Y = CH$_2$OH
h { 34: X = MOM; Y = CHO
i { 35: X = MOM; Y = CH=CH$_2$
  { 36 (KK-144): X = H; Y = CH=CH$_2$

In accordance with Scheme 3, the following compounds were prepared, using methods generally known in the art and as outlined below.

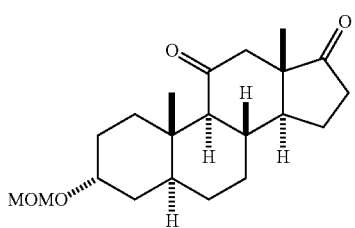

(3α,5α)-3-(Methoxymethoxy)-androstane-11,17-dione (27)

Compound 27 was prepared as described previously (see Bandyopadhyaya, et al., "Neurosteroid analogues. 15. A comparative study of the anesthetic and GABAergic actions of alphaxalone, Δ16-alphaxalone and their corresponding 17-carbonitrile analogues," Bioorganic & Medicinal Chemistry Letters, Vol. 20(22), pages 6680-6684 (2010)).

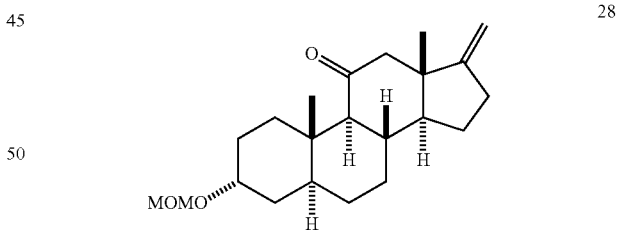

(3α,5α)-3-(Methoxymethoxy)-17-methylene-androstan-11-one (28)

Compound 28 (810 mg, 78%) was prepared from compound 27 as a low melting solid using the procedure described for the preparation of compound 11 from compound 10. Compound 28 had: IR v$_{max}$ 2924, 1702, 1656, 1454, 1374 cm$^{-1}$; $^1$H NMR (CDCl$_3$) δ 4.63 (m, 4H), 3.81 (b s, 1H), 3.35 (s, 3H), 2.6-2.19 (m, 4H), 1.02 (s, 3H), 0.72 (s, 3H); $^{13}$C NMR (CDCl$_3$) δ 210.8, 158.7, 102.1, 94.4, 71.3, 64.7, 55.1, 54.2, 53.8, 47.9, 39.6, 36.6, 35.5, 33.2, 32.3, 31.5, 29.6, 27.9, 25.9, 23.8, 19.3, 11.1.

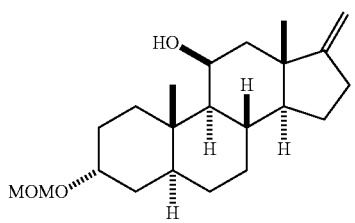

(3α,5α,11β)-3-(Methoxymethoxy)-17-methylene-androstan-11-ol (29)

To a cold solution (0° C.) of compound 28 (693 mg, 2 mmol) in Et$_2$O (15 mL) was added LiAlH$_4$ (2 M in THF, 4 mL) and the reaction was stirred at room temperature for 2 h. Then Et$_2$O (50 mL) and water (0.5 mL) were added and stirring was continued for 15 min. Aqueous 5 M NaOH (0.5 mL) was then added and after stirring for 15 min, additional 5 M aqueous NaOH (1 mL) was added and stirring continued for another 30 min. The supernatant was removed and concentrated to give an oil which was purified by flash column chromatography (silica gel eluted with 15-40% EtOAc in hexanes) to give compound 29 (570 mg, 82%) as an oil: IR $v_{max}$ 3501, 3066, 2923, 1654, 1445 cm$^{-1}$; $^1$H NMR (CDCl$_3$) δ 4.60 (m, 4H), 4.35 (b s, 1H), 3.81 (b s, 1H), 3.34 (s, 3H), 2.45 (m, 1H), 2.20 (m, 1H), 1.93 (dd, 1H, J=14.1 Hz, J=2.0 Hz), 1.02 (s, 3H), 0.97 (s, 3H), 0.81 (dd, 1H, J=10.9 Hz, J=2.7 Hz); $^{13}$C NMR (CDCl$_3$) δ 161.6, 100.3, 94.3, 71.2, 67.9, 58.3, 55.9, 55.0, 44.5, 43.1, 40.5, 36.0, 32.9, 32.4, 32.0, 31.1, 28.9, 27.9, 25.9, 23.9, 20.7, 14.4.

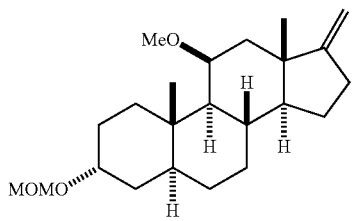

(3α,5α,11β)-11-Methoxy-3-(methoxymethoxy)-17-methylene-androstane (30)

NaH (1.6 g, 40 mmol, 60% suspension in mineral oil) and compound 29 (560 mg, 1.6 mmol) in THF (35 mL) and methyl iodide (6 mL) was heated at 60° C. for 14 h. The reaction mixture was cooled to 0° C. and the excess NaH consumed by careful addition of MeOH. Water (80 mL) was added and the product extracted into EtOAc. The extract was dried and concentrated to give an oil which was purified by flash column chromatography (silica gel eluted with hexanes followed by 10-15% EtOAc in hexanes) to give compound 30 as an oil (469 mg, 81%). IR $v_{max}$ 3067, 2920, 1655, 1456, 1369 cm$^{-1}$; $^1$H NMR (CDCl$_3$) δ 4.65 (apparent q, 2H, J=6.7 Hz), 4.58 (s, 2H), 3.82 (b s 1H), 3.70 (b s, 1H), 3.36 (s, 3H), 3.23 (s, 3H), 2.46 (m, 1H), 2.30-2.17 (m, 2H), 0.98 (s, 3H), 0.92 (s, 3H); $^{13}$C NMR (CDCl$_3$) δ 162.1, 100.0, 94.4, 77.1, 71.5, 58.5, 56.2, 55.3, 55.1, 43.5, 40.6, 36.2, 36.1, 33.1, 32.6, 32.3, 31.7, 29.1, 28.0, 26.0, 23.9, 19.4, 14.1.

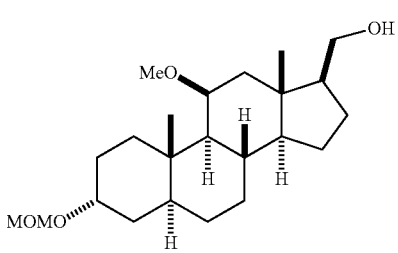

(3α,5α,11β,17β)-11-Methoxy-3-(methoxymethoxy)-androstane-17-methanol (31)

To compound 30 (450 mg, 1.24 mmol) in THF (5 mL) was added 9-BBN (6 mL, 0.5 M in THF) and the reaction was stirred at room temperature for 15 h. After cooling to 0° C., 30% hydrogen peroxide (15 mL) and 3 M aqueous NaOH (15 mL) were added and stirring was continued at room temperature for 2 h. Water (80 mL) was added and the product extracted into Et$_2$O. The extract was washed with brine, dried and concentrated to give a viscous liquid which was purified by flash column chromatography (silica gel eluted with 20-40% EtOAc in hexanes) to give compound 31 as an oil (391 mg, 83%): IR $v_{max}$ 3413, 2924, 2871, 144, 1368, 1382 cm$^{-1}$; $^1$H NMR (CDCl$_3$) δ 4.64 (apparent q, 2H, J=7.5 Hz), 3.81 (b s, 1H), 3.66 (m, 1H), 3.61 (b s, 1H), 3.51 (m, 1H), 3.35 (s, 3H), 3.18 (s, 3H), 2.31 (m, 1H), 0.96 (s, 3H), 0.78 (s, 3H); $^{13}$C NMR (CDCl$_3$) δ 94.4, 77.1, 71.5, 64.5, 58.4, 57.8, 55.4, 55.1, 53.3, 41.2, 40.5, 39.4, 36.0, 33.0, 32.6, 32.5, 31.5, 28.0, 26.0, 25.0, 24.3, 14.0, 13.5.

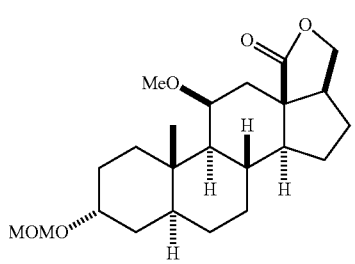

(3α,5α,11β,17β)-17-Hydroxymethyl-11-methoxy-3-(methoxymethoxy)-androstan-18-oic acid-γ-lactone (32)

Compound 32 was prepared as an oil in 34% yield from compound 31 using the procedure described for the preparation of compound 5 from compound 4. Compound 32 had:

IR ν$_{max}$ 2927, 1771, 1446, 1368, 1278 cm$^{-1}$; $^1$H NMR (CDCl$_3$) δ 4.64 (apparent q, 2H, J=6.7 Hz), 4.32 (dd, 1H, J=9.0 Hz, J=4.3 Hz), 3.99 (m, 1H), 3.82 (b s, 1H), 3.67 (b s, 1H), 3.35 (s, 3H), 3.15 (s, 3H), 2.76 (m, 1H), 2.52 (m, 1H), 2.22 (m, 1H), 2.07 (m, 1H), 1.04 (s, 3H), 0.89 (m, 2H); $^{13}$C NMR (CDCl$_3$) δ 177.7, 94.4, 75.7, 71.5, 70.4, 57.9, 55.6, 55.5, 55.0, 51.0, 46.8, 40.5, 36.1, 33.0, 32.9, 32.8, 29.9, 29.8, 27.8, 26.2, 26.0, 14.1.

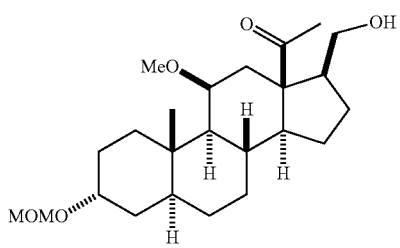

1-[(3α,5α,11β,17β)-17-Hydroxymethyl-1'-methoxy-3-(methoxymethoxy)-18-norandrostan-13-yl]ethanone (33)

Compound 33 (65 mg, 57%) was prepared as an oil from compound 32 using the procedure described for the preparation of compound 6 from compound 5. Compound 33 had: IR ν$_{max}$ 3447, 2928, 1694, 1445, 1349 cm$^{-1}$; $^1$H NMR (CDCl$_3$) δ 4.63 (apparent q, 2H, J=7.1 Hz), 3.81 (b s, 1H), 3.45-3.60 (m, 2H), 3.38 (m, 1H), 3.34 (s, 3H), 3.02 (s, 3H), 2.99 (m, 1H), 2.19 (m, 1H), 2.16 (s, 3H), 0.89 (s, 3H), 0.77 (m, 1H); $^{13}$C NMR (CDCl$_3$) δ 212.4, 94.4, 76.0, 71.4, 64.8, 59.0, 58.6, 56.7, 55.3, 55.1, 52.6, 41.7, 40.2, 35.8, 33.2, 32.9, 32.6, 32.0, 29.9, 27.9, 26.0, 25.2, 24.1, 13.7.

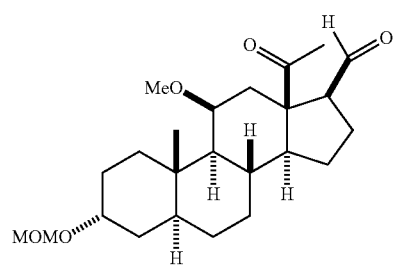

(3α,5α,11β,17β)-13-Acetyl-11-methoxy-3-(methoxymethoxy)-18-norandrostane-17-carboxaldehyde (34)

Compound 34 was prepared from compound 33 using the procedure described for the preparation of compound 7 from compound 6. Compound 34 was immediately converted without characterization to compound 35.

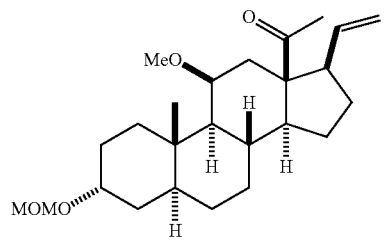

1-[(3α,5α,11β)-11-Methoxy-3-(methoxymethoxy)-18-norpregn-20-en-13-yl]ethanone (35)

Compound 35 (40 mg, 66%) was obtained as an oil from compound 34 using the procedure described for the preparation of compound 8 from compound 7. Compound 35 had: IR ν$_{max}$ 2927, 1699, 1444, 1368 cm$^{-1}$; $^1$H NMR (CDCl$_3$) δ 5.71 (m, 1H), 5.03 (m, 2H), 4.65 (apparent q, 2H, J=6.7 Hz), 3.82 (b s, 1H), 3.60 (b s, 1H), 3.36 (s, 3H), 3.17 (s, 3H), 2.80 (dd, 1H, J=13.7 Hz, J=3.1 Hz), 2.21 (m, 2H), 1.95 (s, 3H), 0.89 (s, 3H), 0.75 (dd, 1H, J=11.4 Hz, J=2.8 Hz); $^{13}$C NMR (CDCl$_3$) δ 209.8, 138.9, 115.2, 94.5, 76.5, 71.5, 59.2, 57.6, 56.4, 55.1, 54.9, 40.4, 38.5, 36.0, 33.4, 32.9, 32.6, 31.6, 29.51, 28.0, 27.6, 26.1, 24.3, 13.8.

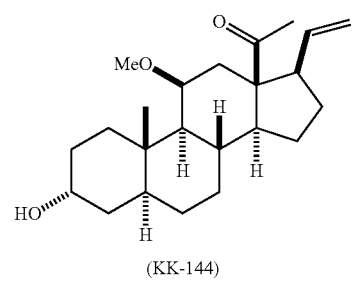

(KK-144)

1-[(3α,5α,11β)-3-Hydroxy-11-methoxy-18-norpregn-20-en-13-yl]ethanone (36, KK-144)

Compound 36 (26 mg, 85%) was prepared from compound 35 as a white solid using the procedure described for the preparation of compound 9 from compound 8. Compound 36 had: mp 127-129° C.; [α]$_D^{23}$ −32 (c 0.03, CHCl$_3$); IR ν$_{max}$ 3401, 2925, 1698, 1593, 1444 cm$^{-1}$; $^1$H NMR (CDCl$_3$) δ 5.72 (m, 1H), 5.05 (m, 2H), 4.05 (b s, 1H), 3.62 (b s, 1H), 3.18 (s, 3H), 2.82 (dd, 1H, J=14.1 Hz, J=3.6 Hz), 2.22 (m, 2H), 1.96 (s, 3H), 0.89 (s, 3H); $^{13}$C NMR (CDCl$_3$) δ 209.8, 138.9, 115.2, 76.5, 66.4, 59.9, 59.2, 57.6, 56.5, 54.9, 39.8, 38.5, 36.3, 35.3, 32.7, 32.6, 31.6, 29.5, 28.7, 27.9, 27.7, 24.4, 13.6. Anal. (C$_{23}$H$_{36}$O$_3$): C, 76.62%; H, 10.06%. Found: C, 76.68%; H, 9.93%.

Scheme 4

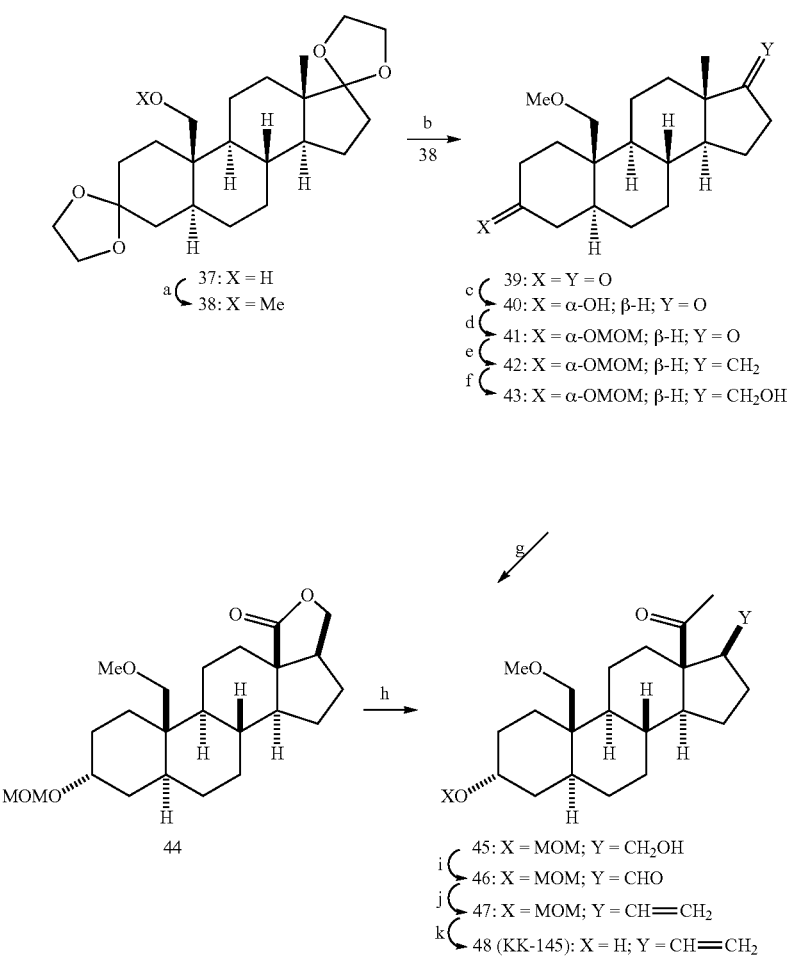

In accordance with Scheme 4, the following compounds were prepared, using methods generally known in the art and as outlined below.

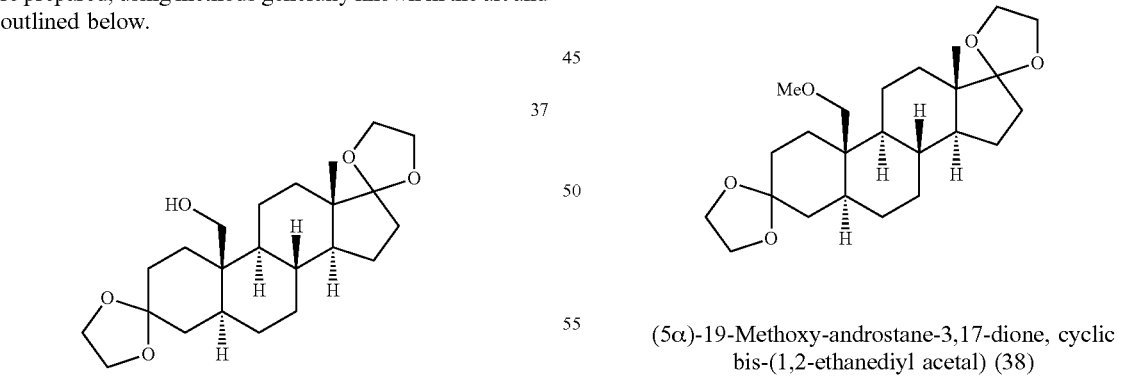

(5α)-19-Hydroxy-androstane-3,17-dione, cyclic bis-(1,2-ethanediyl acetal) (37)

Compound 37 was prepared as described previously (see, Santaniello & Caspi, "Reduction of certain steroidal 19-sulfonic esters with metal hydrides," J. of Ster. Biochem., Vol. 7(3), pages 223-227 (1976)).

(5α)-19-Methoxy-androstane-3,17-dione, cyclic bis-(1,2-ethanediyl acetal) (38)

A mixture of compound 37 (430 mg, 1.1 mmol), NaH (200 mg, 5 mmol) and THF (10 mL) was heated at reflux for 2 h under $N_2$. The reaction mixture was cooled to room temperature, and methyl iodide (2 mL, 32 mmol) was added and the mixture was stirred at room temperature for 13 h. The reaction mixture was cooled to 0° C. and excess NaH was consumed by adding MeOH (2 mL). Water (100 mL) was added and the product was extracted into EtOAc (80 mL×3). The combined organic extracts were washed with brine, dried and concentrated to give a colorless liquid. The crude product was purified by flash column chromatography (silica gel eluted with 15-20% EtOAc in hexanes) to give product 38 as a colorless liquid (440 mg, 99%): IR $v_{max}$ 2923, 1457, 1378, 1306, 1210 cm$^{-1}$; $^1$H NMR δ 3.89 (s, 4H), 3.87-3.82 (m, 4H), 3.47 (d, 1H, J=10.0 Hz), 3.39 (d, 1H, J=9.9 Hz), 3.25 (s, 3H), 0.82 (s, 3H); $^{13}$C NMR δ 119.3, 109.2, 71.0, 65.0, 64.5, 64.0, 59.0, 54.0, 50.4, 46.0, 43.8, 38.9, 38.4, 36.2, 34.1, 31.5, 31.1, 31.0 (2×C), 29.6, 28.1, 22.6, 21.7, 14.4. Anal. (C$_{24}$H$_{38}$O$_5$): C, 70.90%; H, 9.42%. Found: C, 71.17%; H, 9.53%.

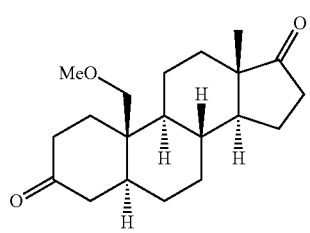

(5α)-19-Methoxy-androstane-3,17-dione (39)

A mixture of compound 38 (400 mg, 0.98 mmol), PTSA (100 mg), acetone (8 mL) and water (0.5 mL) was stirred at room temperature for 14 h. The reaction was neutralized with aqueous NaHCO$_3$ and the acetone was removed under reduced pressure. Water (80 mL) was added and the product was extracted into EtOAc (60 mL×3). The combined EtOAc extracts were dried and concentrated to give a white solid which was purified by flash column chromatography (silica gel eluted with 20-30% EtOAc in hexanes) to yield product 39 (230 mg, 73%): mp 94-96° C.; IR $v_{max}$ 2918, 1738, 1712, 1452, 1407, 1373, 1270, 1248, 1220, 1202, cm$^{-1}$; $^1$H NMR δ 3.60 (d, 1H, J=11.0 Hz), 3.57 (d, 1H, J=11.0 Hz), 3.26 (s, 3H), 2.50-0.74 (m), 0.82 (s, 3H); $^{13}$C NMR δ 220.5, 211.7, 71.7, 59.0, 53.9, 51.3, 47.6, 46.1, 44.7, 38.9, 38.5, 35.6, 35.3, 34.2, 31.5, 30.3, 28.1, 21.5, 21.3, 13.7. HRMS Calcd for (C$_{20}$H$_{30}$O$_3$): 318.2195. Found: 318.2180.

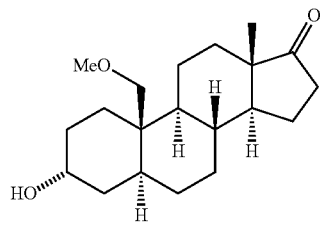

(3α,5α)-3-Hydroxy-19-methoxy-androstan-17-one (40)

A 1 M K-Selectride solution in THF (2 mL, 2 mmol, 3 eq) was added to a cold solution (−78° C.) of compound 39 (210 mg, 0.66 mmol) in THF (5 mL) and the reaction was stirred at −78° C. for 1.5 h. The reaction was stopped by adding a few drops of acetone and then allowed to warm to room temperature. 3 N aqueous NaOH (10 mL) followed by 30% aqueous H$_2$O$_2$ (10 mL) was added and the reaction was stirred at room temperature for 1.5 h. The product was extracted into EtOAc (3×60 mL) and the combined EtOAc extracts were washed with brine, dried, and concentrated to give an off-white solid which was purified by flash column chromatography (silica gel eluted with 20-40% EtOAc in hexanes). Product 40 (142 mg, 67%) had: mp 172-174° C.; IR $v_{max}$ 3436, 2921, 1738, 1453, 1406, 1372, 1248, 1203 cm$^{-1}$; $^1$H NMR δ 4.05 (b s, 1H), 3.48 (d, 1H, J=9.9 Hz), 3.38 (d, 1H, J=10.2 Hz), 3.25 (s, 3H), 2.39 (dd, 1H, J=19.3 Hz, 8.8 Hz, 1H), 2.2.10-0.70 (m), 0.84 (s, 3H); $^{13}$C NMR δ 221.5, 71.1, 66.1, 59.0, 54.6, 51.7, 47.8, 39.6, 39.2, 36.0, 35.7, 35.5, 31.8, 30.7, 29.2, 27.9, 27.1, 21.6, 21.1, 13.8. Anal. (C$_{20}$H$_{32}$O$_3$): C, 74.96%; H, 10.06%. Found: C, 74.91%; H, 9.86%.

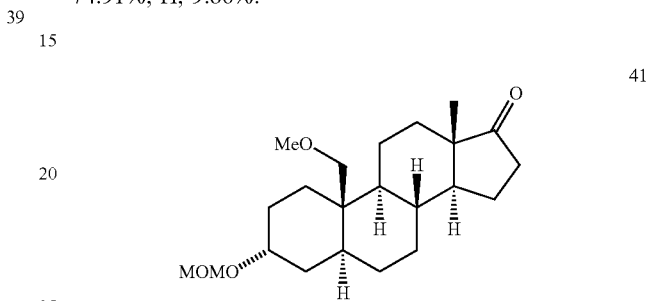

(3α,5α)-19-Methoxy-3-(methoxymethoxy)-androstan-17-one (41)

To a solution of compound 40 (800 mg, 2.5 mmol) in DCM (20 mL) was added chloromethyl methyl ether (302 mg, 3.75 mmol) and N,N-diisopropylethylamine (774 mg, 6 mmol) at room temperature. The mixture was stopped by water addition after 16 h and the product extracted into EtOAc (100 mL×2). The combined extracts were washed with brine, dried and concentrated. The residue was purified by column chromatography (silica gel eluted with 25% EtOAc in hexanes) to give product 41 as an oil (900 mg, 100%): IR $v_{max}$ 2921, 1740 cm$^{-1}$; $^1$H NMR (CDCl$_3$) δ 4.65 (dd, 1H, J=6.6 Hz, J=10.9 Hz), 3.86-3.84 (m, 1H), 3.52 (d, 1H, J=10.2 Hz), 3.43 (d, 1H, J=9.8 Hz), 3.35 (s, 3H), 3.28 (s, 3H), 0.86 (s, 3H); $^{13}$C NMR (CDCl$_3$) δ 221.4, 94.5, 71.3, 71.2, 59.1, 55.1, 54.6, 51.7, 47.9, 39.9, 39.4, 35.8, 35.5, 34.0, 31.9, 30.8, 28.0, 27.7, 26.5, 21.7, 21.2, 13.9.

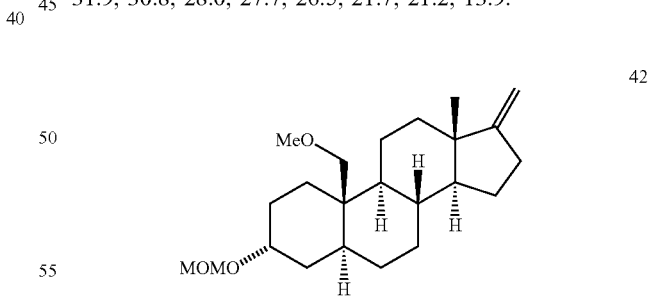

(3α,5α)-19-Methoxy-3-(methoxymethoxy)-17-methylene-androstane (42)

To a stirred suspension of methyltriphenylphosphonium bromide (7.14 g, 20 mmol) in THF (60 mL) was added solid potassium t-butoxide (2.12 g, 19 mmol) and the mixture was heated at reflux for 1 h under a nitrogen atmosphere. A THF solution (15 mL) of compound 41 (740 mg, 2.03 mmol) was added to the resulting yellow refluxing methylene triphenylphosphorane solution using a syringe. The reaction mixture was continued at reflux for 3 h. The completion of reaction was confirmed by monitoring by TLC analysis. The reaction mixture was cooled to room temperature, water was added and the product extracted into EtOAc. The extract was dried and concentrated to give an oil which was purified by column chromatography (silica gel eluted with 2-20% EtOAc in hexanes) to give compound 42 as an oil (680 mg, 92%): IR $v_{max}$ 2921, 1655, 1447, 1371, 1204 cm$^{-1}$; $^1$H NMR (CDCl$_3$) δ 4.67 (apparent q, 2H, J=6.6 Hz), 4.62 (m, 2H), 3.88 (b s, 1H), 3.49 (apparent q, 2H, J=9.8 Hz) 3.37 (s, 3H), 3.31 (s, 3H), 2.45 (m, 1H), 2.21 (m, 1H), 1.98 (m, 1H), 0.80 (s, 3H); $^{13}$C NMR (CDCl$_3$) δ 162.1, 100.6, 94.4, 71.4, 71.3, 59.1, 55.1, 54.7, 54.6, 44.2, 40.0, 39.4, 36.0, 35.9, 34.0, 31.7, 29.3, 28.2, 27.5, 26.6, 24.1, 21.9, 18.6.

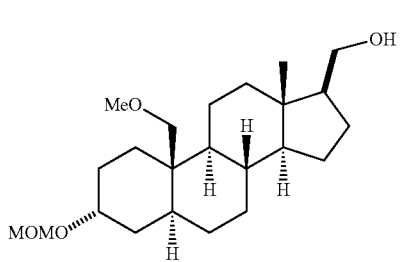

(3α,5α,17β)-19-Methoxy-3-(methoxymethoxy)-androstane-17-methanol (43)

To a solution of compound 42 (680 mg, 1.87 mmol) in THF (5 mL) was added 9-BBN (8 mL, 0.5 M solution in THF) and the reaction was stirred at room temperature for 15 h, them cooled to 0° C. 30% Hydrogen peroxide (15 mL) and 3 M aqueous NaOH (15 mL) was added to the cold solution and stirring was continued at room temperature for 2 h. Water (80 mL) was added and the product was extracted into Et$_2$O. The extract was washed with brine, dried and concentrated to give a viscous liquid which wash purified by column chromatography (silica gel eluted with 20-40% EtOAc in hexanes) to give compound 43 as an oil (620 mg, 87%): IR $v_{max}$ 3496, 2936, 1455, 1365, 1306 cm$^{-1}$; $^1$H NMR (CDCl$_3$) δ 4.65 (apparent q, 2H, J=7.0 Hz), 3.86 (b s, 1H), 3.68 (dd, 1H, J=7.5 Hz, J=4.7 Hz), 3.50 (dd, 1H, J=7.5 Hz, J=4.7 Hz), 3.46 (apparent q, 1H, J=10.2 Hz), 3.35 (s, 3H), 3.28 (s, 3H), 0.64 (s, 3H); $^{13}$C (CDCl$_3$) NMR δ 94.4, 71.4, 71.3, 64.6, 59.1, 56.2, 55.1, 54.8, 53.0, 41.9, 39.9, 39.3, 39.1, 35.6, 34.0, 31.9, 28.2, 27.6, 26.6, 25.6, 24.5, 21.7, 12.7.

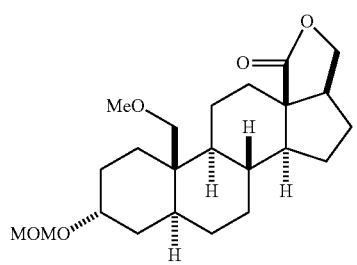

(3α,5α,17β)-17-Hydroxymethyl-19-methoxy-3-(methoxymethoxy)-androstan-18-oic acid, γ-lactone (44)

Compound 44 (110 mg, 36%) was prepared as an oil in 34% yield from compound 43 using the procedure described for the preparation of compound 5 from compound 4. Compound 44 had: IR $v_{max}$ 2924, 1757, 1445 cm$^{-1}$; $^1$H NMR (CDCl$_3$) δ 4.64 (apparent q, 2H, J=7.0 Hz), 4.30 (m, 1H), 4.06 (m, 1H), 3.86 (b s, 1H), 3.51 (apparent q, 2H, J=10.2 Hz), 3.35 (s, 3H), 3.30 (s, 3H); $^{13}$C NMR (CDCl$_3$) δ 179.6, 94.4, 72.2, 71.4, 70.4, 58.8, 55.2, 55.1, 53.6, 53.5, 45.2, 39.9, 39.4, 34.0, 33.9, 32.1, 31.9, 31.3, 27.9, 27.4, 27.3, 26.6, 21.3.

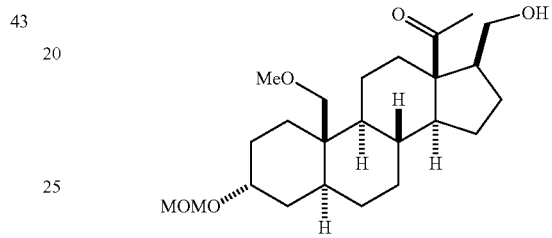

1-[(3α,5α,17β)-17-Hydroxymethyl-19-methoxy-3-(methoxymethoxy)-18-norandrostan-13-yl]ethanone (45)

Compound 45 (60 mg, 53%) was prepared as an oil from compound 45 using the procedure described for the preparation of compound 6 from compound 5. Compound 45 had: IR $v_{max}$ 3468, 2926, 2871, 1695, 1446, 1372 cm$^{-1}$; $^1$H NMR (CDCl$_3$) δ 4.65 (apparent q, 2H, J=7.1 Hz), 3.85 (b, 1H), 3.60 (m, 2H), 3.36 (s, 2H), 3.35 (s, 3H), 3.21 (s, 3H), 2.64 (m, 1H), 2.20 (s, 3H); $^{13}$C NMR (CDCl$_3$) δ 214.3, 94.4, 71.3, 70.6, 63.8, 61.0, 58.9, 57.7, 55.1, 54.8, 53.0, 39.9, 39.3, 36.5, 33.9, 31.8, 30.1, 28.0, 27.1, 26.4, 25.7, 24.9, 24.4.

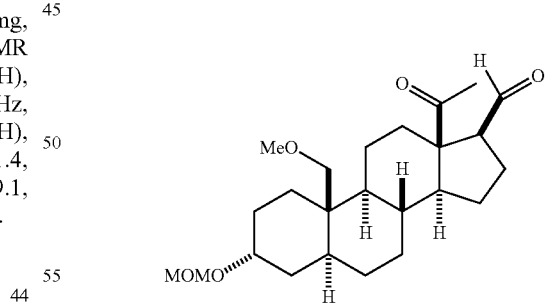

(3α,5α,17β)-13-Acetyl-19-methoxy-3-(methoxymethoxy)-18-norandrostane-17-carboxaldehyde (46)

Compound 46 was prepared from compound 45 using the procedure described for the preparation of compound 7 from compound 6. Compound 34 was immediately converted without characterization to compound 47.

47

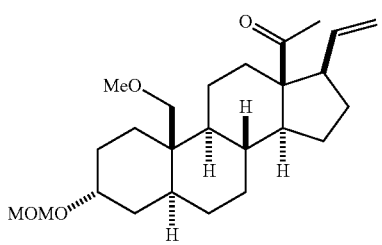

1-[(3α,5α)-19-Methoxy-3-(methoxymethoxy)-18-norpregn-20-en-13-yl]ethanone (47)

Compound 47 (30 mg, 50%) was prepared from compound 46 as an oil using the procedure described for the preparation of compound 8 from compound 7. Compound 47 had: IR $v_{max}$ 2926, 1698, 1446, 1357 cm$^{-1}$; $^1$H NMR (CDCl$_3$) δ 5.62 (m, 1H), 5.01-5.10 (m, 2H), 4.67 (apparent q, 2H, J=7.1 Hz), 3.88 (b s, 1H), 3.39 (s, 2H), 3.38 (s, 3H), 3.22 (s, 3H), 2.42 (m, 1H), 2.26 (m, 1H), 2.05 (s, 3H); $^{13}$C NMR (CDCl$_3$) δ 213.1, 138.7, 115.6, 94.5, 71.3, 70.6, 63.0, 58.9, 57.3, 55.14, 55.01, 54.8, 40.0, 39.4, 36.5, 35.0, 34.0, 31.9, 30.3, 28.2, 28.1, 27.1, 26.5, 25.2, 24.3.

48

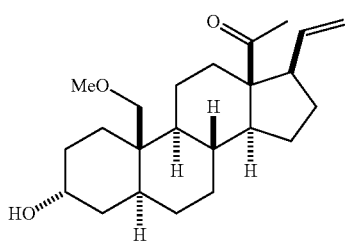

(KK-145)

1-[(3α,5α)-3-Hydroxy-19-methoxy-18-norpregn-20-en-13-yl]ethanone (48, KK-145)

Compound 48 (22 mg, 81%) was prepared from compound 47 as a white solid using the procedure described for the preparation of compound 9 from compound 8. Compound 48 had: mp 124-126° C.; [α]$_D^{23}$ −23.1 (c 0.13, CHCl$_3$); IR $v_{max}$ 3325, 2924, 2868, 1697, 1638, 1446, 1358, 1225 cm$^{-1}$; $^1$H NMR (CDCl$_3$) δ 5.62 (m, 1H), 5.01-5.12 (m, 2H), 4.09 (b s, 1H), 3.37 (s, 2H), 3.21 (s, 3H), 2.41 (m, 1H), 2.27 (m, 1H), 2.05 (s, 3H); $^{13}$C NMR (CDCl$_3$) δ 213.1, 138.6, 115.6, 70.4, 66.4, 63.0, 58.9, 57.2, 55.0, 54.8, 39.6, 39.3, 36.6, 36.1, 35.1, 31.9, 30.3, 29.3, 28.1, 28.0, 26.5, 25.2, 24.3. HRMS (FAB) Calcd for (C$_{23}$H$_{36}$O$_3$Na): 383.2562 Found: 383.2566.

Scheme 5

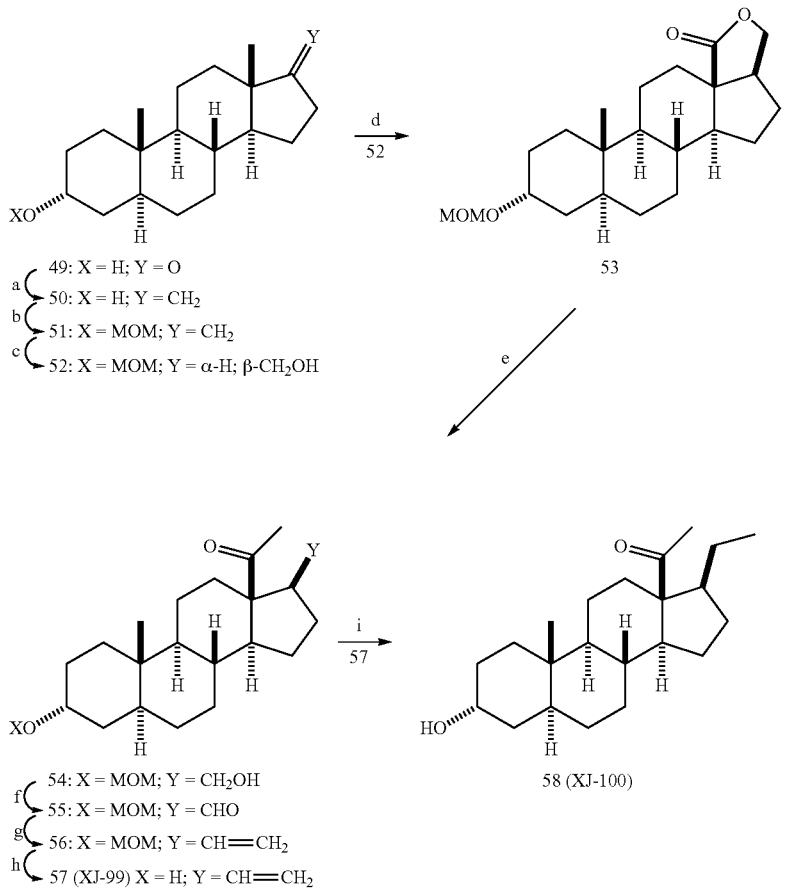

In accordance with Scheme 5, the following compounds were prepared, using methods generally known in the art and as outlined below.

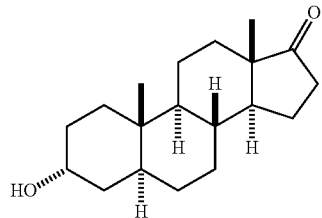

Androsterone (49)

Compound 49 is commercially available and was purchased from the Sigma-Aldrich Chemical Co. (St. Louis, Mo.).

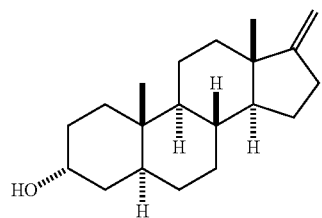

(3α,5α)-17-Methylene-androstan-3-ol (50)

Compound 50 was prepared as described previously (see, Ruzicka, et al., "Steroids and sex hormones. CXXXIX. The relation between constitution and odor of steroids. Methylandrostane and allopregnane derivatives," Helvetica Chimica Acta, Vol. 30, pages 867-878 (1947)).

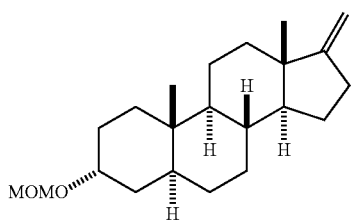

(3α,5α)-3-(Methoxymethoxy)-17-methylene-androstane (51)

Chloromethyl methyl ether (0.43 mL, 5.63 mmol) was added to a solution of compound 50 (540 mg, 1.88 mmol) and N,N-diisopropyl ethylamine (1.63 mL, 9.38 mmol) in $CH_2Cl_2$ (50 mL). The resultant solution was stirred at room temperature for 20 h. The solvent was partially removed and the residue was purified by column chromatography (silica gel; hexanes/EtOAc, 30:1) to give compound 51 (590 mg, 95%) as a white solid: mp 73-75° C.; IR $v_{max}$ 2922, 1655, 1447 cm$^{-1}$; $^1$H NMR (CDCl$_3$) δ 0.77 (s, 3H), 0.81 (s, 3H), 2.22 (m, 1H), 2.47 (m, 1H), 3.37 (s, 3H), 3.83 (m, 1H), 4.62 (m, 2H), 4.66 (m, 2H); $^{13}$C NMR (CDCl$_3$) δ 162.1, 100.5, 94.5, 71.6, 55.1, 54.5 (2×C), 44.1, 39.8, 36.0, 35.7, 35.4, 33.6, 32.8, 31.8, 29.4, 28.5, 26.3, 24.1, 20.6, 18.5, 11.4. Anal. ($C_{22}H_{36}O_2$): C, 79.46; H, 10.91. Found: C, 79.26; H, 11.13.

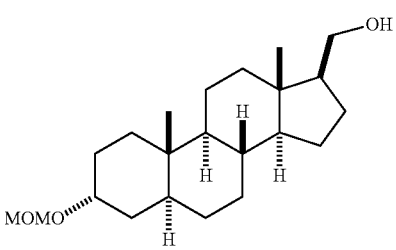

(3α,5α,17β)-3-(Methoxymethoxy)-androstane-17-methanol (52)

$BH_3$.THF (1.0 M in THF, 3.73 mL, 3.73 mmol) was added to compound 51 (620 mg, 0.19 mmol) in anhydrous THF (30 mL) under $N_2$ at 0° C. The resultant solution was stirred at room temperature for 3.5 h and cooled to 0° C. Aqueous NaOH (3 N, 2.6 mL) was added carefully to the reaction followed by 30% $H_2O_2$ (2.6 mL). The reaction mixture was stirred at ambient temperature overnight and extracted with EtOAc. The combined EtOAc extracts were washed with brine until neutral pH and dried. After solvent removal under reduced pressure, the residue was purified by column chromatography (silica gel; hexanes/EtOAc, 6:1) to give compound 52 (560 mg, 86%). It was contaminated with 10% 17α-methanol epimer and was used without further purification. Compound 52 was obtained as viscous oil: IR $v_{max}$ 3401, 2922, 1446 cm$^{-1}$; $^1$H NMR (CDCl$_3$) δ 0.64 (s, 3H), 0.79 (s, 3H), 3.37 (s, 3H), 3.54 (m, 1H), 3.70 (m, 1H), 3.83 (m, 1H), 4.66 (m, 2H); $^{13}$C NMR (CDCl$_3$) δ 11.4, 12.6, 20.5, 24.5, 25.5, 26.3, 28.5, 32.0, 32.8, 33.6, 35.2, 35.9, 38.8, 39.7, 41.9, 53.0, 54.5, 55.1, 56.0, 64.6, 71.6, 94.5.

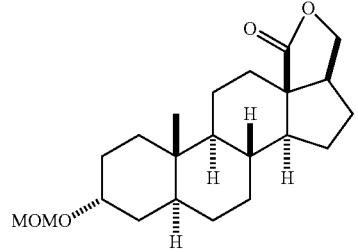

(3α,5α,17β)-17-Hydroxymethyl-3-(methoxymethoxy)-androstan-18-oic acid, γ-lactone (53)

$I_2$ (530 mg, 2.09 mmol) and Pb(OAc)$_4$ (2.07 g, 4.67 mmol) was added to the refluxing solution of compound 52 (460 mg, 1.31 mmol) in cyclohexane (70 mL) under $N_2$. The reaction mixture was refluxed and irradiated with a 300 W tungsten lamp. After 80 min, Pb(OAc)$_4$ (1.15 g, 2.66 mmol) was added again. After the reaction mixture was heated for another 50 min, it was filtered hot and the residue was washed with additional cyclohexane. The combined cyclohexane solution was evaporated to yield an oil, which was dissolved in acetone (50 mL) and Jones reagent was added dropwise at 0° C. until an orange color persisted. The resultant mixture was stirred at 0-5° C. for 30 min. 2-Propanol was added to consume excess oxidant and the acetone was removed under reduced pressure. The residue obtained was dissolved in EtOAc (50 mL), washed with water to neutral pH, and dried. The solvent was removed and the residue was purified by column chromatography (silica gel; hexanes/EtOAc, 20:1) to give compound 53 (250 mg, 53%) as white crystals: mp 144-146° C.; IR $v_{max}$ 2927, 1754 cm$^{-1}$; $^1$H NMR (CDCl$_3$) δ 0.87 (s, 3H), 2.08 (m, 2H), 2.31 (m, 2H), 3.37 (s, 3H), 3.84 (m, 1H), 4.08 (d, 1H, J=9.0 Hz), 4.32 (dd, 1H, J=5.1, 9.0 Hz), 4.67 (m, 2H); $^{13}$C NMR δ 179.5, 94.5, 72.3, 71.6, 55.4, 55.1, 53.5, 53.5, 45.3, 39.7, 36.0, 33.6, 33.5, 33.0, 32.3, 31.7, 31.4, 28.3, 27.4, 26.3, 20.1, 11.4. Anal. (C$_{22}$H$_{34}$O$_4$): C, 72.89; H, 9.45. Found: C, 72.73; H, 9.52.

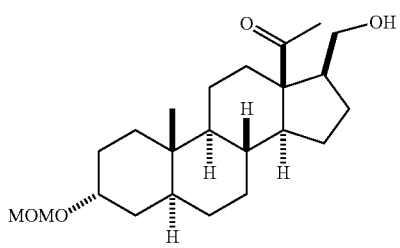

1-[(3α,5α,17β)-17-Hydroxymethyl-3-(methoxymethoxy)-18-norandrostan-13-yl]ethanone (54)

CH$_3$Li (1.6 M in Et$_2$O, 4.3 mL, 6.91 mmol) was added to compound 53 (500 mg, 1.38 mmol) in Et$_2$O (100 mL) under N$_2$ and refluxed for 30 min. After cooling to room temperature, water was added carefully to stop the reaction. The Et$_2$O was washed with 5% aqueous HCl, water and dried. The solvent was removed and the residue was purified by column chromatography (silica gel; CH$_2$Cl$_2$/EtOAc, 10:1) to give compound 54 (450 mg, 86%) as white solid: mp 109-113° C.; IR $v_{max}$ 3498, 2927, 1694 cm$^{-1}$; $^1$H NMR (CDCl$_3$) δ 0.69 (s, 3H), 2.21 (s, 3H), 2.68 (m, 1H), 3.37 (s, 3H), 3.58 (m, 2H), 3.82 (m, 1H), 4.66 (m, 2H); $^{13}$C NMR (CDCl$_3$) δ 213.9, 94.5, 71.6, 63.9, 61.0, 57.6, 55.1, 54.8, 53.0, 39.7, 36.3, 36.2, 35.8, 33.5, 32.8, 31.9, 30.3, 28.3, 26.2, 25.7, 24.8, 23.0, 11.4. Anal. (C$_{23}$H$_{38}$O$_4$): C, 72.98; H, 10.12. Found: C, 72.88; H, 10.20.

(3α,5α,17β)-13-Acetyl-3-(methoxymethoxy)-18-norandrostane-17-carboxaldehyde (55)

Compound 54 (330 mg, 0.87 mmol) in DMSO (1 mL) was added to the solution of iodoxybenzoic acid (400 mg, 1.43 mmol) in DMSO (2.5 mL) and stirred at room temperature for 90 min. Water (30 mL) was added and the precipitate obtained by filtration was washed thoroughly with EtOAc. The EtOAc filtrate was washed with water and dried. The solvent was removed and the residue was purified by flash column chromatography (silica gel eluted with hexanes/EtOAc, 7:1) to give compound 55 (300 mg, 91%) as a mixture of 17α- and 17β-carboxaldehydes in the ratio of 1:4 which was used without further separation or purification.

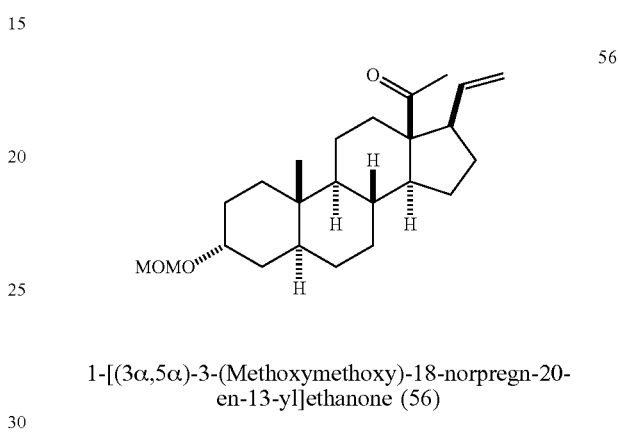

1-[(3α,5α)-3-(Methoxymethoxy)-18-norpregn-20-en-13-yl]ethanone (56)

A mixture of KOBu$^t$ (134 mg, 1.20 mmol) and methyltriphenylphosphonium bromide (570 mg, 1.60 mmol) in anhydrous THF (20 mL) was stirred at room temperature for 30 min under N$_2$ and compound 55 (300 mg, 0.80 mmol) in THF (5 mL) was added. The mixture was stirred at room temperature for 20 min and water (20 mL) was added. The product was extracted into EtOAc. The EtOAc was washed with water, brine and dried. Solvent removal under reduced pressure gave a residue which was purified by column chromatography (silica gel eluted with hexanes/EtOAc, 20:1) to give compound 12 (300 mg, 99%), as a mixture of 17α and 17β diasteromers in the ratio of 5:2. Pure compound 56 (155 mg, 52%) was obtained by recrystallization from hexanes as colorless crystals: mp 115-116° C.; IR $v_{max}$ 2927, 1698 cm$^{-1}$; $^1$H NMR (CDCl$_3$) δ 0.69 (s, 3H), 2.04 (s, 3H), 2.27 (dd, 1H, J=8.7 Hz, J=18.3 Hz), 2.45 (m, 1H), 3.37 (s, 3H), 3.82 (m, 1H), 4.66 (m, 2H), 5.06 (m, 2H), 5.63 (m, 1H); $^{13}$C NMR (CDCl$_3$) δ 212.7, 138.6, 115.6, 94.4, 71.5, 62.9, 57.2, 55.1, 55.0, 54.8, 39.7, 36.1, 35.8, 34.7, 33.5, 32.8, 31.9, 30.3, 28.3, 28.1, 26.2, 25.1, 22.8, 11.5, 11.5, 22.8, 25.1, 26.2, 28.1, 28.3, 30.3, 31.9, 32.8, 33.5, 34.7, 35.8, 36.1, 39.7, 54.8, 55.0, 55.1, 57.2, 62.9, 71.5, 94.4, 115.6, 138.6, 212.7. Anal. (C$_{24}$H$_{38}$O$_3$): C, 76.96; H, 10.23. Found: C, 77.14; H, 10.19.

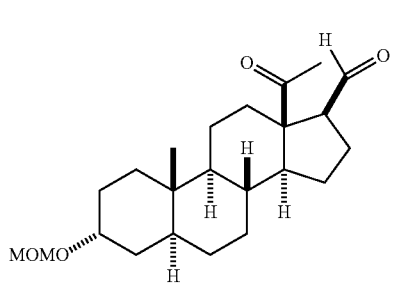

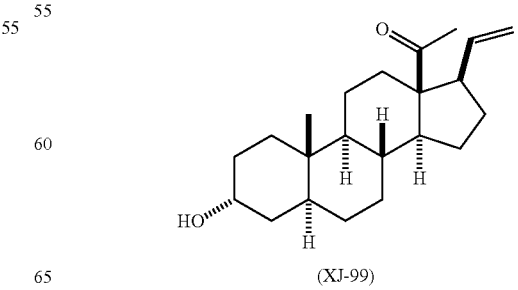

(XJ-99)

1-[(3α,5α)-3-Hydroxy-18-norpregn-20-en-13-yl]ethanone (57, XJ-99)

Compound 57 (24 mg, 97%) was prepared from compound 56 as a white solid using the procedure described for the preparation of compound 9 from compound 8. Compound 57 was obtained as white crystals: mp 178-179.5° C. (from hexanes); IR $v_{max}$ 3306, 2927, 1697 cm$^{-1}$; $^1$H NMR (CDCl$_3$) δ 0.68 (s, 3H), 2.05 (s, 3H), 2.27 (m, 1H), 2.45 (m, 1H), 4.03 (m, 1H), 5.06 (m, 2H), 5.63 (m, 1H); $^{13}$C NMR (CDCl$_3$) δ 212.8, 138.7, 115.6, 66.5, 63.0, 57.2, 55.0, 54.8, 39.1, 36.2, 36.1, 35.8, 34.7, 32.2, 32.0, 30.4, 28.9, 28.3, 28.2, 25.1, 22.9, 11.3. Anal. (C$_{22}$H$_{34}$O$_2$): C, 79.95; H, 10.37. Found: C, 80.18; H, 10.54.

mg) in a Parr hydrogenation apparatus for 4 h. The reaction mixture was filtered through a pad of Celite 545 to remove catalyst and the solvent was removed under reduced pressure. The product was purified by flash column chromatography (silica gel eluted with hexanes/EtOAc, 3:1) to give compound 58 (29 mg, 96%) as white solid: mp 182-184° C. (from Et$_2$O/hexanes); IR $v_{max}$ 3306, 2927, 1694 cm$^{-1}$; $^1$H NMR (CDCl$_3$) δ 0.67 (s, 3H), 0.91 (t, 3H, J=2.9 Hz), 2.09 (s, 3H), 2.50 (m, 1H), 4.04 (m, 1H); $^{13}$C NMR (CDCl$_3$) δ 213.6, 66.5, 61.7, 57.5, 54.9, 52.8, 39.1, 36.3, 36.1, 35.8, 35.3, 32.2, 31.9, 30.4, 28.9, 28.6, 28.3, 24.9, 24.6, 23.0, 13.6, 11.3. Anal. (C$_{22}$H$_{36}$O$_2$): C, 79.46; H, 10.91. Found: C, 79.21; H, 10.78.

Scheme 6

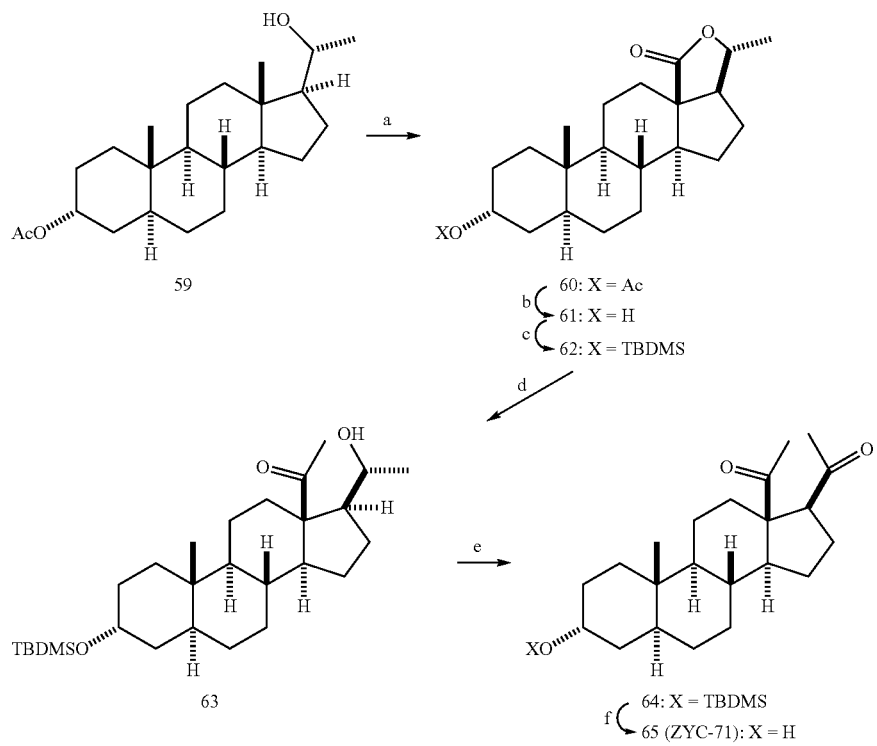

In accordance with Scheme 6, the following compounds were prepared, using methods generally known in the art and as outlined below.

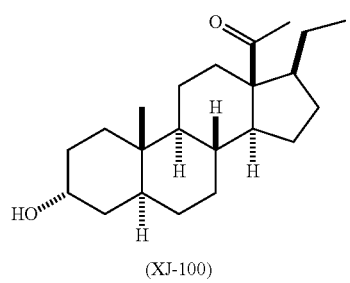

1-[(3α,5α)-3-Hydroxy-18-norpregnan-13-yl]ethanone (58, XJ-100)

Compound 57 (30 mg, 0.91 mmol) was dissolved in EtOAc (10 mL) and hydrogenated (60 psi, H$_2$, 5% Pd/C, 10

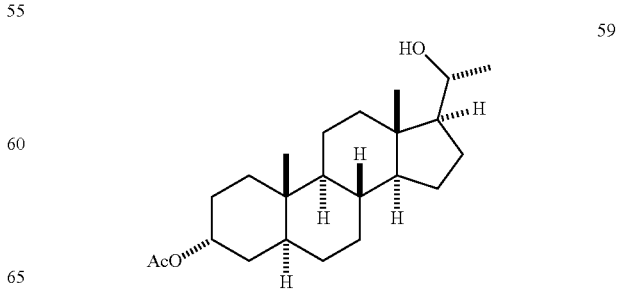

(3α,5α,20R)-Pregnane-3,20-diol, 3-acetate (59)

Product 59 was prepared as described in the literature and had: $^1$H NMR (CDCl$_3$) δ 5.08 (m, 1H), 3.73 (m, 1H), 2.05 (s, 3H), 1.13 (d, 3H, J=6 Hz), 0.80 (s, 3H), 0.75 (s, 3H)(see, Stastna, et al., "Stereoselectivity of sodium borohydride reduction of saturated steroidal ketones utilizing conditions of Luche reduction," Steroids, Vol. 75(10), pages 721-725 (2010)).

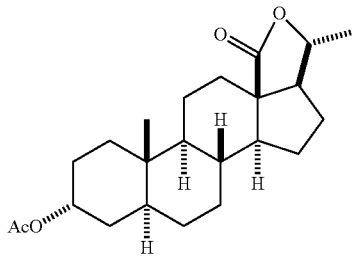

(3α,5α,20R)-3-(Acetyloxy)-20-hydroxy-pregnan-18-oic acid, γ-lactone (60)

Compound 59 (400 mg, 1.1 mmol) was converted to compound 60 (270 mg, 63%) according to procedure used to prepare compound 53. Compound 60 had: IR $v_{max}$ 2935, 2856, 1735, 1449, 1366, 1238 cm$^{-1}$; $^1$H NMR (CDCl$_3$) δ 4.69 (m, 1H), 3.35 (q, 1H, J=6.6 Hz), 2.02 (s, 3H), 1.36 (d, 1H, J=6.6 Hz), 0.91 (s, 3H); $^{13}$C NMR (CDCl$_3$) δ 179.2, 170.6, 82.3, 73.5, 55.9, 53.5, 53.3, 50.5, 44.5, 36.7, 35.5, 34.9, 33.8, 33.0, 32.9, 32.2, 28.2, 27.3, 27.2, 22.5, 21.3, 20.8, 12.1.

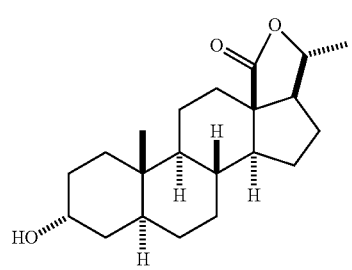

(3α,5α,20R)-3,20-Dihydroxy-pregnan-18-oic acid, γ-lactone (61)

Compound 60 (254 mg, mmol) was dissolved in MeOH (30 ml) and 2% aqueous Na$_2$CO$_3$ was added. The reaction was refluxed overnight, cooled to room temperature and the MeOH removed. Water was added and the product extracted into EtOAc. The EtOAc was washed with brine, dried and after solvent removal product 61 was obtained as a pale yellow solid (240 mg, %). Compound 61 recrystallized from CH$_2$Cl$_2$ and hexanes had: mp 214-215° C.; IR $v_{max}$ 3494, 2943, 2927, 1733, 1447, 1346, 1239 cm$^{-1}$; $^1$H NMR (CDCl$_3$) δ 4.35 (q, 1H, J=6.6 Hz), 4.06 (b s, 1H), 1.37 (d, 3H, 6.6 Hz), 0.87 (3, 3H); $^{13}$C NMR (CDCl$_3$) δ 179.4, 82.4, 66.5, 56.2, 53.7, 53.6, 50.7, 39.0, 36.2, 35.8, 35.1, 33.11, 33.06, 32.32, 32.28, 29.0, 28.3, 27.3, 22.6, 20.5, 11.2. Anal. (C$_{21}$H$_{32}$O$_3$): C, 75.86; H, 9.70. Found: C, 75.68; H, 9.48.

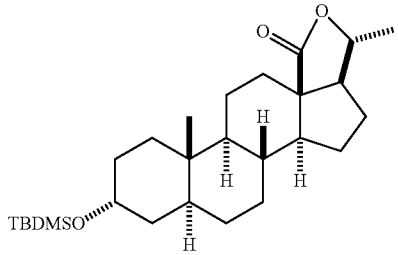

(3α,5α,20R)-3-[[(1,1-Dimethylethyl)dimethylsilyl]oxy]-20-hydroxy-pregnan-18-oic acid, γ-lactone (62)

Compound 61 (220 mg, 0.66 mmol), TBDMSCl (220 mg, 1.46 mmol) and imidazole (190 mg) were dissolved in DMF (4 mL) and stirred overnight at room temperature. The DMF was removed under high vacuum, water was added and the product extracted into EtOAc. The EtOAc was washed with brine, dried and after solvent removal crude product (310 mg) was obtained. Flash column chromatography (silica gel eluted with 5% EtOAc in hexanes) gave compound 62 as a white solid (260 mg, 88%): IR $v_{max}$ 2928, 2856, 1761, 1445, 1372, 1252 cm$^{-1}$; $^1$H NMR (CDCl$_3$) δ 4.32 (q, 1H, J=6.6 Hz), 3.95 (m, 1H), 1.35 (d, 3H, J=6.6 Hz), 0.87 (s, 3H), 0.82 (s, 3H), 0.0 (s, 6H); $^{13}$C NMR (CDCl$_3$) δ 179.4, 82.4, 66.9, 56.4, 53.8, 50.9, 39.1, 36.8, 36.2, 35.2, 33.3, 33.2, 32.6, 32.5, 29.7, 28.4, 27.3, 25.9, 22.7, 20.6, 18.1, 11.5, −4.8.

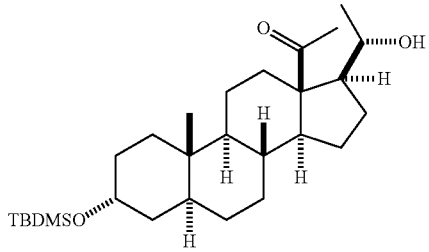

(3α,5α,20R)-13-Acetyl-3-[[(1,1-dimethylethyl)dimethylsilyl]oxy]-18-norpregnan-20-ol (63)

Compound 62 (210 mg, 0.47 mmol) was converted into compound 63 (230 mg) according to the procedure used to prepare compound 54. Compound 63 was a white solid: IR $v_{max}$ 3440, 2855, 2839, 1680, 1470, 1461, 1444, 1369, 1361, 1247 cm$^{-1}$; $^1$H NMR (CDCl$_3$) δ 3.93 (m, 1H), 3.46 (m, 1H), 2.83 (m, 1H), 2.30 (s, 3H), 1.13 (d, 3H, J=6.1 Hz), 0.87 (s, 3H), 0.72 (s, 3H), 0.0 (s, 6H).

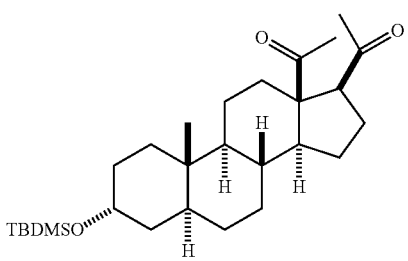

(3α,5α)-13-Acetyl-3-[[(1,1-dimethylethyl)dimethyl-silyl]oxy]-18-norpregnan-20-one (64)

Compound 63 (190 mg, 0.41 mmol) was dissolved in acetone (20 mL) at −20° C. and Jones reagent (0.8 mL) was added. After stirring for 1 h, 2-propanol (1 mL) was added and after 15 min the solvent was removed. Water was added and the product extracted into EtOAc. The EtOAc was washed with brine, dried and the solvent removed. The product was purified by flash column chromatography (silica gel eluted with 20% EtOAc in hexanes) to give compound 64 (120 mg, 63%): IR $v_{max}$ 2928, 2857, 1710, 1361, 1251 cm$^{-1}$; 3.93 (m, 1H), 2.69-2.62 (m, 2H), 2.15 (s, 3H), 2.06 (s, 3H), 0.87 (s, 9H), 0.65 (s, 3H), 0.0 (s, 6H); $^{13}$C NMR (CDCl$_3$) δ 211.8, 209.0, 66.8, 64.4, 61.7, 57.9, 54.6, 39.0, 36.6, 36.3, 36.03, 35.99, 32.4, 32.0, 30.8, 30.1, 29.6, 28.3, 25.8, 25.6, 24.9, 22.8, 18.1, 11.4, −4.86, −4.89.

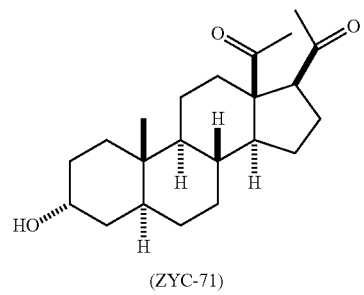

(ZYC-71)

(3α,5α)-13-Acetyl-3-hydroxy-18-norpregnan-20-one (65, ZYC-71)

Compound 64 (70 mg, 0.15 mmol) was dissolved in acetone (20 mL), sulfuric acid (18 N, 0.1 mL) was added and the reaction stirred at room temperature. After 1 hr, additional sulfuric acid was added (18 N, 0.15 mL) and after 2 h sulfuric acid (18 N, 0.1 mL) was again added. After 2.5 h, approximately 50% of the solvent was removed and saturated aqueous NaHCO$_3$ (1 mL) was added. Water was added and the product extracted into EtOAc. The EtOAc was washed with brine, dried and removed to give crude product (50 mg). Purification by flash chromatography (silica gel eluted with 40-50% EtOAc in hexanes) gave compound 65 (40 mg) which contained a trace amount of the 20α-epimer that was removed by recrystallization from CH$_2$Cl$_2$/hexanes. Compound 65 (24 mg) was obtained as a white solid: mp 180-181° C.; IR $v_{max}$ 3442, 2928, 2858, 1696, 1445, 1430 cm$^{-1}$; $^1$H NMR (CDCl$_3$) δ 4.04 (m, 1H), 2.75-2.64 (m, 2H), 2.17 (s, 3H), 2.08 (s, 3H), 1.59 (s, 3H), 0.69 (s, 3H); $^{13}$C NMR (CDCl$_3$) δ 211.8, 209.0, 66.3, 64.2, 61.6, 57.8, 54.5, 39.0, 36.2, 36.08, 35.96, 35.8, 32.1, 31.8, 30.8, 30.1, 28.9, 28.2, 25.5, 24.8, 22.8, 11.2. Anal. (C$_{22}$H$_{34}$O$_3$): C, 76.26; H, 9.89. Found: C, 76.40; H, 9.76.

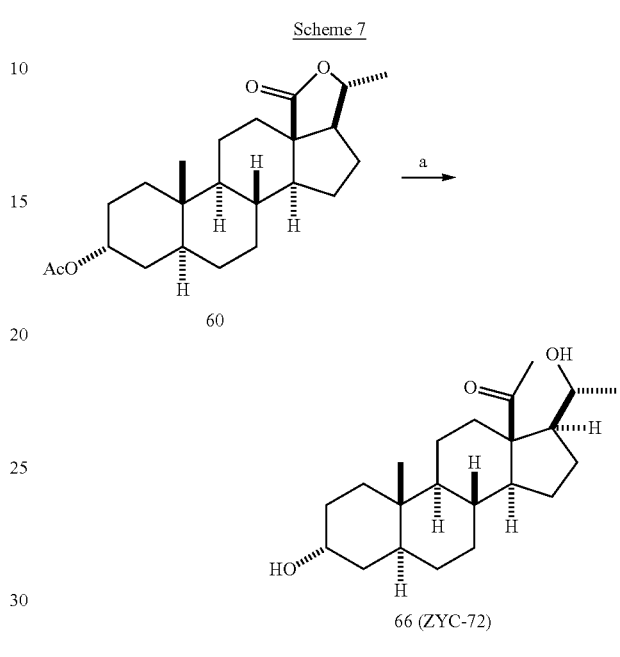

Scheme 7

In accordance with Scheme 7, the following compounds were prepared, using methods generally known in the art and as outlined below.

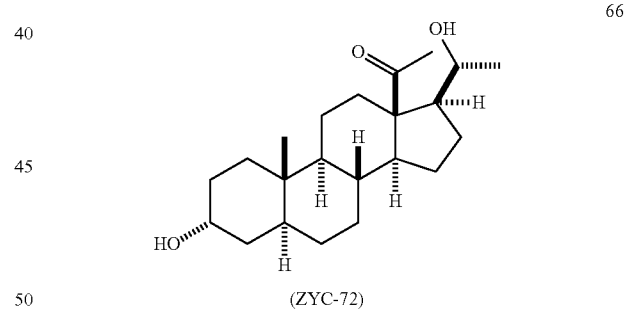

(3α,5α,20R)-13-Acetyl-18-norpregnane-3,20-diol (66, ZYC-72)

Compound 60 (120 mg) was converted to compound 66 using the procedure described for the preparation of compound 54. Compound 66 (50 mg) had: mp 159-161° C.; IR $v_{max}$ 3430, 2915, 1676 cm$^{-1}$; $^1$H NMR (CD$_3$OD) δ 3.94 (m, 1H), 3.34 (m, 1H), 2.89 (dm, 1H, J=3.7 Hz), 2.30 (d, 1H, J=1.3 Hz), 1.11 (d, 3H, J=2.2 Hz), 0.70 (s, 3H); $^{13}$C NMR (THF-d$_5$) δ 213.6, 70.4, 62.6, 60.2, 59.1, 56.1, 40.1, 38.1, 37.5, 37.4, 37.1, 33.4, 33.3, 30.2, 29.8, 27.6, 24.9, 26.0, 24.9, 24.7, 24.2, 11.9. Anal. (C$_{22}$H$_{36}$O$_3$): C, 75.82; H, 10.41. Found: C, 76.01; H, 10.50.

Scheme 8

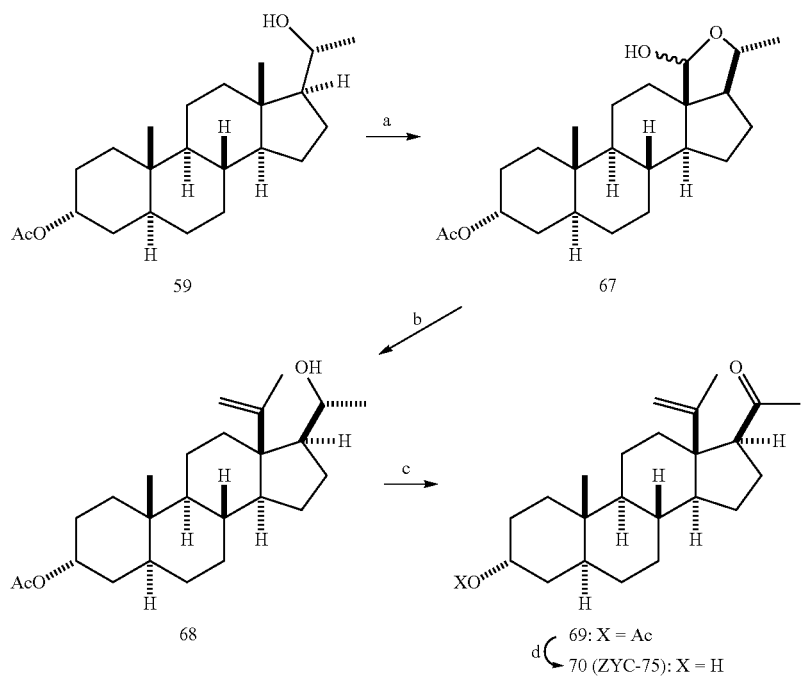

In accordance with Scheme 8, the following compounds were prepared, using methods generally known in the art and as outlined below.

(3α,5α,20R)-18,20-epoxy-Pregnane-3,18-diol (67)

Compound 59 (610 mg, 1.68 mmol) was dissolved in cyclohexane and stirred under $N_2$. $CaCO_3$ (680 mg), Pb(OAc)$_4$ (4.12 g), and $I_2$ (1.06 g) were irradiated with a high intensity tungsten lamp for 130 min. The solvent refluxed during irradiation. The reaction was allowed to cool to room temperature, filtered and the cyclohexane solution washed with 10% aqueous $Na_2S_2O_3$, brine and dried. Solvent removal gave an oil (1.07 g). Purification by flash column chromatography (silica gel eluted with 5-30% EtOAc in hexanes) gave compound 67 (272 mg) as a mixture of epimeric 18,20-epoxy compounds. The epimeric mixture had: IR $v_{max}$ 3469, 2934, 2858, 1736, 1446, 1375, 1362, 1235; a partial list of resonances consistent with the assigned structure is as follows: $^1$H NMR (CDCl$_3$) δ 6.20 (s), 6.05 (s), 5.00 (m), 4.39-4.33 (m), 4.21-4.01), 2.077 (s), 2.076 (s), 2.08 (s), 2.07 (s), 2.05 (s), 0.74 (s), 0.69 (s); $^{13}$C NMR 170.7, 170.1, 102.0, 100.5, 85.7, 84.2, 82.4, 70.1, 70.0, 58.9, 57.1, 56.9, 56.2, 55.0, 54.9, 54.7, 54.6, 53.5, 53.4, 50.7.

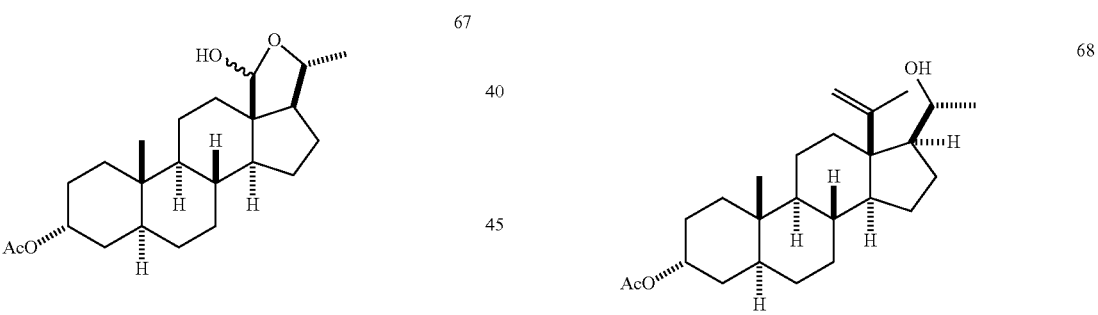

(3α,5α,20R)-13-Isopropenyl-18-norpregnan-3,20-diol, 3-acetate (68)

CH$_3$PPh$_3$Br (1.52 g, 4.25 mmol) and KOBu$^t$ (480 mg, 4.28 mmol) were stirred in THF (25 mL) at room temperature for 30 min. Compound 67 (124 mg, 0.33 mmol) dissolved in THF (5 mL) was added and stirring at room temperature continued for 15 min, at reflux for 4.75 h and overnight at room temperature. The solvent was removed, water added and the product extracted into EtOAc. The EtOAc was washed with brine, dried and removed to yield an oily solid. Purification by flash column chromatography (silica gel eluted with 5-35% EtOAc in hexanes) gave compound 68 (25 mg): IR $v_{max}$ 3473, 2948, 2921, 2866, 2841, 1727, 1446, 1375, 1270 cm$^{-1}$; $^1$H NMR δ 5.66 (dd, 1H J=11.3 Hz, J=17 Hz), 5.32 (dd, 1H, J=1.6 Hz, J=11 Hz), 5.19 (dd, 1H, J=1.6 Hz, J=18.7 Hz), 5.00 (b s, 1H), 3.61 (m, 1H), 2.50 (dm, 1H, J=13 Hz), 2.05 (s, 3H), 1.10 (d, 3H, J=6.3 Hz), 0.71 (s, 3H); $^{13}$C NMR δ 170.6, 138.3, 115.9, 70.7, 70.1, 58.9, 56.8, 54.7, 50.3, 40.4, 36.3, 35.8, 32.9, 31.8, 28.2, 26.1, 25.8, 24.1, 22.7, 21.5, 20.9, 11.3.

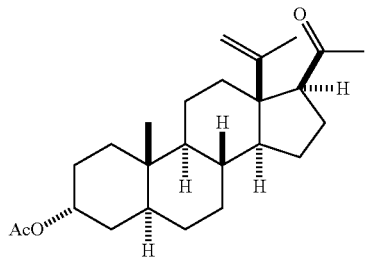

(3α,5α)-3-Hydroxy-13-isopropenyl-18-norpregnan-20-one, 3-acetate (69)

Compound 68 (31 mg, mmol) was dissolved in acetone (1.5 mL) and cooled to −5° C. Jones reagent (0.1 mL) was added and stirring continued for 45 min. 2-Propanol (a few drops) was added and stirring continued for 15 min. The solvent was removed and the crude product purified by flash column chromatography (silica gel eluted with 25% EtOAc in hexanes) to give compound 69 (23 mg): $^{1}$H NMR (CDCl$_3$) δ 5.57 (dd, 1H, J=11.3 Hz, J=17.9 Hz), 5.18 (d, 1H, J=11.2 Hz), 5.01-4.95 (m, 2H), 2.65-2.51 (m, 2H), 2.21 (m, 1H), 2.06 (s, 3H), 2.05 (s, 3H), 0.72 (s, 3H); $^{13}$C NMR (CDCl$_3$) δ 208.3, 170.6, 136.5, 116.0, 70.0, 64.8, 57.5, 54.4, 51.1, 39.9, 36.4, 35.8, 34.9, 32.9, 32.8, 31.7, 31.0, 28.1, 26.1, 23.9, 22.8, 21.5, 21.1, 11.3.

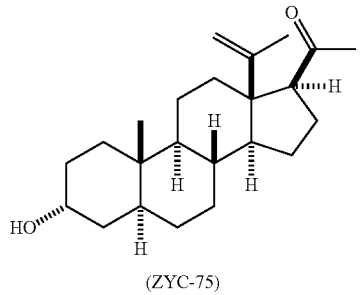

(3α,5α)-3-Hydroxy-13-isopropenyl-18-norpregnan-20-one (70, ZYC-75)

Compound 69 (23 mg) in aqueous MeOH containing Na$_2$CO$_3$ (3 mL of a solution containing 250 mg Na$_2$CO$_3$ in 1.3 ml water and 11.7 mL MeOH) was heated to reflux, cooled and the solvent removed. The product was purified by flash column chromatography (silica gel eluted with 5-60% EtOAc in hexanes) to give compound 70 (17 mg) as a white solid: mp 146-147° C.; IR ν$_{max}$ 3304, 2929, 2876, 2852, 1712, 1636, 1450 cm$^{-1}$; $^{1}$H NMR (CDCl$_3$) δ 5.56 (dd, 1H, J=11.3 Hz, J=17.9 Hz), 5.18 (dd, 1H, J=1.1 Hz, J=11.3 Hz), 4.98 (dd, 1H, J=1.5 Hz, J=17.8 Hz), 4.04 (m, 1H), 2.62-2.50 (m, 2H), 2.25-2.13 (m, 1H), 2.06 (s, 3H), 0.70 (3H); $^{13}$C NMR (CDCl$_3$) δ 208.3, 136.6, 115.9, 66.5, 64.8, 57.6, 54.6, 51.2, 39.1, 36.4, 36.1, 35.9, 34.9, 32.2, 31.8, 31.0, 29.0, 28.3, 23.9, 22.8, 21.1, 11.2. Anal. (C$_{22}$H$_{34}$O$_2$): C, 79.95; H, 10.37. Found: C, 79.86; H, 10.16.

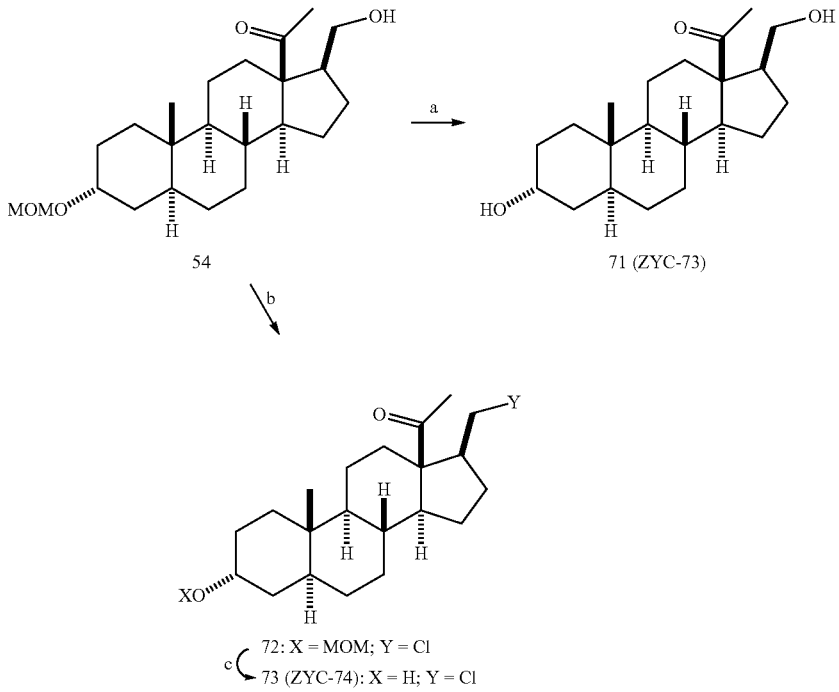

In accordance with Scheme 9, the following compounds were prepared, using methods generally known in the art and as outlined below.

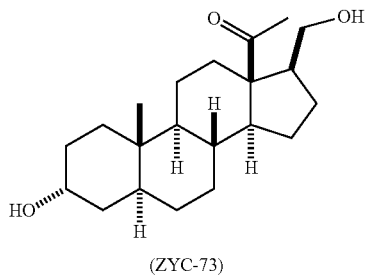

1-[(3α,5α,17β)-3-Hydroxy-17-hydroxymethyl-18-norandrostan-13-yl]ethanone (71, ZYC-73)

Compound 71 (17 mg, 68%) was prepared from compound 54 using the procedure described for the preparation of compound 57 from compound 56. Compound 71 was a white solid: mp 166-168° C.; IR $v_{max}$ 3339, 2929, 2861, 1696, 1445 cm$^{-1}$; $^1$H NMR (acetone-d$_6$) δ 3.93 (m, 1H), 3.75 (dd, 1H, J=4.2 Hz, J=4.5 Hz), 3.54-3.46 (m, 2H), 3.30 (d, 1H, J=3 Hz), 2.76 (dm, 1H, J=13.7), 2.20 (s, 3H), 0.68 (s, 3H); $^{13}$C NMR (acetone-d$_6$) 213.25, 66.0, 63.7, 61.7, 58.7, 56.0, 54.1, 39.8, 37.1, 37.0, 39.9, 33.2, 33.0, 30.7, 30.2, 29.8, 26.6, 25.7, 23.8, 11.8. Anal. (C$_{21}$H$_{34}$O$_3$): C, 75.41; H, 10.25. Found: C, 74.95; H, 9.95.

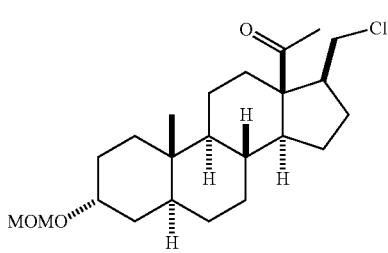

1-[(3α,5α,17β)-17-Chloromethyl-3-(methoxymethoxy)-18-norandrostan-13-yl]ethanone (72)

Compound 71 (78 mg, 0.21 mmol) and Et$_3$N (0.035 mL, 0.25 mmol) were dissolved in CH$_2$Cl$_2$ and cooled to 0° C. CH$_3$SO$_2$Cl (0.025 mL, 0.32 mL) was added and stirring continued overnight in a cold room maintained at around 4° C. Water was added and the product was extracted into CH$_2$Cl$_2$. The CH$_2$Cl$_2$ was washed with brine, dried and removed to yield the crude product as crystals in a brown oil. Purification by flash column chromatography (silica gel eluted with 5-15% EtOAc in hexanes) gave compound 72 (20 mg, 25%): IR $v_{max}$ 2935, 2876, 2836, 1688, 1447, 1357, 1214 cm$^{-1}$; $^1$H NMR δ 4.65 (m, 2H), 3.82 (m, 1H), 3.51 (dd, 1H, J=7.7 Hz, J=11 Hz), 3.41-3.35 (overlapped m, 1H), 3.37 (s, 3H), 2.70 (dt, 1H, J=13.4 Hz, J=3 Hz), 2.21 (s, 3H), 0.68 (s, 3H); $^{13}$C NMR δ 212.5, 94.6, 71.6, 61.7, 57.9, 55.1, 54.7, 52.9, 45.7, 39.8, 36.4, 35.9, 33.6, 32.9, 31.8, 30.4, 28.4, 26.4, 24.8, 23.0, 11.5.

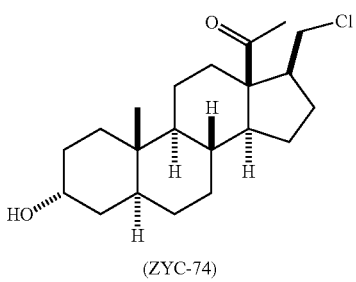

1-[(3α,5α,17β)-17-Chloromethyl-3-hydroxy-18-norandrostan-13-yl]ethanone (73, ZYC-74)

Compound 73 (13 mg, %) was prepared from compound 72 using the procedure described for the preparation of compound 57 from compound 56. Compound 73 was a white solid: mp 161-162° C.; IR $v_{max}$ 3306, 2929, 2861, 1695, 1445 cm$^{-1}$; $^1$H NMR (CDCl$_3$) δ 4.04 (m, 1H), 3.51 (dd, 1H, J=7.7 Hz, J=10.8 Hz), 3.38 (dd, 1H, J=7.4 Hz, J=10.8 Hz), 2.72 (dm, 1H, J=13.4 Hz), 2.21 (s, 3H), 0.68 (s, 3H); $^{13}$C NMR (CDCl$_3$) δ 212.8, 66.4, 61.6, 57.8, 54.6, 52.8, 45.7, 39.1, 36.3, 36.0, 35.8, 32.1, 31.8, 30.4, 28.9, 28.3, 28.2, 24.7, 22.9, 11.2. HRMS (EI) Calcd for (C$_{21}$H$_{33}$ClO$_2$): 352.2169 ($^{35}$Cl isotope). Found 352.2170.

Scheme 10

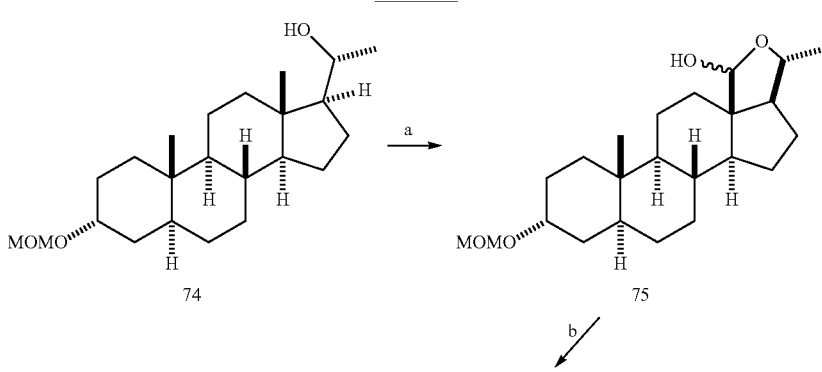

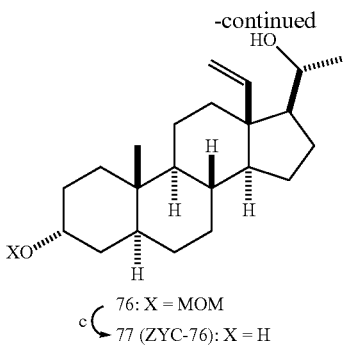

76: X = MOM
77 (ZYC-76): X = H

In accordance with Scheme 10, the following compounds were prepared, using methods generally known in the art and as outlined below.

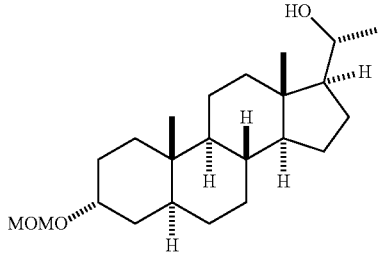

(3α,5α,20R)-3-[[(1,1-Dimethylethyl)dimethylsilyl]oxy]-pregnan-20-ol (74)

The commercially available steroid (3α,5α)-3-hydroxy-pregnan-2-one (1 g, 3.14 mmol) was dissolved in stirred CH$_2$Cl$_2$ (20 mL) and methoxymethychloride (0.75 mL) was added. The reaction was cooled to 0° C. and diisopropylethylamine (2.6 mL) was added and stirring was continued at 0° C. for 1.5 h and then at room temperature overnight. Aqueous NH$_4$Cl was added and the product extracted into CH$_2$Cl$_2$. The CH$_2$Cl$_2$ was washed with brine, dried and the solvent removed. The crude product (1.58 g) was purified by flash column chromatography (silica gel eluted with 20% EtOAc in hexanes to give the intermediate (3α,5α)-3-[[(1,1-Dimethylethyl)dimethylsilyl]oxy]-pregnan-20-one (1.01 g) which was reduced to a mixture of the 20R and 20S alcohols by NaBH$_4$ (added in four portions) in MeOH (30 mL) and THF (10 mL) at −5° C. to 0° C. The reaction time was 1 h. The solvent was removed, water was added and the product extracted into EtOAc. The EtOAc was dried and removed and the 20R and 20S alcohols (~4:1 ratio, 1 g) were purified and separated by flash column chromatography (silica gel eluted with 5-30% EtOAc in hexanes) to give pure product 74 (0.84 g) as a white solid which had: $^1$H NMR (CDCl$_3$) δ 4.66 (m, 2H), 3.82 (m, 1H), 3.72 (m, 1H), 3.37 (s, 3H), 2.03 (m, 1H), 1.12 (d, 3H, J=6.3 Hz), 0.79 (s, 3H), 0.74 (s, 3H).

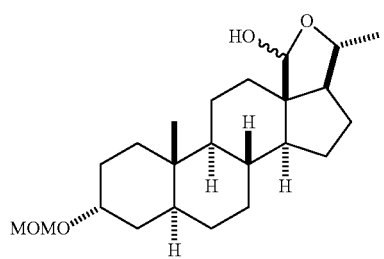

(3α,5α,20R)-3-[[(1,1-Dimethylethyl)dimethylsilyl]oxy]-18,20-epoxy-Pregnan-18-ol (75)

Compound 75 (240 mg crude containing compound 74) was prepared from compound 74 using the procedure described for the preparation of compound 67 from compound 59. Compound 75 was not characterized.

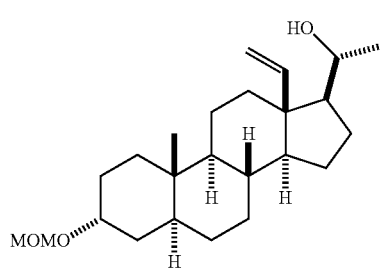

(3α,5α)-3-[[(1,1-Dimethylethyl)dimethylsilyl]oxy]-13-ethenyl-18-norpregnan-20-ol (76)

Compound 76 (29 mg) was prepared from compound 75 using the procedure described for the preparation of compound 68 from compound 67. Compound 76 was a crystalline solid: $^1$H MNR (CDCl$_3$) δ 5.66 (dd, 1H, J=11.5 Hz, J=12.7 Hz), 5.33-5.16 (m, 2H), 4.65 (m, 2H), 3.81 (m, 1H), 3.60 (m, 1H), 3.36 (s, 3H), 2.50 (dm, 1H, J=12.6 Hz), 1.09 (d, 1H, J=6.3 Hz), 0.71 (s, 3H); $^{13}$C NMR (CDCl$_3$) δ 138.2, 115.7, 94.3, 71.5, 70.6, 58.6, 56.7, 55.0, 54.6, 50.1, 39.5, 36.2, 35.7, 35.6, 33.5, 32.7, 31.7, 28.3, 26.1, 25.6, 23.9, 22.6, 20.7, 11.3.

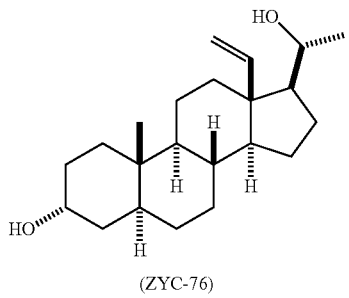

(3α,5α,20R)-13-Ethenyl-18-norpregnan-3,20-diol
(77, ZYC-76)

Compound 77 (19 mg, 76%) was prepared from compound 76 using the procedure described for the preparation of compound 57 from compound 56. Compound 77 was a white solid: mp 193-195° C.; IR $v_{max}$ 3369, 2921, 2873, 1633, 1445 cm$^{-1}$; $^1$H NMR (CDCl$_3$) δ 5.64 (dd, 1H, J=11.2 Hz, J=17.9 Hz), 5.32 (dd, 1H, J=1.9 Hz, J=11.3 Hz), 5.19 (dd, 1H, J=1.7 Hz, J=17.9 Hz), 4.03 (m, 1H), 3.61 (m, 1H), 2.48 (dt, 1H; J=2.7 Hz, J=12.7 Hz), 1.09 (d, 3H, J=6.3 Hz), 0.70 (s, 3H); $^{13}$C NMR (CDCl$_3$) δ 138.2, 115.8, 70.7, 66.5, 58.7, 56.7, 54.6, 50.1, 39.0, 36.2, 36.0, 35.8, 35.6, 32.1, 31.8, 29.0, 28.3, 25.7, 24.0, 22.6, 20.8, 11.2. Anal. (C$_{22}$H$_{36}$O$_2$): C, 79.46; H, 10.91. Found: C, 79.54; H, 10.79.

[$^{35}$S]-TBPS Displacement

The IC$_{60}$ values for non-competitive displacers of [$^{35}$S]-TBPS from the picrotoxin binding site on GABA$_A$ receptors are reported in Table 1.

TABLE 1

Inhibition of [$^{35}$S]-TBPS Binding

| Compound | IC$_{50}$ (nM) | n$_{Hill}$ |
| --- | --- | --- |
| KK-140 | 17 ± 3 | 0.79 ± 0.07 |
| KK-143 | 270 ± 19 | 1.14 ± 0.08 |
| KK-144 | 72 ± 16 | 1.31 ± 0.32 |
| KK-145 | 53 ± 4 | 1.21 ± 0.10 |
| XJ-99 | 43 ± 12 | 1.43 ± 0.44 |
| XJ-100 | 276 ± 130 | 0.78 ± 0.24 |
| ZYC-71 | 82 ± 7 | 1.11 ± 0.08 |
| ZYC-72 | 978 ± 618 | 0.70 ± 0.24 |
| ZYC-73 | 1,460 ± 270 | 1.02 ± 0.13 |
| ZYC-74 | 415 ± 83 | 1.02 ± 0.17 |
| ZYC-75 | 27 ± 5 | 1.02 ± 0.15 |
| ZYC-76 | 497 ± 59 | 1.50 ± 0.21 |

Results presented are from duplicate experiments performed in triplicate. Error limits are calculated as standard error of the mean. Methods used are known in the art (see Jiang, X., et al., Neurosteroid analogues. 9. Conformationally constrained pregnanes: structure-activity studies of 13,24-cyclo-18,21-dinorcholane analogues of the GABA modulatory and anesthetic steroids (3α,5α)- and (3α,5α)-3-hydroxypregnan-20-one. J. Med. Chem., 46: 5334-48 (2003)—the contents of which are hereby incorporated by reference in their entirety).

Electrophysiology Results

The compounds of the present disclosure were evaluated for the ability to potentiate chloride currents mediated by 2 μM GABA at rat α$_1$β$_2$γ$_{2L}$ type GABA$_A$ receptors expressed in Xenopus laevis oocytes and the results are shown in Table 2.

TABLE 2

Analogue Potentiation of GABA Effects at Rat α1β2γ2GABA$_A$ Receptors Expressed in Frog Oocytes

| | oocyte electrophysiology$^a$ | | | |
| --- | --- | --- | --- | --- |
| Compound | 0.1 μM | 1 μM | 10 μM | (gating) 10 μM |
| KK-140 | 5.39 ± 2.76 | 11.90 ± 1.08 | 17.29 ± 2.10 | 0.27 ± 0.06 |
| KK-143 | 1.23 ± 0.06 | 2.93 ± 0.30 | 8.43 ± 0.69 | 0.07 ± 0.02 |
| KK-144 | 1.40 ± 0.11 | 5.38 ± 0.55 | 10.59 ± 1.31 | 0.18 ± 0.02 |
| KK-145 | 1.75 ± 0.14 | 13.74 ± 3.71 | 35.57 ± 12.85 | 0.56 ± 0.07 |
| XJ-99 | 1.73 ± 0.20 | 3.96 ± 0.99 | 4.37 ± 1.28 | 0.07 ± 0.02 |
| XJ-100 | 1.33 ± 0.20 | 5.01 ± 0.89 | 8.41 ± 0.66 | −0.06 ± 0.06 |
| ZYC-71 | 1.82 ± 0.03 | 9.31 ± 0.46 | 19.44 ± 1.69 | 0.22 ± 0.01 |
| ZYC-72 | 0.80 ± 0.08 | 1.30 ± 0.11 | 2.78 ± 0.37 | −0.03 ± 0.11 |
| ZYC-73 | 1.07 ± 0.15 | 1.42 ± 0.16 | 6.16 ± 0.71 | −0.09 ± 0.09 |
| ZYC-74 | 1.06 ± 0.04 | 1.98 ± 0.21 | 9.38 ± 1.71 | 0.03 ± 0.01 |
| ZYC-75 | 1.93 ± 0.18 | 7.07 ± 1.89 | 12.02 ± 3.53 | 0.20 ± 0.05 |
| ZYC-76 | 1.00 ± 0.01 | 1.56 ± 0.13 | 7.28 ± 1.76 | 0.04 ± 0.02 |

$^a$The GABA concentration used for the control response was 2 μM. Each compound was evaluated on at least four different oocytes at the concentrations indicated, and the results reported are the ratio of currents measured in the presence/absence of added compound. Gating represents direct current gated by 10 μM compound in the absence of GABA, and this current is reported as the ratio of compound only current/2 μM GABA current. Error limits are calculated as standard error of the mean (N≥4). Methods used are known in the art (see Jiang, X., et al.).

Tadpole Loss of Righting and Swimming

Table 3 discloses the anesthetic effects of the compounds of the present disclosure. In particular, the anesthetic effect of the compounds of the present disclosure on Loss of Righting Reflex (LRR) and Loss of Swimming Reflex (LSR).

TABLE 3

Tadpole Loss of Righting (LRR) & Loss of Swimming (LSR) EC$_{50}$ Values (μM) Reflexes by Analogues

| Compound | Tadpole LRR EC$_{50}$ (μM) | Tadpole LRR n$_{Hill}$ | Tadpole LSR EC$_{50}$ (μM) | Tadpole LSR n$_{Hill}$ |
| --- | --- | --- | --- | --- |
| KK-140 | 0.05 ± 0 | −1.80 ± 0.10 | 0.30 ± 0 | −3.5 ± 0.3 |
| KK-143 | 0.61 ± 0.06 | −1.80 ± 0.27 | 1.73 ± 0.03 | −36.3 ± 0.1 |
| KK-144 | 0.18 ± 0.01 | −2.25 ± 0.15 | 0.55 ± 0.01 | −33.3 ± 0.1 |
| KK-145 | 0.14 ± 0.01 | −2.55 ± 0.42 | 0.55 ± 0.01 | −33.3 ± 0.1 |
| XJ-99 | 0.05 ± 0.00 | −2.90 ± 0.05 | 0.14 ± 0.0 | −3.95 ± 0.02 |
| XJ-100 | 0.46 ± 0.16 | −1.23 ± 0.44 | >10 | — |
| ZYC-71 | 1.73 ± 0.01 | −4.00 ± 0.02 | 5.48 ± 0.15 | −33.5 ± 0.1 |
| ZYC-72 | 3.06 ± 0.00 | −21.3 ± 0.0 | >10 | — |
| ZYC-73 | >10 | — | None | — |
| ZYC-74 | 3.33 ± 1.41 | −2.36 ± 2.35 | 5.48 ± 0.20 | −33.2 ± 0.2 |
| ZYC-75 | 0.67 ± 0.01 | −2.26 ± 0.22 | 2.64 ± 0.01 | −22.8 ± 0.7 |
| ZYC-76 | 742 ± 202 | −1.64 ± 0.58 | 1.74 ± 0.03 | −35.9 ± 0.1 |

Methods used are known in the art (see Jiang, X., et al.). Error limits are calculated as standard error of the mean (N=10 or more animals at each of five or more different concentrations).

General Methods

The compounds discussed in the present disclosure were produced as discussed elsewhere throughout this disclosure and by the following methods.

Solvents were either used as purchased or dried and purified by standard methodology. Extraction solvents were dried with anhydrous Na$_2$SO$_4$ and after filtration, removed on a rotary evaporator. Flash chromatography was performed using silica gel (32-63 μm) purchased from Scientific Adsorbents (Atlanta, Ga.). Melting points were determined on a Kofler micro hot stage and are uncorrected. FT-IR spectra were recorded as films on a NaCl plate. NMR spectra were recorded in $CDCl_3$ at ambient temperature at 300 MHz ($^1H$) or 74 MHz ($^{13}C$). Purity was determined by TLC on 250 μm thick Uniplates™ from Analtech (Newark, Del.). All pure compounds (purity >95%) gave a single spot on TLC. Elemental analyses were performed by M-H-W Laboratories (Phoenix, Ariz.).

EQUIVALENTS AND SCOPE

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. It is also noted that the terms "comprising", "including", "having" or "containing" are intended to be open and permits the inclusion of additional elements or steps.

What is claimed is:

1. A method of inducing anesthesia in a subject in need thereof, the method comprising administering to the subject a therapeutically effective amount of a compound of Formula (I):

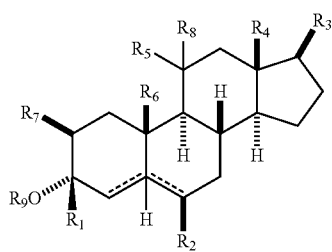

or a pharmaceutically acceptable salt thereof;
wherein:
$R_1$ is H, optionally substituted $C_1$-$C_4$ alkyl, optionally substituted $C_2$-$C_4$ alkenyl, or optionally substituted $C_2$-$C_4$ alkynyl;
$R_2$ is H, optionally substituted $C_1$-$C_4$ alkoxy, aryloxy, optionally substituted $C_2$-$C_4$ alkenoxy, optionally substituted $C_2$-$C_4$ alkynoxy, or —O—C(O)—$R_x$, where $R_x$ is optionally substituted $C_1$-$C_{20}$ alkyl;
$R_3$ is H, optionally substituted $C_1$-$C_4$ alkyl, optionally substituted $C_2$-$C_4$ alkenyl, optionally substituted alkynyl, cyclopropyl, or C(O)$R_y$, where $R_y$ is $C_1$-$C_4$ alkyl, $C_2$-$C_4$ alkenyl or $C_2$-$C_4$ alkynyl;
$R_4$ is optionally substituted $C_2$-$C_4$ alkenyl, optionally substituted $C_2$-$C_4$ alkynyl, optionally substituted cyclopropyl, or C(O)$R_z$, where $R_z$ is $C_1$-$C_4$ alkyl, $C_2$-$C_4$ alkenyl or $C_2$-$C_4$ alkynyl;
$R_5$ is H, =O, or O$R_v$, where $R_v$ is H, optionally substituted $C_1$-$C_4$ alkyl, optionally substituted $C_2$-$C_4$ alkenyl, optionally substituted $C_2$-$C_4$ alkynyl, or optionally substituted aryl;
$R_6$ is H, optionally substituted $C_1$-$C_4$ alkyl, optionally substituted $C_2$-$C_4$ alkenyl, or optionally substituted $C_2$-$C_4$ alkynyl;
$R_7$ is H, optionally substituted $C_1$-$C_4$ alkoxy, aryloxy, morpholinyl, optionally substituted $C_2$-$C_4$ alkenoxy, optionally substituted $C_2$-$C_4$ alkynoxy, or —O—C(O)—$R_w$, where $R_w$ is optionally substituted $C_1$-$C_{20}$ alkyl;
$R_8$ is, when present, H, $C_1$-$C_4$ alkyl, $C_2$-$C_4$ alkenyl, or $C_2$-$C_4$ alkynyl;
$R_9$ is H or C(O)$R_u$, where $R_u$ is optionally substituted $C_1$-$C_{20}$ alkyl, optionally substituted $C_2$-$C_{20}$ alkenyl, or optionally substituted $C_2$-$C_{20}$ alkynyl;
wherein the $C_5$—H is in the alpha configuration; and,
- - - denotes an optional, additional C—C bond, resulting in either a C=C bond between $C_4$-$C_5$ or $C_5$-$C_6$, with the proviso that when present, the $C_5$—H substituent is not present.

2. The method of claim 1, wherein $R_9$ is H.
3. The method of claim 1, wherein $R_2$ is H or —$OCH_3$.
4. The method of claim 1, wherein $R_5$ is H or —$OCH_3$.
5. The method of claim 1, wherein $R_6$ is methyl or —$CH_2OCH_3$.
6. The method of claim 1, wherein $R_7$ is H or —$OCH_3$.
7. The method of claim 1, wherein $R_4$ is —CH=$CH_2$ or —C(O)$CH_3$.
8. The method of claim 1, wherein $R_3$ is selected from the group consisting of —CH=$CH_2$, ethyl, —C(O)$CH_3$, hydroxy alkyl, and haloalkyl.
9. The method of claim 8, wherein $R_3$ is hydroxy alkyl.
10. The method of claim 8, wherein $R_3$ is —$CH_2Cl$.
11. The method of claim 8, wherein $R_3$ is selected from the group consisting —C(OH)$CH_3$ and —$CH_2$(OH).
12. The method of claim 1, wherein $R_1$ is H.
13. The method of claim 1, wherein the compound is of the structure:

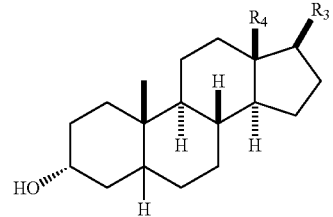

wherein $R_3$ is H, optionally substituted $C_1$-$C_4$ alkyl, optionally substituted $C_2$-$C_4$ alkenyl, optionally substituted alkynyl, cyclopropyl, or C(O)$R_y$, where $R_y$ is $C_1$-$C_4$ alkyl, $C_2$-$C_4$ alkenyl or $C_2$-$C_4$ alkynyl; and,
$R_4$ is optionally substituted $C_2$-$C_4$ alkenyl, optionally substituted $C_2$-$C_4$ alkynyl, optionally substituted cyclopropyl, or C(O)$R_z$, where $R_z$ is $C_1$-$C_4$ alkyl, $C_2$-$C_4$ alkenyl or $C_2$-$C_4$ alkynyl.

14. The method of claim 1, wherein the compound is of the structure selected from the group consisting of:

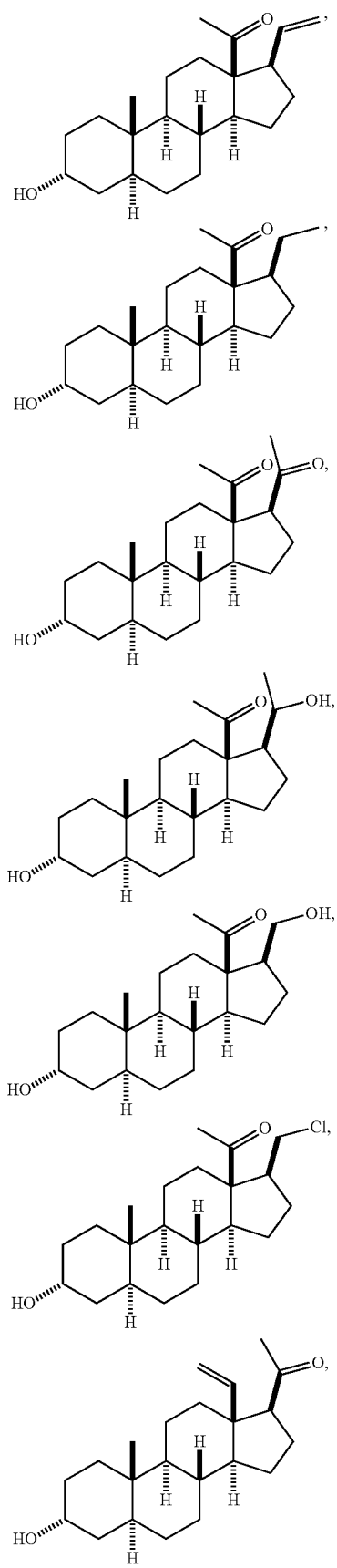
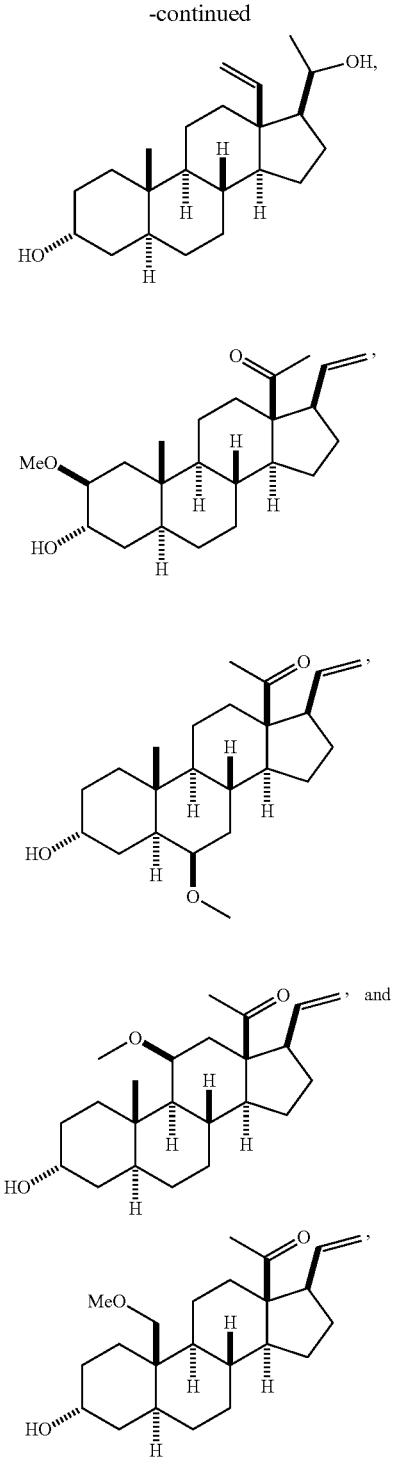
or a pharmaceutically acceptable salt thereof.
15. A pharmaceutically acceptable salt of a compound of the method of claim 1.
16. A pharmaceutical composition comprising a compound of the method of claim 1, a pharmaceutically acceptable salt thereof, or a combination of two or more thereof, and a pharmaceutically acceptable carrier.
* * * * *